United States Patent
Donald et al.

(10) Patent No.: US 10,774,314 B2
(45) Date of Patent: Sep. 15, 2020

(54) **INCREASING PRODUCTIVITY OF *E. COLI* HOST CELLS THAT FUNCTIONALLY EXPRESS P450 ENZYMES**

(71) Applicant: Manus Bio, Inc., Cambridge, MA (US)

(72) Inventors: Jason Donald, Cambridge, MA (US); Christopher Pirie, Cambridge, MA (US); Liwei Li, Cambridge, MA (US); Huey-Ming Mak, Cambridge, MA (US); Srishti Tibrewala, Cambridge, MA (US); Ajikumar Parayil Kumaran, Cambridge, MA (US)

(73) Assignee: MANUS BIO INC., Cambridge, MA (US)

( * ) Notice: Subject to any disclaimer, the term of this patent is extended or adjusted under 35 U.S.C. 154(b) by 0 days.

(21) Appl. No.: 15/754,105

(22) PCT Filed: Aug. 19, 2016

(86) PCT No.: PCT/US2016/047692
§ 371 (c)(1),
(2) Date: Feb. 21, 2018

(87) PCT Pub. No.: WO2017/034942
PCT Pub. Date: Mar. 2, 2017

(65) Prior Publication Data
US 2018/0251738 A1 Sep. 6, 2018

Related U.S. Application Data

(60) Provisional application No. 62/208,166, filed on Aug. 21, 2015.

(51) Int. Cl.
*C12N 15/52* (2006.01)
*C12N 9/02* (2006.01)
*C12P 5/00* (2006.01)
*C12N 9/00* (2006.01)
*C12P 19/56* (2006.01)
*C12N 15/70* (2006.01)

(52) U.S. Cl.
CPC ............ *C12N 9/0079* (2013.01); *C12N 9/00* (2013.01); *C12N 15/52* (2013.01); *C12N 15/70* (2013.01); *C12P 5/007* (2013.01); *C12P 19/56* (2013.01); *C07K 2319/03* (2013.01)

(58) Field of Classification Search
CPC ................ C97K 2319/03; C12N 15/52; C12N 15/8243; C12P 5/007
See application file for complete search history.

(56) References Cited

U.S. PATENT DOCUMENTS

| | | | |
|---|---|---|---|
| 8,097,438 B2 * | 1/2012 | Chang | C12N 15/8243 435/132 |
| 8,512,988 B2 | 8/2013 | Ajikumar et al. | |
| 8,927,241 B2 | 1/2015 | Ajikumar et al. | |
| 9,359,624 B2 | 6/2016 | Ajikumar et al. | |
| 9,404,130 B2 | 8/2016 | Ajikumar et al. | |
| 9,796,980 B2 | 10/2017 | Ajikumar et al. | |
| 9,957,527 B2 | 5/2018 | Ajikumar et al. | |
| 2017/0332673 A1 | 11/2017 | Philippe et al. | |
| 2018/0135081 A1 | 5/2018 | Kumaran et al. | |
| 2018/0251738 A1 | 9/2018 | Donald et al. | |

FOREIGN PATENT DOCUMENTS

WO 2016029187 2/2016

OTHER PUBLICATIONS

Ajikkumar, et al., "Isoprenoid Pathway Optimization for Taxol Precursor Overproduction in *Escherichia coli*", Scinece, 2010, vol. 1, No. 330(6000), pp. 1-11.
Chang, et al., "Engineering *Escherichia coli* for production of functionalized terpenoids using plant P450s", Nature, 2007, Chemical Biology, vol. 3, No. 5, pp. 274-277.
Leonard, et al., "Functional expression of a P450 flavonoid hydroxy lase for the biosynthesis of plant-specific hydroxylated flavonols in *Escherichia coli*", Metabolic Engineering, 2006, vol. 8, pp. 172-181.
International Search Report and Written Opinion, for International Application No. PCT/US2016/047692, dated Oct. 25, 2016, 13 pages.

* cited by examiner

*Primary Examiner* — Karen Cochrane Carlson
(74) *Attorney, Agent, or Firm* — Morgan, Lewis & Bockius LLP

(57) ABSTRACT

The present invention relates to the production of chemical species in bacterial host cells. Particularly, the present invention provides for the production of chemical species in *Escherichia coli* (*E. coli*) host cells that functionally express engineered P450 enzymes.

20 Claims, 14 Drawing Sheets
Specification includes a Sequence Listing.

SEQUENCE LISTING

<160> NUMBER OF SEQ ID NOS: 64

<210> SEQ ID NO 1
<211> LENGTH: 513
<212> TYPE: PRT
<213> ORGANISM: Zingiber zerumbet

<400> SEQUENCE: 1

Met Glu Ala Ile Ser Leu Phe Ser Pro Phe Phe Ile Thr Leu Phe
1               5                   10                  15

Leu Gly Phe Phe Ile Thr Leu Leu Ile Lys Arg Ser Ser Arg Ser Ser
            20                  25                  30

Val His Lys Gln Gln Val Leu Leu Ala Ser Leu Pro Pro Ser Pro Pro
        35                  40                  45

Arg Leu Pro Leu Ile Gly Asn Ile His Gln Leu Val Gly Gly Asn Pro
    50                  55                  60

His Arg Ile Leu Leu Gln Leu Ala Arg Thr His Gly Pro Leu Ile Cys
65                  70                  75                  80

Leu Arg Leu Gly Gln Val Asp Gln Val Val Ala Ser Ser Val Glu Ala
                85                  90                  95

Val Glu Glu Ile Ile Lys Arg His Asp Leu Lys Phe Ala Asp Arg Pro
            100                 105                 110

Arg Asp Leu Thr Phe Ser Arg Ile Phe Phe Tyr Asp Gly Asn Ala Val
        115                 120                 125

Val Met Thr Pro Tyr Gly Gly Glu Trp Lys Gln Met Arg Lys Ile Tyr
    130                 135                 140

Ala Met Glu Leu Leu Asn Ser Arg Arg Val Lys Ser Phe Ala Ala Ile
145                 150                 155                 160

Arg Glu Asp Val Ala Arg Lys Leu Thr Gly Glu Ile Ala His Lys Ala
                165                 170                 175

Phe Ala Gln Thr Pro Val Ile Asn Leu Ser Glu Met Val Met Ser Met
            180                 185                 190

Ile Asn Ala Ile Val Ile Arg Val Ala Phe Gly Asp Lys Cys Lys Gln
        195                 200                 205

Gln Ala Tyr Phe Leu His Leu Val Lys Glu Ala Met Ser Tyr Val Ser
    210                 215                 220

Ser Phe Ser Val Ala Asp Met Tyr Pro Ser Leu Lys Phe Leu Asp Thr
225                 230                 235                 240

Leu Thr Gly Leu Lys Ser Lys Leu Glu Gly Val His Gly Lys Leu Asp
                245                 250                 255

Lys Val Phe Asp Glu Ile Ile Ala Gln Arg Gln Ala Ala Leu Ala Ala
            260                 265                 270

```
Glu Gln Ala Glu Glu Asp Leu Ile Ile Asp Val Leu Leu Lys Leu Lys
            275                 280                 285
Asp Glu Gly Asn Gln Glu Phe Pro Ile Thr Tyr Thr Ser Val Lys Ala
        290                 295                 300
Ile Val Met Glu Ile Phe Leu Ala Gly Thr Glu Thr Ser Ser Ser Val
305                 310                 315                 320
Ile Asp Trp Val Met Ser Glu Leu Ile Lys Asn Pro Lys Ala Met Glu
                325                 330                 335
Lys Val Gln Lys Glu Met Arg Glu Ala Met Gln Gly Lys Thr Lys Leu
            340                 345                 350
Glu Glu Ser Asp Ile Pro Lys Phe Ser Tyr Leu Asn Leu Val Ile Lys
        355                 360                 365
Glu Thr Leu Arg Leu His Pro Pro Gly Pro Leu Leu Phe Pro Arg Glu
    370                 375                 380
Cys Arg Glu Thr Cys Glu Val Met Gly Tyr Arg Val Pro Ala Gly Ala
385                 390                 395                 400
Arg Leu Leu Ile Asn Ala Phe Ala Leu Ser Arg Asp Glu Lys Tyr Trp
                405                 410                 415
Gly Ser Asp Ala Glu Ser Phe Lys Pro Glu Arg Phe Glu Gly Ile Ser
            420                 425                 430
Val Asp Phe Lys Gly Ser Asn Phe Glu Phe Met Pro Phe Gly Ala Gly
        435                 440                 445
Arg Arg Ile Cys Pro Gly Met Thr Phe Gly Ile Ser Ser Val Glu Val
    450                 455                 460
Ala Leu Ala His Leu Leu Phe His Phe Asp Trp Gln Leu Pro Gln Gly
465                 470                 475                 480
Met Lys Ile Glu Asp Leu Asp Met Met Glu Val Ser Gly Met Ser Ala
                485                 490                 495
Thr Arg Arg Ser Pro Leu Leu Val Leu Ala Lys Leu Ile Ile Pro Leu
            500                 505                 510
Pro

<210> SEQ ID NO 2
<211> LENGTH: 496
<212> TYPE: PRT
<213> ORGANISM: Barnadesia spinosa

<400> SEQUENCE: 2

Met Glu Leu Thr Leu Thr Thr Ser Leu Gly Leu Ala Val Phe Val Phe
1               5                   10                  15
Ile Leu Phe Lys Leu Leu Thr Gly Ser Lys Ser Thr Lys Asn Ser Leu
                20                  25                  30
Pro Glu Ala Trp Arg Leu Pro Ile Ile Gly His Met His His Leu Val
            35                  40                  45
Gly Thr Leu Pro His Arg Gly Val Thr Asp Met Ala Arg Lys Tyr Gly
        50                  55                  60
Ser Leu Met His Leu Gln Leu Gly Glu Val Ser Thr Ile Val Val Ser
65                  70                  75                  80
Ser Pro Arg Trp Ala Lys Glu Val Leu Thr Thr Tyr Asp Ile Thr Phe
                85                  90                  95
Ala Asn Arg Pro Glu Thr Leu Thr Gly Glu Ile Val Ala Tyr His Asn
            100                 105                 110
Thr Asp Ile Val Leu Ser Pro Tyr Gly Glu Tyr Trp Arg Gln Leu Arg
        115                 120                 125
```

```
Lys Leu Cys Thr Leu Glu Leu Leu Ser Ala Lys Lys Val Lys Ser Phe
    130                 135                 140

Gln Ser Leu Arg Glu Glu Glu Cys Trp Asn Leu Val Lys Glu Val Arg
145                 150                 155                 160

Ser Ser Gly Ser Gly Ser Pro Val Asp Leu Ser Glu Ser Ile Phe Lys
                165                 170                 175

Leu Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Leu Thr
        195                 200                 205

Gly Gly Phe Asp Val Ala Asp Ile Phe Pro Ser Lys Lys Ile Leu His
    210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270

Ser Ala Glu Leu Pro Leu Thr Ser Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
    450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495

<210> SEQ ID NO 3
<211> LENGTH: 502
<212> TYPE: PRT
<213> ORGANISM: Hyoscyamus muticus

<400> SEQUENCE: 3

Met Gln Phe Phe Ser Leu Val Ser Ile Phe Leu Phe Leu Ser Phe Leu
1               5                   10                  15
```

```
Phe Leu Leu Arg Lys Trp Lys Asn Ser Asn Ser Gln Ser Lys Lys Leu
             20                  25                  30

Pro Pro Gly Pro Trp Lys Leu Pro Leu Leu Gly Ser Met Leu His Met
         35                  40                  45

Val Gly Gly Leu Pro His His Val Leu Arg Asp Leu Ala Lys Lys Tyr
 50                  55                  60

Gly Pro Leu Met His Leu Gln Leu Gly Glu Val Ser Ala Val Val Val
 65                  70                  75                  80

Thr Ser Pro Asp Met Ala Lys Glu Val Leu Lys Thr His Asp Ile Ala
                 85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
130                 135                 140

Phe Ser Ser Ile Arg Arg Asp Glu Val Leu Arg Leu Val Asn Phe Val
145                 150                 155                 160

Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Glu Thr Phe Ile Gln Leu Ile Lys Glu Val Ile Gly Leu Ala
        195                 200                 205

Gly Gly Phe Asp Val Ala Asp Ile Phe Pro Ser Leu Lys Phe Leu His
210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Gly Glu Asp Leu Ile Asp Val
            260                 265                 270

Leu Leu Arg Leu Met Asn Asp Gly Gly Leu Gln Phe Pro Ile Thr Asn
        275                 280                 285

Asp Asn Ile Lys Ala Ile Ile Phe Asp Met Phe Ala Ala Gly Thr Glu
290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Glu Thr Glu Ile Asn Gly Tyr Thr
370                 375                 380

Ile Pro Val Lys Thr Lys Val Met Val Asn Val Trp Ala Leu Gly Arg
385                 390                 395                 400

Asp Pro Lys Tyr Trp Asp Asp Ala Asp Asn Phe Lys Pro Glu Arg Phe
                405                 410                 415

Glu Gln Cys Ser Val Asp Phe Ile Gly Asn Asn Phe Lys Tyr Leu Pro
            420                 425                 430
```

Phe Gly Gly Gly Arg Arg Ile Cys Pro Gly Ile Ser Phe Gly Leu Ala
            435                 440                 445

Asn Val Tyr Leu Pro Leu Ala Gln Leu Leu Tyr His Phe Asp Trp Lys
450                 455                 460

Leu Pro Thr Gly Met Glu Pro Lys Asp Leu Asp Leu Thr Glu Leu Val
465                 470                 475                 480

Gly Val Thr Ala Ala Arg Lys Ser Asp Leu Met Leu Val Ala Thr Pro
                485                 490                 495

Tyr Gln Pro Ser Arg Glu
            500

<210> SEQ ID NO 4
<211> LENGTH: 488
<212> TYPE: PRT
<213> ORGANISM: Lactuca sativa

<400> SEQUENCE: 4

Met Glu Leu Ser Ile Thr Thr Ser Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45

Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
    130                 135                 140

Gln Ser Ile Arg Glu Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
                165                 170                 175

Met Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
                245                 250                 255

Ser Lys Ala Asn Glu Thr Leu Leu Asp Val Leu Leu Arg Leu Lys Asp
            260                 265                 270

Ser Ala Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
    290                 295                 300

```
Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Lys Ile Gln Glu Glu
                325                 330                 335

Asp Ile Gln Asp Leu Ala Tyr Leu Asn Leu Val Ile Arg Glu Thr Leu
            340                 345                 350

Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
    450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485

<210> SEQ ID NO 5
<211> LENGTH: 504
<212> TYPE: PRT
<213> ORGANISM: Nicotiani tabacum

<400> SEQUENCE: 5

Met Gln Phe Phe Ser Leu Val Ser Ile Phe Leu Phe Leu Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Ile Pro Ile Leu Gly Ser Met Leu His Met
        35                  40                  45

Ile Gly Gly Glu Pro His His Val Leu Arg Asp Leu Ala Lys Lys Tyr
    50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
145                 150                 155                 160

Arg Ser Asp Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
```

```
                180             185             190
Leu Lys Gly Gln Asp Ile Phe Ala Lys Lys Ile Arg Glu Val Ile Gly
            195                 200                 205

Leu Ala Glu Gly Phe Asp Val Val Asp Ile Phe Pro Thr Tyr Lys Phe
210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
            245                 250                 255

Leu Ala Ala Gly Lys Ser Asn Gly Ala Leu Gly Gly Glu Asp Leu Ile
            260                 265                 270

Asp Val Leu Arg Leu Met Asn Asp Thr Ser Leu Gln Phe Pro Ile
            275                 280                 285

Thr Asn Asp Asn Ile Lys Ala Val Ile Val Asp Met Phe Ala Ala Gly
            290                 295                 300

Thr Glu Thr Ser Ser Thr Thr Thr Val Trp Ala Met Ala Glu Met Met
305                 310                 315                 320

Lys Asn Pro Ser Val Phe Thr Lys Ala Gln Ala Glu Val Arg Glu Ala
            325                 330                 335

Phe Arg Asp Lys Val Ser Phe Asp Glu Asn Asp Val Glu Glu Leu Lys
            340                 345                 350

Tyr Leu Lys Leu Val Ile Lys Glu Thr Leu Arg Leu His Pro Pro Ser
            355                 360                 365

Pro Leu Leu Val Pro Arg Glu Cys Arg Glu Asp Thr Asp Ile Asn Gly
            370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
            405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
            435                 440                 445

Leu Ala Asn Leu Tyr Leu Pro Leu Ala Gln Leu Leu Tyr His Phe Asp
            450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Gly Leu Tyr Leu Asn Ala
            485                 490                 495

Thr Pro Tyr Gln Pro Ser Arg Glu
            500

<210> SEQ ID NO 6
<211> LENGTH: 522
<212> TYPE: PRT
<213> ORGANISM: Citrus x paradisi

<400> SEQUENCE: 6

Met Glu Leu Pro Leu Lys Ser Ile Ala Leu Thr Ile Val Ile Val Thr
1               5                   10                  15

Val Leu Thr Trp Ala Trp Arg Val Leu Asn Trp Val Trp Leu Arg Pro
            20                  25                  30

Lys Lys Leu Glu Lys Phe Leu Arg Gln Gln Gly Leu Lys Gly Asn Ser
            35                  40                  45
```

```
Tyr Arg Leu Leu Phe Gly Asp Leu Lys Glu Asn Ser Ile Glu Leu Lys
    50                  55                  60

Glu Ala Lys Ala Arg Pro Leu Ser Leu Asp Asp Ile Ala Ile Arg
65                  70                  75                  80

Val Asn Pro Phe Leu His Lys Leu Val Asn Asp Tyr Gly Lys Asn Ser
                    85                  90                  95

Phe Met Trp Phe Gly Pro Thr Pro Arg Val Asn Ile Met Asn Pro Asp
                100                 105                 110

Gln Ile Lys Ala Ile Phe Thr Lys Ile Asn Asp Phe Gln Lys Val Asn
            115                 120                 125

Ser Ile Pro Leu Ala Arg Leu Leu Ile Val Gly Leu Ala Thr Leu Glu
130                 135                 140

Gly Glu Lys Trp Ala Lys His Arg Lys Leu Ile Asn Pro Ala Phe His
145                 150                 155                 160

Gln Glu Lys Leu Lys Leu Met Leu Pro Ala Phe Tyr Leu Ser Cys Ile
                165                 170                 175

Glu Ile Ile Thr Lys Trp Glu Lys Gln Met Ser Val Glu Gly Ser Ser
            180                 185                 190

Glu Leu Asp Val Trp Pro Tyr Leu Ala Asn Leu Thr Ser Asp Val Ile
        195                 200                 205

Ser Arg Thr Ala Phe Gly Ser Ser Tyr Glu Glu Gly Arg Arg Ile Phe
210                 215                 220

Gln Leu Gln Ala Glu Leu Ala Glu Leu Thr Met Gln Val Phe Arg Ser
225                 230                 235                 240

Val His Ile Pro Gly Trp Arg Phe Leu Pro Thr Lys Arg Asn Arg Arg
                245                 250                 255

Met Lys Glu Ile Asp Lys Glu Ile Arg Ala Ser Leu Met Gly Ile Ile
            260                 265                 270

Lys Asn Arg Glu Lys Ala Met Arg Ala Gly Glu Ala Ala Asn Asn Asp
        275                 280                 285

Leu Leu Gly Ile Leu Met Glu Thr Ser Phe Arg Glu Ile Glu Glu His
290                 295                 300

Gly Asn Asn Lys Asn Val Gly Phe Ser Met Asn Asp Val Ile Glu Glu
305                 310                 315                 320

Cys Lys Leu Phe Tyr Phe Ala Gly Gln Glu Thr Thr Ser Val Leu Leu
                325                 330                 335

Asn Trp Thr Met Val Leu Leu Ser Lys His Gln Asp Trp Gln Glu Arg
            340                 345                 350

Ala Arg Gln Glu Val Leu Gln Val Phe Gly Asn Asn Lys Pro Asp Tyr
        355                 360                 365

Asp Gly Leu Asn His Leu Lys Ile Val Gln Met Ile Leu Tyr Glu Val
    370                 375                 380

Leu Arg Leu Tyr Pro Pro Val Thr Val Leu Ser Arg Ala Val Phe Lys
385                 390                 395                 400

Glu Thr Lys Leu Gly Asn Leu Thr Leu Pro Ala Gly Val Gln Ile Gly
                405                 410                 415

Leu Pro Met Ile Leu Val His Gln Asp Pro Glu Leu Trp Gly Asp Asp
            420                 425                 430

Ala Val Glu Phe Lys Pro Glu Arg Phe Ala Glu Gly Ile Ser Lys Ala
        435                 440                 445

Ala Lys Asn Gln Val Ser Tyr Phe Pro Phe Ala Leu Gly Pro Arg Ile
    450                 455                 460

Cys Val Gly Gln Asn Phe Ala Leu Val Glu Ala Lys Met Ala Thr Ala
```

```
            465                 470                 475                 480
Met Ile Leu Gln Asn Tyr Ser Phe Glu Leu Ser Pro Ser Tyr Val His
                    485                 490                 495

Ala Pro Thr Ala Val Pro Thr Leu His Pro Glu Leu Gly Thr Gln Leu
            500                 505                 510

Ile Leu Arg Lys Leu Trp Cys Lys Asn Asn
            515                 520

<210> SEQ ID NO 7
<211> LENGTH: 495
<212> TYPE: PRT
<213> ORGANISM: Artemesia annua

<400> SEQUENCE: 7

Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
                20                  25                  30

Lys Ser Thr Lys Lys Ser Leu Pro Glu Pro Trp Arg Leu Pro Ile Ile
            35                  40                  45

Gly His Met His His Leu Ile Gly Thr Thr Pro His Arg Gly Val Arg
        50                  55                  60

Asp Leu Ala Arg Lys Tyr Gly Ser Leu Met His Leu Gln Leu Gly Glu
65                  70                  75                  80

Val Pro Thr Ile Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
                100                 105                 110

Glu Ile Val Leu Tyr His Asn Thr Asp Val Val Leu Ala Pro Tyr Gly
            115                 120                 125

Glu Tyr Trp Arg Gln Leu Arg Lys Ile Cys Thr Leu Glu Leu Leu Ser
        130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
            210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
            290                 295                 300

Ser Ser Ser Thr Ile Glu Trp Ala Ile Ser Glu Leu Ile Lys Cys Pro
305                 310                 315                 320
```

-continued

Lys Ala Met Glu Lys Val Gln Ala Glu Leu Arg Lys Ala Leu Asn Gly
                325                 330                 335

Lys Glu Lys Ile His Glu Glu Asp Ile Gln Glu Leu Ser Tyr Leu Asn
            340                 345                 350

Met Val Ile Lys Glu Thr Leu Arg Leu His Pro Pro Leu Pro Leu Val
        355                 360                 365

Leu Pro Arg Glu Cys Arg Gln Pro Val Asn Leu Ala Gly Tyr Asn Ile
    370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
            420                 425                 430

Gly Ala Gly Arg Arg Met Cys Pro Gly Ala Ala Leu Gly Leu Ala Asn
        435                 440                 445

Val Gln Leu Pro Leu Ala Asn Ile Leu Tyr His Phe Asn Trp Lys Leu
    450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495

<210> SEQ ID NO 8
<211> LENGTH: 509
<212> TYPE: PRT
<213> ORGANISM: Arabidopsis thaliana

<400> SEQUENCE: 8

Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
            245                 250                 255

Ala Arg Ile Gln Gln Lys His Lys Arg Arg Leu Ala Val Met Asn Ala
        260                 265                 270

Leu Ile Gln Asp Arg Leu Lys Gln Asn Gly Ser Glu Ser Asp Asp Asp
    275                 280                 285

Cys Tyr Leu Asn Phe Leu Met Ser Glu Ala Lys Thr Leu Thr Lys Glu
290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
            325                 330                 335

Ser Val Gln Asp Arg Leu Cys Lys Glu Ile Gln Asn Val Cys Gly Gly
        340                 345                 350

Glu Lys Phe Lys Glu Glu Gln Leu Ser Gln Val Pro Tyr Leu Asn Gly
    355                 360                 365

Val Phe His Glu Thr Leu Arg Lys Tyr Ser Pro Ala Pro Leu Val Pro
370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
            405                 410                 415

Lys Arg Trp Glu Arg Pro Glu Asp Trp Trp Pro Glu Arg Phe Leu Asp
        420                 425                 430

Asp Gly Lys Tyr Glu Thr Ser Asp Leu His Lys Thr Met Ala Phe Gly
    435                 440                 445

Ala Gly Lys Arg Val Cys Ala Gly Ala Leu Gln Ala Ser Leu Met Ala
450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
            485                 490                 495

Leu Tyr Pro Leu Met Ala Ile Ile Asn Pro Arg Arg Ser
        500                 505

<210> SEQ ID NO 9
<211> LENGTH: 513
<212> TYPE: PRT
<213> ORGANISM: Stevia rebaudiana

<400> SEQUENCE: 9

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr

```
            65                  70                  75                  80
Tyr Gly Pro Ile Tyr Ser Ile Lys Thr Gly Ala Thr Ser Met Val Val
                    85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
                115                 120                 125

Asp Lys Thr Met Val Ala Met Ser Asp Tyr Asp Tyr His Lys Thr
        130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                        165                 170                 175

Leu His Glu Phe Val Lys Asn Asn Pro Glu Gln Glu Val Asp Leu
                180                 185                 190

Arg Lys Ile Phe Gln Ser Glu Leu Phe Gly Leu Ala Met Arg Gln Ala
                195                 200                 205

Leu Gly Lys Asp Val Glu Ser Leu Tyr Val Glu Asp Leu Lys Ile Thr
        210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
                260                 265                 270

Arg Glu Ala Val Met Lys Ser Leu Ile Lys Glu His Lys Lys Arg Ile
                275                 280                 285

Ala Ser Gly Glu Lys Leu Asn Ser Tyr Ile Asp Tyr Leu Leu Ser Glu
        290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                    325                 330                 335

Tyr Glu Leu Ala Lys Asn Pro Lys Leu Gln Asp Arg Leu Tyr Arg Asp
                340                 345                 350

Ile Lys Ser Val Cys Gly Ser Glu Lys Ile Thr Glu Glu His Leu Ser
                355                 360                 365

Gln Leu Pro Tyr Ile Thr Ala Ile Phe His Glu Thr Leu Arg Arg His
        370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
                420                 425                 430

Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
        450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495
```

Leu Thr Thr Gln Met Leu Arg Pro Leu Arg Ala Ile Ile Lys Pro Arg
            500                 505                 510
Ile

<210> SEQ ID NO 10
<211> LENGTH: 546
<212> TYPE: PRT
<213> ORGANISM: Physcomitrella patens

<400> SEQUENCE: 10

Met Ala Lys His Leu Ala Thr Gln Leu Leu Gln Gln Trp Asn Glu Ala
1               5                   10                  15

Leu Lys Thr Met Pro Pro Gly Phe Arg Thr Ala Gly Lys Ile Leu Val
            20                  25                  30

Trp Glu Glu Leu Ala Ser Asn Lys Val Leu Ile Thr Ile Ala Leu Ala
        35                  40                  45

Trp Val Leu Leu Phe Val Ala Arg Thr Cys Leu Arg Asn Lys Lys Arg
    50                  55                  60

Leu Pro Pro Ala Ile Pro Gly Gly Leu Pro Val Leu Gly Asn Leu Leu
65                  70                  75                  80

Gln Leu Thr Glu Lys Lys Pro His Arg Thr Phe Thr Ala Trp Ser Lys
                85                  90                  95

Glu His Gly Pro Ile Phe Thr Ile Lys Val Gly Ser Val Pro Gln Ala
            100                 105                 110

Val Val Asn Asn Ser Glu Ile Ala Lys Glu Val Leu Val Thr Lys Phe
        115                 120                 125

Ala Ser Ile Ser Lys Arg Gln Met Pro Met Ala Leu Arg Val Leu Thr
    130                 135                 140

Arg Asp Lys Thr Met Val Ala Met Ser Asp Tyr Gly Glu Glu His Arg
145                 150                 155                 160

Met Leu Lys Lys Leu Val Met Thr Asn Leu Leu Gly Pro Thr Thr Gln
                165                 170                 175

Asn Lys Asn Arg Ser Leu Arg Asp Asp Ala Leu Ile Gly Met Ile Glu
            180                 185                 190

Gly Val Leu Ala Glu Leu Lys Ala Ser Pro Thr Ser Pro Lys Val Val
        195                 200                 205

Asn Val Arg Asp Tyr Val Gln Arg Ser Leu Phe Pro Phe Ala Leu Gln
    210                 215                 220

Gln Val Phe Gly Tyr Ile Pro Asp Gln Val Glu Val Leu Glu Leu Gly
225                 230                 235                 240

Thr Cys Val Ser Thr Trp Asp Met Phe Asp Ala Leu Val Val Ala Pro
                245                 250                 255

Leu Ser Ala Val Ile Asn Val Asp Trp Arg Asp Phe Phe Pro Ala Leu
            260                 265                 270

Arg Trp Ile Pro Asn Arg Ser Val Glu Asp Leu Val Arg Thr Val Asp
        275                 280                 285

Phe Lys Arg Asn Ser Ile Met Lys Ala Leu Ile Arg Ala Gln Arg Met
    290                 295                 300

Arg Leu Ala Asn Leu Lys Glu Pro Pro Arg Cys Tyr Ala Asp Ile Ala
305                 310                 315                 320

Leu Thr Glu Ala Thr His Leu Thr Glu Lys Gln Leu Glu Met Ser Leu
                325                 330                 335

Trp Glu Pro Ile Ile Glu Ser Ala Asp Thr Thr Leu Val Thr Ser Glu
            340                 345                 350

```
Trp Ala Met Tyr Glu Ile Ala Lys Asn Pro Asp Cys Gln Asp Arg Leu
            355                 360                 365

Tyr Arg Glu Ile Val Ser Val Ala Gly Thr Glu Arg Met Val Thr Glu
    370                 375                 380

Asp Asp Leu Pro Asn Met Pro Tyr Leu Gly Ala Ile Ile Lys Glu Thr
385                 390                 395                 400

Leu Arg Lys Tyr Thr Pro Val Pro Leu Ile Pro Ser Arg Phe Val Glu
                405                 410                 415

Glu Asp Ile Thr Leu Gly Gly Tyr Asp Ile Pro Lys Gly Tyr Gln Ile
            420                 425                 430

Leu Val Asn Leu Phe Ala Ile Ala Asn Asp Pro Ala Val Trp Ser Asn
            435                 440                 445

Pro Glu Lys Trp Asp Pro Glu Arg Met Leu Ala Asn Lys Lys Val Asp
        450                 455                 460

Met Gly Phe Arg Asp Phe Ser Leu Met Pro Phe Gly Ala Gly Lys Arg
465                 470                 475                 480

Met Cys Ala Gly Ile Thr Gln Ala Met Phe Ile Ile Pro Met Asn Val
                485                 490                 495

Ala Ala Leu Val Gln His Cys Glu Trp Arg Leu Ser Pro Gln Glu Ile
            500                 505                 510

Ser Asn Ile Asn Asn Lys Ile Glu Asp Val Val Tyr Leu Thr Thr His
        515                 520                 525

Lys Leu Ser Pro Leu Ser Cys Glu Ala Thr Pro Arg Ile Ser His Arg
        530                 535                 540

Leu Pro
545

<210> SEQ ID NO 11
<211> LENGTH: 1049
<212> TYPE: PRT
<213> ORGANISM: Bacillus megaterium

<400> SEQUENCE: 11

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
```

```
                165                 170                 175
Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Ala Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590
```

```
Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005
```

```
Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 12
<211> LENGTH: 396
<212> TYPE: PRT
<213> ORGANISM: Pleurotus sapidus

<400> SEQUENCE: 12

Met Arg Tyr Gly Cys Ala Ala Val Ala Leu Phe Tyr Leu Thr Ala Met
  1               5                  10                  15

Gly Lys Leu His Pro Leu Ala Ile Ile Pro Asp Tyr Lys Gly Ser Met
             20                  25                  30

Ala Ala Ser Val Thr Ile Phe Asn Lys Arg Thr Asn Pro Leu Asp Ile
         35                  40                  45

Ser Val Asn Gln Ala Asn Asp Trp Pro Trp Arg Tyr Ala Lys Thr Cys
 50                  55                  60

Val Leu Ser Ser Asp Trp Ala Leu His Glu Met Ile Ile His Leu Asn
 65                  70                  75                  80

Asn Thr His Leu Val Glu Glu Ala Val Ile Val Ala Ala Gln Arg Lys
                 85                  90                  95

Leu Ser Pro Ser His Ile Val Phe Arg Leu Leu Glu Pro His Trp Val
            100                 105                 110

Val Thr Leu Ser Leu Asn Ala Leu Ala Arg Ser Val Leu Ile Pro Glu
        115                 120                 125

Val Ile Val Pro Ile Ala Gly Phe Ser Ala Pro His Ile Phe Gln Phe
    130                 135                 140

Ile Arg Glu Ser Phe Thr Asn Phe Asp Trp Lys Ser Leu Tyr Val Pro
145                 150                 155                 160

Ala Asp Leu Glu Ser Arg Gly Phe Pro Val Asp Gln Leu Asn Ser Pro
                165                 170                 175

Lys Phe His Asn Tyr Ala Tyr Ala Arg Asp Ile Asn Asp Met Trp Thr
            180                 185                 190

Thr Leu Lys Lys Phe Val Ser Ser Val Leu Gln Asp Ala Gln Tyr Tyr
        195                 200                 205

Pro Asp Asp Ala Ser Val Ala Gly Asp Thr Gln Ile Gln Ala Trp Cys
    210                 215                 220

Asp Glu Met Arg Ser Gly Met Gly Ala Gly Met Thr Asn Phe Pro Glu
225                 230                 235                 240

Ser Ile Thr Thr Val Asp Asp Leu Val Asn Met Val Thr Met Cys Ile
                245                 250                 255

His Ile Ala Ala Pro Gln His Thr Ala Val Asn Tyr Leu Gln Gln Tyr
            260                 265                 270

Tyr Gln Thr Phe Val Ser Asn Lys Pro Ser Ala Leu Phe Ser Pro Leu
        275                 280                 285

Pro Thr Ser Ile Ala Gln Leu Gln Lys Tyr Thr Glu Ser Asp Leu Met
    290                 295                 300

Ala Ala Leu Pro Leu Asn Ala Lys Arg Gln Trp Leu Leu Met Ala Gln
305                 310                 315                 320

Ile Pro Tyr Leu Leu Ser Met Gln Val Gln Glu Asp Glu Asn Ile Val
                325                 330                 335
```

Thr Tyr Ala Ala Asn Ala Ser Thr Asp Lys Asp Pro Ile Ile Ala Ser
            340                 345                 350

Ala Gly Arg Gln Leu Ala Ala Asp Leu Lys Lys Leu Ala Ala Val Phe
            355                 360                 365

Leu Val Asn Ser Ala Gln Leu Asp Asp Gln Asn Thr Pro Tyr Asp Val
370                 375                 380

Leu Ala Pro Glu Gln Leu Ala Asn Ala Ile Val Ile
385                 390                 395

<210> SEQ ID NO 13
<211> LENGTH: 640
<212> TYPE: PRT
<213> ORGANISM: Pleurotus ostreatus

<400> SEQUENCE: 13

Met Ala Pro Thr Met Ser Leu Ser Arg Ser Ala Leu Lys Asn Val His
1               5                   10                  15

Leu Pro Tyr Met Val Gln His Pro Glu Pro Thr Asp Cys Ser Thr Ala
            20                  25                  30

Met Lys His Ala Ala Glu Gly Tyr Asp Arg Ala Arg Gln Met Ile Ala
        35                  40                  45

Phe Leu Phe Asp Ile Leu Asp Tyr Glu Ser Ser Val Pro Gln Lys Phe
    50                  55                  60

Thr Pro Glu Glu Lys Lys Glu Lys Tyr Thr Trp Ser His Ser Asp Lys
65                  70                  75                  80

Phe Pro Pro His Leu Ala Ile Ile Pro Glu Asp Ile Asp Val Pro Ala
                85                  90                  95

Tyr Ile Ile Phe Ser Ile Val Arg Leu Val Gln Thr Leu Ser Ile Met
            100                 105                 110

Ser Gly Ile Gln Cys Asn Glu Arg Leu Ala Pro Gly Pro Glu Gln Asn
        115                 120                 125

Thr Met Glu Lys Leu Thr Lys Trp Asn Ala Glu Arg His Lys Asn Gln
    130                 135                 140

Gly Trp Val Lys Asp Met Phe Asn Glu Pro Asn Ile Gly Leu Arg Asn
145                 150                 155                 160

Asp Trp Tyr Thr Asp Ala Val Phe Ala Gln Gln Phe Thr Gly Pro
                165                 170                 175

Asn Pro Thr Thr Ile Thr Leu Ala Ser Asp Thr Trp Met Lys Ala Phe
            180                 185                 190

Thr Glu Glu Ala Ala Ser Gln Gly Lys Arg Asp Leu Ile Ser Leu Phe
        195                 200                 205

Arg Ser Ala Pro Pro Asn Ser Phe Tyr Val Gln Asp Phe Ser Asp Phe
    210                 215                 220

Arg Ala Arg Met Gly Ala Lys Pro Asp Glu Glu Leu Cys Ala Thr Ser
225                 230                 235                 240

Asp Gly Gly Val Thr Arg Tyr Gly Cys Ala Ala Val Ala Leu Phe Tyr
                245                 250                 255

Leu Pro Pro Thr Gly Glu Leu His Pro Leu Ala Ile Val Pro Asp Tyr
            260                 265                 270

Lys Gly Ser Met Ala Ala Ser Ile Thr Leu Phe Asn Lys Arg Val Asp
        275                 280                 285

Pro Ser Asp Ala Ser Val Asp Gln Ala Asn Asp Trp Pro Trp Arg Tyr
    290                 295                 300

Ala Lys Thr Cys Val Leu Ser Ala Asp Trp Val Leu His Glu Met Ile

```
            305                 310                 315                 320
    Ile His Leu Asn Asn Thr His Leu Val Gln Glu Ala Val Ile Val Ala
                        325                 330                 335

Val Gln Arg Thr Leu Pro Asp Ser His Ile Val Phe Arg Leu Leu Lys
                        340                 345                 350

Pro His Trp Val Val Thr Leu Ser Leu Asn Ala Gln Ala Arg Ser Val
                        355                 360                 365

Leu Ile Pro Glu Val Ile Val Pro Ile Ala Gly Phe Ser Glu Leu Arg
            370                 375                 380

Ile Phe Gln Phe Val Gly His Ala Phe Thr Asn Phe Asp Trp Lys Ala
    385                 390                 395                 400

Leu Tyr Val Pro Thr Asp Leu Glu Phe Arg Gly Phe Pro Leu Asp Arg
                        405                 410                 415

Leu Asp Asp Asp Lys Phe His Asn Tyr Ala Tyr Ala Lys Asp Ile Lys
                        420                 425                 430

Asp Met Trp Met Ala Leu Arg Lys Phe Val Ser Ser Val Leu Lys Asp
                        435                 440                 445

Gly Lys Tyr Tyr Pro Asp Asp Ser Ala Val Ala Ala Asp Ala Gln Ile
            450                 455                 460

Gln Asp Trp Cys Asp Glu Met Arg Ser Glu Lys Gly Ala Gly Met Lys
    465                 470                 475                 480

Lys Phe Pro Glu Ser Ile Ser Thr Leu Asp Asp Leu Ile Asp Met Val
                        485                 490                 495

Thr Met Cys Ile His Ile Ala Ala Pro Gln His Thr Ala Val Asn Tyr
                        500                 505                 510

Leu Gln Gln Tyr Tyr Gln Thr Phe Val Pro Asn Lys Pro Ser Ala Leu
            515                 520                 525

Phe Ser Pro Leu Pro Thr Leu Leu Ser Gln Leu Glu Ser Tyr Thr Glu
            530                 535                 540

Ser Asp Leu Met Ala Ala Leu Pro Leu Gly Ala Lys Gln Glu Trp Leu
    545                 550                 555                 560

Leu Met Ala Gln Val Pro Tyr Leu Leu Ser Lys Glu Val Glu Gln Asp
                        565                 570                 575

Gly Asn Ile Val Thr Tyr Ala Gly Thr Ala Ser Asn Asn Glu Asp Pro
                        580                 585                 590

Ile Ile Ala Ala Ala Gly Lys Glu Leu Ser Ala Asp Leu Val Ile Leu
                        595                 600                 605

Ala Gly Val Phe Leu Lys Asn Ser Glu Lys Leu Asp Asp Gln Asn Thr
            610                 615                 620

Ala Tyr Asn Val Leu Ala Pro Asp Gln Leu Ala Asn Ala Ile Val Ile
    625                 630                 635                 640

<210> SEQ ID NO 14
<211> LENGTH: 495
<212> TYPE: PRT
<213> ORGANISM: Cichorium intybus

<400> SEQUENCE: 14

Met Glu Ile Ser Ile Pro Thr Thr Leu Gly Leu Ala Val Ile Ile Phe
    1               5                   10                  15

Ile Ile Phe Lys Leu Leu Thr Arg Thr Thr Ser Lys Lys Asn Leu Leu
                        20                  25                  30

Pro Glu Pro Trp Arg Leu Pro Ile Ile Gly His Met His His Leu Ile
                        35                  40                  45
```

-continued

```
Gly Thr Met Pro His Arg Gly Val Met Glu Leu Ala Arg Lys His Gly
     50                  55                  60
Ser Leu Met His Leu Gln Leu Gly Glu Val Ser Thr Ile Val Val Ser
 65                  70                  75                  80
Ser Pro Arg Trp Ala Lys Glu Val Leu Thr Thr Tyr Asp Ile Thr Phe
                 85                  90                  95
Ala Asn Arg Pro Glu Thr Leu Thr Gly Glu Ile Val Ala Tyr His Asn
            100                 105                 110
Thr Asp Ile Val Leu Ala Pro Tyr Gly Glu Tyr Trp Arg Gln Leu Arg
        115                 120                 125
Lys Leu Cys Thr Leu Glu Leu Leu Ser Asn Lys Val Lys Ser Phe
130                 135                 140
Gln Ser Leu Arg Glu Glu Cys Trp Asn Leu Val Lys Asp Ile Arg
145                 150                 155                 160
Ser Thr Gly Gln Gly Ser Pro Ile Asn Leu Ser Glu Asn Ile Phe Lys
                165                 170                 175
Met Ile Ala Thr Ile Leu Ser Arg Ala Ala Phe Gly Lys Gly Ile Lys
            180                 185                 190
Asp Gln Met Lys Phe Thr Glu Leu Val Lys Glu Ile Leu Arg Leu Thr
        195                 200                 205
Gly Gly Phe Asp Val Ala Asp Ile Phe Pro Ser Lys Lys Leu Leu His
210                 215                 220
His Leu Ser Gly Lys Arg Ala Lys Leu Thr Asn Ile His Asn Lys Leu
225                 230                 235                 240
Asp Asn Leu Ile Asn Asn Ile Ile Ala Glu His Pro Gly Asn Arg Thr
                245                 250                 255
Ser Ser Ser Gln Glu Thr Leu Leu Asp Val Leu Leu Arg Leu Lys Glu
            260                 265                 270
Ser Ala Glu Phe Pro Leu Thr Ala Asp Asn Val Lys Ala Val Ile Leu
        275                 280                 285
Asp Met Phe Gly Ala Gly Thr Asp Thr Ser Ser Ala Thr Ile Glu Trp
290                 295                 300
Ala Ile Ser Glu Leu Ile Arg Cys Pro Arg Ala Met Glu Lys Val Gln
305                 310                 315                 320
Thr Glu Leu Arg Gln Ala Leu Asn Gly Lys Glu Arg Ile Gln Glu Glu
                325                 330                 335
Asp Leu Gln Glu Leu Asn Tyr Leu Lys Leu Val Ile Lys Glu Thr Leu
            340                 345                 350
Arg Leu His Pro Pro Leu Pro Leu Val Met Pro Arg Glu Cys Arg Glu
        355                 360                 365
Pro Cys Val Leu Gly Gly Tyr Asp Ile Pro Ser Lys Thr Lys Leu Ile
370                 375                 380
Val Asn Val Phe Ala Ile Asn Arg Asp Pro Glu Tyr Trp Lys Asp Ala
385                 390                 395                 400
Glu Thr Phe Met Pro Glu Arg Phe Glu Asn Ser Pro Ile Thr Val Met
                405                 410                 415
Gly Ser Glu Tyr Glu Tyr Leu Pro Phe Gly Ala Gly Arg Arg Met Cys
            420                 425                 430
Pro Gly Ala Ala Leu Gly Leu Ala Asn Val Glu Leu Pro Leu Ala His
        435                 440                 445
Ile Leu Tyr Phe Asn Trp Lys Leu Pro Asn Gly Lys Thr Phe Glu Asp
450                 455                 460
Leu Asp Met Thr Glu Ser Phe Gly Ala Thr Val Gln Arg Lys Thr Glu
```

Leu Leu Leu Val Pro Thr Asp Phe Gln Thr Leu Thr Ala Ser Thr
            485                 490                 495

<210> SEQ ID NO 15
<211> LENGTH: 488
<212> TYPE: PRT
<213> ORGANISM: Helianthus annuus

<400> SEQUENCE: 15

Met Glu Val Ser Leu Thr Thr Ser Ile Ala Leu Ala Thr Ile Val Phe
1               5                   10                  15

Phe Leu Tyr Lys Leu Leu Thr Arg Pro Thr Ser Ser Lys Asn Arg Leu
            20                  25                  30

Pro Glu Pro Trp Arg Leu Pro Ile Ile Gly His Met His His Leu Ile
            35                  40                  45

Gly Thr Met Pro His Arg Gly Val Met Asp Leu Ala Arg Lys Tyr Gly
        50                  55                  60

Ser Leu Met His Leu Gln Leu Gly Glu Val Ser Ala Ile Val Val Ser
65                  70                  75                  80

Ser Pro Lys Trp Ala Lys Glu Ile Leu Thr Thr Tyr Asp Ile Pro Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
130                 135                 140

Gln Ser Leu Arg Glu Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
            180                 185                 190

Asp Gln Lys Gln Phe Thr Glu Ile Val Lys Glu Ile Leu Arg Glu Thr
        195                 200                 205

Gly Gly Phe Asp Val Ala Asp Ile Phe Pro Ser Lys Lys Phe Leu His
210                 215                 220

His Leu Ser Gly Lys Arg Gly Arg Leu Thr Ser Ile His Asn Lys Leu
225                 230                 235                 240

Asp Ser Leu Ile Asn Asn Leu Val Ala Glu His Thr Val Ser Lys Ser
                245                 250                 255

Ser Lys Val Asn Glu Thr Leu Leu Asp Val Leu Leu Arg Leu Lys Asn
            260                 265                 270

Ser Glu Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Arg Ile Lys Glu Glu
                325                 330                 335

Glu Ile Gln Asp Leu Pro Tyr Leu Asn Leu Val Ile Arg Glu Thr Leu
            340                 345                 350

```
Arg Leu His Pro Pro Leu Pro Leu Val Met Pro Arg Glu Cys Arg Gln
        355                 360                 365

Ala Met Asn Leu Ala Gly Tyr Asp Val Ala Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ser Phe Asn Pro Glu Arg Phe Glu Asn Ser Asn Thr Thr Ile Met
                405                 410                 415

Gly Ala Asp Tyr Glu Tyr Leu Pro Phe Gly Ala Gly Arg Arg Met Cys
                420                 425                 430

Pro Gly Ser Ala Leu Gly Leu Ala Asn Val Gln Leu Pro Leu Ala Asn
            435                 440                 445

Ile Leu Tyr Tyr Phe Lys Trp Lys Leu Pro Asn Gly Ala Ser His Asp
        450                 455                 460

Gln Leu Asp Met Thr Glu Ser Phe Gly Ala Thr Val Gln Arg Lys Thr
465                 470                 475                 480

Glu Leu Met Leu Val Pro Ser Phe
                485

<210> SEQ ID NO 16
<211> LENGTH: 425
<212> TYPE: PRT
<213> ORGANISM: Escherichia coli

<400> SEQUENCE: 16

Met Leu Glu Leu Leu Tyr Thr Ala Leu Leu Tyr Leu Ile Gln Pro Leu
1               5                   10                  15

Ile Trp Ile Arg Leu Trp Val Arg Gly Arg Lys Ala Pro Ala Tyr Arg
            20                  25                  30

Lys Arg Trp Gly Glu Arg Tyr Gly Phe Tyr Arg His Pro Leu Lys Pro
        35                  40                  45

Gly Gly Ile Met Leu His Ser Val Ser Val Gly Glu Thr Leu Ala Ala
    50                  55                  60

Ile Pro Leu Val Arg Ala Leu Arg His Arg Tyr Pro Asp Leu Pro Ile
65                  70                  75                  80

Thr Val Thr Thr Met Thr Pro Thr Gly Ser Glu Arg Val Gln Ser Ala
                85                  90                  95

Phe Gly Lys Asp Val Gln His Val Tyr Leu Pro Tyr Asp Leu Pro Asp
            100                 105                 110

Ala Leu Asn Arg Phe Leu Asn Lys Val Asp Pro Lys Leu Val Leu Ile
        115                 120                 125

Met Glu Thr Glu Leu Trp Pro Asn Leu Ile Ala Ala Leu His Lys Arg
    130                 135                 140

Lys Ile Pro Leu Val Ile Ala Asn Ala Arg Leu Ser Ala Arg Ser Ala
145                 150                 155                 160

Ala Gly Tyr Ala Lys Leu Gly Lys Phe Val Arg Arg Leu Leu Arg Arg
                165                 170                 175

Ile Thr Leu Ile Ala Ala Gln Asn Glu Glu Asp Gly Ala Arg Phe Val
            180                 185                 190

Ala Leu Gly Ala Lys Asn Asn Gln Val Thr Val Thr Gly Ser Leu Lys
        195                 200                 205

Phe Asp Ile Ser Val Thr Pro Gln Leu Ala Ala Lys Ala Val Thr Leu
    210                 215                 220

Arg Arg Gln Trp Ala Pro His Arg Pro Val Trp Ile Ala Thr Ser Thr
225                 230                 235                 240
```

```
His Glu Gly Glu Glu Ser Val Val Ile Ala Ala His Gln Ala Leu Leu
                245                 250                 255

Gln Gln Phe Pro Asn Leu Leu Leu Ile Leu Val Pro Arg His Pro Glu
            260                 265                 270

Arg Phe Pro Asp Ala Ile Asn Leu Val Arg Gln Ala Gly Leu Ser Tyr
        275                 280                 285

Ile Thr Arg Ser Ser Gly Glu Val Pro Ser Thr Ser Thr Gln Val Val
    290                 295                 300

Val Gly Asp Thr Met Gly Glu Leu Met Leu Leu Tyr Gly Ile Ala Asp
305                 310                 315                 320

Leu Ala Phe Val Gly Gly Ser Leu Val Glu Arg Gly His Asn Pro
                325                 330                 335

Leu Glu Ala Ala Ala His Ala Ile Pro Val Leu Met Gly Pro His Thr
            340                 345                 350

Phe Asn Phe Lys Asp Ile Cys Ala Arg Leu Glu Gln Ala Ser Gly Leu
        355                 360                 365

Ile Thr Val Thr Asp Ala Thr Thr Leu Ala Lys Glu Val Ser Ser Leu
    370                 375                 380

Leu Thr Asp Ala Asp Tyr Arg Ser Phe Tyr Gly Arg His Ala Val Glu
385                 390                 395                 400

Val Leu Tyr Gln Asn Gln Gly Ala Leu Gln Arg Leu Leu Gln Leu Leu
                405                 410                 415

Glu Pro Tyr Leu Pro Pro Lys Thr His
            420                 425

<210> SEQ ID NO 17
<211> LENGTH: 66
<212> TYPE: PRT
<213> ORGANISM: Escherichia coli

<400> SEQUENCE: 17

Met Asp Trp Leu Ala Lys Tyr Trp Trp Ile Leu Val Ile Val Phe Leu
1               5                   10                  15

Val Gly Val Leu Leu Asn Val Ile Lys Asp Leu Lys Arg Val Asp His
            20                  25                  30

Lys Lys Phe Leu Ala Asn Lys Pro Glu Leu Pro Pro His Arg Asp Phe
        35                  40                  45

Asn Asp Lys Trp Asp Asp Asp Asp Trp Pro Lys Lys Asp Gln Pro
    50                  55                  60

Lys Lys
65

<210> SEQ ID NO 18
<211> LENGTH: 132
<212> TYPE: PRT
<213> ORGANISM: Escherichia coli

<400> SEQUENCE: 18

Met Thr Trp Glu Tyr Ala Leu Ile Gly Leu Val Val Gly Ile Ile
1               5                   10                  15

Gly Ala Val Ala Met Arg Phe Gly Asn Arg Lys Leu Arg Gln Gln Gln
            20                  25                  30

Ala Leu Gln Tyr Glu Leu Glu Lys Asn Lys Ala Glu Leu Asp Glu Tyr
        35                  40                  45

Arg Glu Glu Leu Val Ser His Phe Ala Arg Ser Ala Glu Leu Leu Asp
    50                  55                  60
```

```
Thr Met Ala His Asp Tyr Arg Gln Leu Tyr Gln His Met Ala Lys Ser
 65                  70                  75                  80

Ser Ser Ser Leu Leu Pro Glu Leu Ser Ala Glu Ala Asn Pro Phe Arg
                 85                  90                  95

Asn Arg Leu Ala Glu Ser Glu Ala Ser Asn Asp Gln Ala Pro Val Gln
                100                 105                 110

Met Pro Arg Asp Tyr Ser Glu Gly Ala Ser Gly Leu Leu Arg Thr Gly
            115                 120                 125

Ala Lys Arg Asp
            130

<210> SEQ ID NO 19
<211> LENGTH: 294
<212> TYPE: PRT
<213> ORGANISM: Escherichia coli

<400> SEQUENCE: 19

Met Lys Pro Phe Leu Arg Trp Cys Phe Val Ala Thr Ala Leu Thr Leu
  1               5                  10                  15

Ala Gly Cys Ser Asn Thr Ser Trp Arg Lys Ser Glu Val Leu Ala Val
                 20                  25                  30

Pro Leu Gln Pro Thr Leu Gln Gln Glu Val Ile Leu Ala Arg Met Glu
                 35                  40                  45

Gln Ile Leu Ala Ser Arg Ala Leu Thr Asp Asp Glu Arg Ala Gln Leu
 50                  55                  60

Leu Tyr Glu Arg Gly Val Leu Tyr Asp Ser Leu Gly Leu Arg Ala Leu
 65                  70                  75                  80

Ala Arg Asn Asp Phe Ser Gln Ala Leu Ala Ile Arg Pro Asp Met Pro
                 85                  90                  95

Glu Val Phe Asn Tyr Leu Gly Ile Tyr Leu Thr Gln Ala Gly Asn Phe
                100                 105                 110

Asp Ala Ala Tyr Glu Ala Phe Asp Ser Val Leu Glu Leu Asp Pro Thr
            115                 120                 125

Tyr Asn Tyr Ala His Leu Asn Arg Gly Ile Ala Leu Tyr Tyr Gly Gly
            130                 135                 140

Arg Asp Lys Leu Ala Gln Asp Leu Leu Ala Phe Tyr Gln Asp Asp
145                 150                 155                 160

Pro Asn Asp Pro Phe Arg Ser Leu Trp Leu Tyr Leu Ala Glu Gln Lys
                165                 170                 175

Leu Asp Glu Lys Gln Ala Lys Glu Val Leu Lys Gln His Phe Glu Lys
            180                 185                 190

Ser Asp Lys Glu Gln Trp Gly Trp Asn Ile Val Glu Phe Tyr Leu Gly
            195                 200                 205

Asn Ile Ser Glu Gln Thr Leu Met Glu Arg Leu Lys Ala Asp Ala Thr
210                 215                 220

Asp Asn Thr Ser Leu Ala Glu His Leu Ser Glu Thr Asn Phe Tyr Leu
225                 230                 235                 240

Gly Lys Tyr Tyr Leu Ser Leu Gly Asp Leu Asp Ser Ala Thr Ala Leu
                245                 250                 255

Phe Lys Leu Ala Val Ala Asn Asn Val His Asn Phe Val Glu His Arg
                260                 265                 270

Tyr Ala Leu Leu Glu Leu Ser Leu Leu Gly Gln Asp Gln Asp Leu
            275                 280                 285

Ala Glu Ser Asp Gln Gln
```

<210> SEQ ID NO 20
<211> LENGTH: 119
<212> TYPE: PRT
<213> ORGANISM: Escherichia coli

<400> SEQUENCE: 20

Met Ser Lys Pro Pro Leu Phe Phe Ile Val Ile Ile Gly Leu Ile Val
1               5                   10                  15

Val Ala Ala Ser Phe Arg Phe Met Gln Gln Arg Arg Glu Lys Ala Asp
            20                  25                  30

Asn Asp Met Ala Pro Leu Gln Gln Lys Leu Val Val Ser Asn Lys
        35                  40                  45

Arg Glu Lys Pro Ile Asn Asp Arg Arg Ser Arg Gln Gln Val Thr
    50                  55                  60

Pro Ala Gly Thr Ser Ile Arg Tyr Glu Ala Ser Phe Lys Pro Gln Ser
65              70                  75                  80

Gly Gly Met Glu Gln Thr Phe Arg Leu Asp Ala Gln Tyr His Ala
            85                  90                  95

Leu Thr Val Gly Asp Lys Gly Thr Leu Ser Tyr Lys Gly Thr Arg Phe
            100                 105                 110

Val Ser Phe Val Gly Glu Gln
            115

<210> SEQ ID NO 21
<211> LENGTH: 328
<212> TYPE: PRT
<213> ORGANISM: Escherichia coli

<400> SEQUENCE: 21

Met Met Gln Asp Leu Arg Leu Ile Leu Ile Ile Val Gly Ala Ile Ala
1               5                   10                  15

Ile Ile Ala Leu Leu Val His Gly Phe Trp Thr Ser Arg Lys Glu Arg
            20                  25                  30

Ser Ser Met Phe Arg Asp Arg Pro Leu Lys Arg Met Lys Ser Lys Arg
            35                  40                  45

Asp Asp Asp Ser Tyr Asp Glu Asp Val Glu Asp Asp Glu Gly Val Gly
    50                  55                  60

Glu Val Arg Val His Arg Val Asn His Ala Pro Ala Asn Ala Gln Glu
65              70                  75                  80

His Glu Ala Ala Arg Pro Ser Pro Gln His Gln Tyr Gln Pro Pro Tyr
            85                  90                  95

Ala Ser Ala Gln Pro Arg Gln Pro Val Gln Gln Pro Glu Ala Gln
            100                 105                 110

Val Pro Pro Gln His Ala Pro His Pro Ala Gln Pro Val Gln Gln Pro
            115                 120                 125

Ala Tyr Gln Pro Gln Pro Glu Gln Pro Leu Gln Pro Val Ser Pro
    130                 135                 140

Gln Val Ala Pro Ala Pro Gln Pro Val His Ser Ala Pro Gln Pro Ala
145             150                 155                 160

Gln Gln Ala Phe Gln Pro Ala Glu Pro Val Ala Ala Pro Gln Pro Glu
            165                 170                 175

Pro Val Ala Glu Pro Ala Pro Val Met Asp Lys Pro Lys Arg Lys Glu
            180                 185                 190

Ala Val Ile Ile Met Asn Val Ala Ala His His Gly Ser Glu Leu Asn

```
                195                 200                 205
Gly Glu Leu Leu Leu Asn Ser Ile Gln Gln Ala Gly Phe Ile Phe Gly
    210                 215                 220

Asp Met Asn Ile Tyr His Arg His Leu Ser Pro Asp Gly Ser Gly Pro
225                 230                 235                 240

Ala Leu Phe Ser Leu Ala Asn Met Val Lys Pro Gly Thr Phe Asp Pro
                245                 250                 255

Glu Met Lys Asp Phe Thr Thr Pro Gly Val Thr Ile Phe Met Gln Val
            260                 265                 270

Pro Ser Tyr Gly Asp Glu Leu Gln Asn Phe Lys Leu Met Leu Gln Ser
        275                 280                 285

Ala Gln His Ile Ala Asp Glu Val Gly Gly Val Val Leu Asp Asp Gln
    290                 295                 300

Arg Arg Met Met Thr Pro Gln Lys Leu Arg Glu Tyr Gln Asp Ile Ile
305                 310                 315                 320

Arg Glu Val Lys Asp Ala Asn Ala
                325

<210> SEQ ID NO 22
<211> LENGTH: 507
<212> TYPE: PRT
<213> ORGANISM: Escherichia coli

<400> SEQUENCE: 22

Met Arg Asn Thr Leu Ile Pro Ile Leu Val Ala Ile Cys Leu Phe Ile
1               5                   10                  15

Thr Gly Val Ala Ile Leu Asn Ile Gln Leu Trp Tyr Ser Ala Lys Ala
                20                  25                  30

Glu Tyr Leu Ala Gly Ala Arg Tyr Ala Ala Asn Asn Ile Asn His Ile
            35                  40                  45

Leu Glu Glu Ala Ser Gln Ala Thr Gln Thr Ala Val Asn Ile Ala Gly
        50                  55                  60

Lys Glu Cys Asn Leu Glu Glu Gln Tyr Gln Leu Gly Thr Glu Ala Ala
65                  70                  75                  80

Leu Lys Pro His Leu Arg Thr Ile Ile Leu Lys Gln Gly Ile Val
                85                  90                  95

Trp Cys Thr Ser Leu Pro Gly Asn Arg Val Leu Leu Ser Arg Ile Pro
            100                 105                 110

Val Phe Pro Asp Ser Asn Leu Leu Leu Ala Pro Ala Ile Asp Thr Val
        115                 120                 125

Asn Arg Leu Pro Ile Leu Leu Tyr Gln Asn Gln Phe Ala Asp Thr Arg
    130                 135                 140

Ile Leu Val Thr Ile Ser Asp Gln His Ile Arg Gly Ala Leu Asn Val
145                 150                 155                 160

Pro Leu Lys Gly Val Arg Tyr Val Leu Arg Val Ala Asp Asp Ile Ile
                165                 170                 175

Gly Pro Thr Gly Asp Val Met Thr Leu Asn Gly His Tyr Pro Tyr Thr
            180                 185                 190

Glu Lys Val His Ser Thr Lys Tyr His Phe Thr Ile Ile Phe Asn Pro
        195                 200                 205

Pro Pro Leu Phe Ser Phe Tyr Arg Leu Ile Asp Lys Gly Phe Gly Ile
    210                 215                 220

Leu Ile Phe Ile Leu Leu Ile Ala Cys Ala Ala Ala Phe Leu Leu Asp
225                 230                 235                 240
```

Arg Tyr Phe Asn Lys Ser Ala Thr Pro Glu Ile Leu Arg Arg Ala
                245                 250                 255

Ile Asn Asn Gly Glu Ile Val Pro Phe Tyr Gln Pro Val Val Asn Gly
        260                 265                 270

Arg Glu Gly Thr Leu Arg Gly Val Glu Val Leu Ala Arg Trp Lys Gln
    275                 280                 285

Pro His Gly Gly Tyr Ile Ser Pro Ala Ala Phe Ile Pro Leu Ala Glu
290                 295                 300

Lys Ser Gly Leu Ile Val Pro Leu Thr Gln Ser Leu Met Asn Gln Val
305                 310                 315                 320

Ala Arg Gln Met Asn Ala Ile Ala Ser Lys Leu Pro Glu Gly Phe His
                325                 330                 335

Ile Gly Ile Asn Phe Ser Ala Ser His Ile Ile Ser Pro Thr Phe Val
            340                 345                 350

Asp Glu Cys Leu Asn Phe Arg Asp Ser Phe Thr Arg Arg Asp Leu Asn
        355                 360                 365

Leu Val Leu Glu Val Thr Glu Arg Glu Pro Leu Asn Val Asp Glu Ser
    370                 375                 380

Leu Val Gln Arg Leu Asn Ile Leu His Glu Asn Gly Phe Val Ile Ala
385                 390                 395                 400

Leu Asp Asp Phe Gly Thr Gly Tyr Ser Gly Leu Ser Tyr Leu His Asp
                405                 410                 415

Leu His Ile Asp Tyr Ile Lys Ile Asp His Ser Phe Val Gly Arg Val
            420                 425                 430

Asn Ala Asp Pro Glu Ser Thr Arg Ile Leu Asp Cys Val Leu Asp Leu
        435                 440                 445

Ala Arg Lys Leu Ser Ile Ser Ile Val Ala Glu Gly Val Glu Thr Lys
    450                 455                 460

Glu Gln Leu Asp Tyr Leu Asn Gln Asn Tyr Ile Thr Phe Gln Gln Gly
465                 470                 475                 480

Tyr Tyr Phe Tyr Lys Pro Val Thr Tyr Ile Asp Leu Val Lys Ile Ile
                485                 490                 495

Leu Ser Lys Pro Lys Val Lys Val Val Glu
            500                 505

<210> SEQ ID NO 23
<211> LENGTH: 271
<212> TYPE: PRT
<213> ORGANISM: Escherichia coli

<400> SEQUENCE: 23

Met Gln Tyr Trp Gly Lys Ile Ile Gly Val Ala Val Ala Leu Leu Met
1               5                   10                  15

Gly Gly Gly Phe Trp Gly Val Val Leu Gly Leu Leu Ile Gly His Met
                20                  25                  30

Phe Asp Lys Ala Arg Ser Arg Lys Met Ala Trp Phe Ala Asn Gln Arg
            35                  40                  45

Glu Arg Gln Ala Leu Phe Phe Ala Thr Thr Phe Glu Val Met Gly His
        50                  55                  60

Leu Thr Lys Ser Lys Gly Arg Val Thr Glu Ala Asp Ile His Ile Ala
65                  70                  75                  80

Ser Gln Leu Met Asp Arg Met Asn Leu His Gly Ala Ser Arg Thr Ala
                85                  90                  95

Ala Gln Asn Ala Phe Arg Val Gly Lys Ser Asp Asn Tyr Pro Leu Arg
            100                 105                 110

```
Glu Lys Met Arg Gln Phe Arg Ser Val Cys Phe Gly Arg Phe Asp Leu
            115                 120                 125

Ile Arg Met Phe Leu Glu Ile Gln Ile Gln Ala Ala Phe Ala Asp Gly
        130                 135                 140

Ser Leu His Pro Asn Glu Arg Ala Val Leu Tyr Val Ile Ala Glu Glu
145                 150                 155                 160

Leu Gly Ile Ser Arg Ala Gln Phe Asp Gln Phe Leu Arg Met Met Gln
                165                 170                 175

Gly Gly Ala Gln Phe Gly Gly Gly Tyr Gln Gln Gln Thr Gly Gly Gly
                180                 185                 190

Asn Trp Gln Gln Ala Gln Arg Gly Pro Thr Leu Glu Asp Ala Cys Asn
            195                 200                 205

Val Leu Gly Val Lys Pro Thr Asp Asp Ala Thr Thr Ile Lys Arg Ala
        210                 215                 220

Tyr Arg Lys Leu Met Ser Glu His His Pro Asp Lys Leu Val Ala Lys
225                 230                 235                 240

Gly Leu Pro Pro Glu Met Met Glu Met Ala Lys Gln Lys Ala Gln Glu
                245                 250                 255

Ile Gln Gln Ala Tyr Glu Leu Ile Lys Gln Lys Gly Phe Lys
                260                 265                 270
```

<210> SEQ ID NO 24
<211> LENGTH: 349
<212> TYPE: PRT
<213> ORGANISM: Escherichia coli

<400> SEQUENCE: 24

```
Met Glu Leu Leu Ser Glu Tyr Gly Leu Phe Leu Ala Lys Ile Val Thr
1               5                   10                  15

Val Val Leu Ala Ile Ala Ala Ile Ala Ala Ile Ile Val Asn Val Ala
                20                  25                  30

Gln Arg Asn Lys Arg Gln Arg Gly Glu Leu Arg Val Asn Asn Leu Ser
            35                  40                  45

Glu Gln Tyr Lys Glu Met Lys Glu Glu Leu Ala Ala Ala Leu Met Asp
50                  55                  60

Ser His Gln Gln Lys Gln Trp His Lys Ala Gln Lys Lys His Lys
65                  70                  75                  80

Gln Glu Ala Lys Ala Ala Lys Ala Lys Ala Lys Leu Gly Glu Val Ala
                85                  90                  95

Thr Asp Ser Lys Pro Arg Val Trp Val Leu Asp Phe Lys Gly Ser Met
            100                 105                 110

Asp Ala His Glu Val Asn Ser Leu Arg Glu Glu Ile Thr Ala Val Leu
        115                 120                 125

Ala Ala Phe Lys Pro Gln Asp Gln Val Val Leu Arg Leu Glu Ser Pro
        130                 135                 140

Gly Gly Met Val His Gly Tyr Gly Leu Ala Ala Ser Gln Leu Gln Arg
145                 150                 155                 160

Leu Arg Asp Lys Asn Ile Pro Leu Thr Val Thr Val Asp Lys Val Ala
                165                 170                 175

Ala Ser Gly Gly Tyr Met Met Ala Cys Val Ala Asp Lys Ile Val Ser
                180                 185                 190

Ala Pro Phe Ala Ile Val Gly Ser Ile Gly Val Val Ala Gln Met Pro
            195                 200                 205

Asn Phe Asn Arg Phe Leu Lys Ser Lys Asp Ile Asp Ile Glu Leu His
```

```
              210                 215                 220
Thr Ala Gly Gln Tyr Lys Arg Thr Leu Thr Leu Leu Gly Glu Asn Thr
225                 230                 235                 240

Glu Glu Gly Arg Glu Lys Phe Arg Glu Glu Leu Asn Glu Thr His Gln
                    245                 250                 255

Leu Phe Lys Asp Phe Val Lys Arg Met Arg Pro Ser Leu Asp Ile Glu
                260                 265                 270

Gln Val Ala Thr Gly Glu His Trp Tyr Gly Gln Gln Ala Val Glu Lys
            275                 280                 285

Gly Leu Val Asp Glu Ile Asn Thr Ser Asp Glu Val Ile Leu Ser Leu
        290                 295                 300

Met Glu Gly Arg Glu Val Val Asn Val Arg Tyr Met Gln Arg Lys Arg
305                 310                 315                 320

Leu Ile Asp Arg Phe Thr Gly Ser Ala Ala Glu Ser Ala Asp Arg Leu
                325                 330                 335

Leu Leu Arg Trp Trp Gln Arg Gly Gln Lys Pro Leu Met
                340                 345

<210> SEQ ID NO 25
<211> LENGTH: 328
<212> TYPE: PRT
<213> ORGANISM: Escherichia coli

<400> SEQUENCE: 25

Met Ile Glu Lys Ile Trp Ser Gly Glu Ser Pro Leu Trp Arg Leu Leu
1               5                   10                  15

Leu Pro Leu Ser Trp Leu Tyr Gly Leu Val Ser Gly Ala Ile Arg Leu
                20                  25                  30

Cys Tyr Lys Leu Lys Leu Lys Arg Ala Trp Arg Ala Pro Val Pro Val
            35                  40                  45

Val Val Val Gly Asn Leu Thr Ala Gly Gly Asn Gly Lys Thr Pro Val
        50                  55                  60

Val Val Trp Leu Val Glu Gln Leu Gln Gln Arg Gly Ile Arg Val Gly
65                  70                  75                  80

Val Val Ser Arg Gly Tyr Gly Gly Lys Ala Glu Ser Tyr Pro Leu Leu
                85                  90                  95

Leu Ser Ala Asp Thr Thr Thr Ala Gln Ala Gly Asp Glu Pro Val Leu
            100                 105                 110

Ile Tyr Gln Arg Thr Asp Ala Pro Val Ala Val Ser Pro Val Arg Ser
        115                 120                 125

Asp Ala Val Lys Ala Ile Leu Ala Gln His Pro Asp Val Gln Ile Ile
    130                 135                 140

Val Thr Asp Asp Gly Leu Gln His Tyr Arg Leu Ala Arg Asp Val Glu
145                 150                 155                 160

Ile Val Val Ile Asp Gly Val Arg Arg Phe Gly Asn Gly Trp Trp Leu
                165                 170                 175

Pro Ala Gly Pro Met Arg Glu Arg Ala Gly Arg Leu Lys Ser Val Asp
            180                 185                 190

Ala Val Ile Val Asn Gly Gly Val Pro Arg Ser Gly Glu Ile Pro Met
        195                 200                 205

His Leu Leu Pro Gly Gln Ala Val Asn Leu Arg Thr Gly Thr Arg Cys
    210                 215                 220

Asp Val Ala Gln Leu Glu His Val Val Ala Met Ala Gly Ile Gly His
225                 230                 235                 240
```

```
Pro Pro Arg Phe Phe Ala Thr Leu Lys Met Cys Gly Val Gln Pro Glu
            245                 250                 255

Lys Cys Val Pro Leu Ala Asp His Gln Ser Leu Asn His Ala Asp Val
        260                 265                 270

Ser Ala Leu Val Ser Ala Gly Gln Thr Leu Val Met Thr Glu Lys Asp
            275                 280                 285

Ala Val Lys Cys Arg Ala Phe Ala Glu Glu Asn Trp Trp Tyr Leu Pro
        290                 295                 300

Val Asp Ala Gln Leu Ser Gly Asp Glu Pro Ala Lys Leu Leu Thr Gln
305                 310                 315                 320

Leu Thr Leu Leu Ala Ser Gly Asn
            325

<210> SEQ ID NO 26
<211> LENGTH: 121
<212> TYPE: PRT
<213> ORGANISM: Escherichia coli

<400> SEQUENCE: 26

Met Asn Asn His Ala Thr Val Gln Ser Ser Ala Pro Val Ser Ala Ala
1               5                   10                  15

Pro Leu Leu Gln Val Ser Gly Ala Leu Ile Ala Ile Ala Leu Ile
            20                  25                  30

Leu Ala Ala Ala Trp Leu Val Lys Arg Leu Gly Phe Ala Pro Lys Arg
        35                  40                  45

Thr Gly Val Asn Gly Leu Lys Ile Ser Ala Ser Ala Ser Leu Gly Ala
    50                  55                  60

Arg Glu Arg Val Val Val Asp Val Glu Asp Ala Arg Leu Val Leu
65                  70                  75                  80

Gly Val Thr Ala Gly Gln Ile Asn Leu Leu His Lys Leu Pro Pro Ser
                85                  90                  95

Ala Pro Thr Glu Glu Ile Pro Gln Thr Asp Phe Gln Ser Val Met Lys
            100                 105                 110

Asn Leu Leu Lys Arg Ser Gly Arg Ser
        115                 120

<210> SEQ ID NO 27
<211> LENGTH: 295
<212> TYPE: PRT
<213> ORGANISM: Escherichia coli

<400> SEQUENCE: 27

Met Leu Ile Leu Leu Gly Tyr Leu Val Val Leu Gly Thr Val Phe Gly
1               5                   10                  15

Gly Tyr Leu Met Thr Gly Gly Ser Leu Gly Ala Leu Tyr Gln Pro Ala
            20                  25                  30

Glu Leu Val Ile Ile Ala Gly Ala Gly Ile Gly Ser Phe Ile Val Gly
        35                  40                  45

Asn Asn Gly Lys Ala Ile Lys Gly Thr Leu Lys Ala Leu Pro Leu Leu
    50                  55                  60

Phe Arg Arg Ser Lys Tyr Thr Lys Ala Met Tyr Met Asp Leu Leu Ala
65                  70                  75                  80

Leu Leu Tyr Arg Leu Met Ala Lys Ser Arg Gln Met Gly Met Phe Ser
                85                  90                  95

Leu Glu Arg Asp Ile Glu Asn Pro Arg Glu Ser Glu Ile Phe Ala Ser
            100                 105                 110
```

```
Tyr Pro Arg Ile Leu Ala Asp Ser Val Met Leu Asp Phe Ile Val Asp
        115                 120                 125

Tyr Leu Arg Leu Ile Ile Ser Gly His Met Asn Thr Phe Glu Ile Glu
130                 135                 140

Ala Leu Met Asp Glu Glu Ile Glu Thr His Glu Ser Glu Ala Glu Val
145                 150                 155                 160

Pro Ala Asn Ser Leu Ala Leu Val Gly Asp Ser Leu Pro Ala Phe Gly
                165                 170                 175

Ile Val Ala Ala Val Met Gly Val Val His Ala Leu Gly Ser Ala Asp
            180                 185                 190

Arg Pro Ala Ala Glu Leu Gly Ala Leu Ile Ala His Ala Met Val Gly
        195                 200                 205

Thr Phe Leu Gly Ile Leu Leu Ala Tyr Gly Phe Ile Ser Pro Leu Ala
210                 215                 220

Thr Val Leu Arg Gln Lys Ser Ala Glu Thr Ser Lys Met Met Gln Cys
225                 230                 235                 240

Val Lys Val Thr Leu Leu Ser Asn Leu Asn Gly Tyr Ala Pro Pro Ile
                245                 250                 255

Ala Val Glu Phe Gly Arg Lys Thr Leu Tyr Ser Ser Glu Arg Pro Ser
            260                 265                 270

Phe Ile Glu Leu Glu Glu His Val Arg Ala Val Lys Asn Pro Gln Gln
        275                 280                 285

Gln Thr Thr Thr Glu Glu Ala
        290                 295

<210> SEQ ID NO 28
<211> LENGTH: 293
<212> TYPE: PRT
<213> ORGANISM: Escherichia coli

<400> SEQUENCE: 28

Met Met Arg Ile Ala Leu Phe Leu Leu Thr Asn Leu Ala Val Met Val
1               5                   10                  15

Val Phe Gly Leu Val Leu Ser Leu Thr Gly Ile Gln Ser Ser Ser Val
                20                  25                  30

Gln Gly Leu Met Ile Met Ala Leu Leu Phe Gly Phe Gly Gly Ser Phe
            35                  40                  45

Val Ser Leu Leu Met Ser Lys Trp Met Ala Leu Arg Ser Val Gly Gly
        50                  55                  60

Glu Val Ile Glu Gln Pro Arg Asn Glu Arg Glu Arg Trp Leu Val Asn
65                  70                  75                  80

Thr Val Ala Thr Gln Ala Arg Gln Ala Gly Ile Ala Met Pro Gln Val
                85                  90                  95

Ala Ile Tyr His Ala Pro Asp Ile Asn Ala Phe Ala Thr Gly Ala Arg
            100                 105                 110

Arg Asp Ala Ser Leu Val Ala Val Ser Thr Gly Leu Leu Gln Asn Met
        115                 120                 125

Ser Pro Asp Glu Ala Glu Ala Val Ile Ala His Glu Ile Ser His Ile
130                 135                 140

Ala Asn Gly Asp Met Val Thr Met Thr Leu Ile Gln Gly Val Val Asn
145                 150                 155                 160

Thr Phe Val Ile Phe Ile Ser Arg Ile Leu Ala Gln Leu Ala Ala Gly
                165                 170                 175

Phe Met Gly Gly Asn Arg Asp Glu Gly Glu Ser Asn Gly Asn Pro
            180                 185                 190
```

```
Leu Ile Tyr Phe Ala Val Ala Thr Val Leu Glu Leu Val Phe Gly Ile
        195                 200                 205

Leu Ala Ser Ile Ile Thr Met Trp Phe Ser Arg His Arg Glu Phe His
210                 215                 220

Ala Asp Ala Gly Ser Ala Lys Leu Val Gly Arg Glu Lys Met Ile Ala
225                 230                 235                 240

Ala Leu Gln Arg Leu Lys Thr Ser Tyr Glu Pro Gln Glu Ala Thr Ser
            245                 250                 255

Met Met Ala Leu Cys Ile Asn Gly Lys Ser Lys Ser Leu Ser Glu Leu
                260                 265                 270

Phe Met Thr His Pro Pro Leu Asp Lys Arg Ile Glu Ala Leu Arg Thr
            275                 280                 285

Gly Glu Tyr Leu Lys
        290

<210> SEQ ID NO 29
<211> LENGTH: 441
<212> TYPE: PRT
<213> ORGANISM: Escherichia coli

<400> SEQUENCE: 29

Met Ile Asn Arg Ile Val Ser Phe Phe Ile Leu Cys Leu Val Leu Cys
1               5                   10                  15

Ile Pro Leu Cys Val Ala Tyr Phe His Ser Gly Glu Leu Met Met Arg
            20                  25                  30

Phe Val Phe Phe Trp Pro Phe Phe Met Ser Ile Met Trp Ile Val Gly
        35                  40                  45

Gly Val Tyr Phe Trp Val Tyr Arg Glu Arg His Trp Pro Trp Gly Glu
    50                  55                  60

Asn Ala Pro Ala Pro Gln Leu Lys Asp Asn Pro Ser Ile Ser Ile Ile
65                  70                  75                  80

Ile Pro Cys Phe Asn Glu Glu Lys Asn Val Glu Glu Thr Ile His Ala
                85                  90                  95

Ala Leu Ala Gln Arg Tyr Glu Asn Ile Glu Val Ile Ala Val Asn Asp
            100                 105                 110

Gly Ser Thr Asp Lys Thr Arg Ala Ile Leu Asp Arg Met Ala Ala Gln
        115                 120                 125

Ile Pro His Leu Arg Val Ile His Leu Ala Gln Asn Gln Gly Lys Ala
    130                 135                 140

Ile Ala Leu Lys Thr Gly Ala Ala Ala Lys Ser Glu Tyr Leu Val
145                 150                 155                 160

Cys Ile Asp Gly Asp Ala Leu Leu Asp Arg Asp Ala Ala Ala Tyr Ile
                165                 170                 175

Val Glu Pro Met Leu Tyr Asn Pro Arg Val Gly Ala Val Thr Gly Asn
            180                 185                 190

Pro Arg Ile Arg Thr Arg Ser Thr Leu Val Gly Lys Ile Gln Val Gly
        195                 200                 205

Glu Tyr Ser Ser Ile Ile Gly Leu Ile Lys Arg Thr Gln Arg Ile Tyr
    210                 215                 220

Gly Asn Val Phe Thr Val Ser Gly Val Ile Ala Ala Phe Arg Arg Ser
225                 230                 235                 240

Ala Leu Ala Glu Val Gly Tyr Trp Ser Asp Asp Met Ile Thr Glu Asp
                245                 250                 255

Ile Asp Ile Ser Trp Lys Leu Gln Leu Asn Gln Trp Thr Ile Phe Tyr
```

```
                     260                 265                 270
Glu Pro Arg Ala Leu Cys Trp Ile Leu Met Pro Glu Thr Leu Lys Gly
        275                 280                 285

Leu Trp Lys Gln Arg Leu Arg Trp Ala Gln Gly Gly Ala Glu Val Phe
    290                 295                 300

Leu Lys Asn Met Thr Arg Leu Trp Arg Lys Glu Asn Phe Arg Met Trp
305                 310                 315                 320

Pro Leu Phe Phe Glu Tyr Cys Leu Thr Thr Ile Trp Ala Phe Thr Cys
                325                 330                 335

Leu Val Gly Phe Ile Ile Tyr Ala Val Gln Leu Ala Gly Val Pro Leu
            340                 345                 350

Asn Ile Glu Leu Thr His Ile Ala Ala Thr His Thr Ala Gly Ile Leu
        355                 360                 365

Leu Cys Thr Leu Cys Leu Leu Gln Phe Ile Val Ser Leu Met Ile Glu
    370                 375                 380

Asn Arg Tyr Glu His Asn Leu Thr Ser Ser Leu Phe Trp Ile Ile Trp
385                 390                 395                 400

Phe Pro Val Ile Phe Trp Met Leu Ser Leu Ala Thr Thr Leu Val Ser
                405                 410                 415

Phe Thr Arg Val Met Leu Met Pro Lys Lys Gln Arg Ala Arg Trp Val
            420                 425                 430

Ser Pro Asp Arg Gly Ile Leu Arg Gly
        435                 440

<210> SEQ ID NO 30
<211> LENGTH: 131
<212> TYPE: PRT
<213> ORGANISM: Escherichia coli

<400> SEQUENCE: 30

Met Thr Ser Arg Phe Met Leu Ile Phe Ala Ala Ile Ser Gly Phe Ile
1               5                   10                  15

Phe Val Ala Leu Gly Ala Phe Gly Ala His Val Leu Ser Lys Thr Met
            20                  25                  30

Gly Ala Val Glu Met Gly Trp Ile Gln Thr Gly Leu Glu Tyr Gln Ala
        35                  40                  45

Phe His Thr Leu Ala Ile Leu Gly Leu Ala Val Ala Met Gln Arg Arg
    50                  55                  60

Ile Ser Ile Trp Phe Tyr Trp Ser Ser Val Phe Leu Ala Leu Gly Thr
65                  70                  75                  80

Val Leu Phe Ser Gly Ser Leu Tyr Cys Leu Ala Leu Ser His Leu Arg
                85                  90                  95

Leu Trp Ala Phe Val Thr Pro Val Gly Gly Val Ser Phe Leu Ala Gly
            100                 105                 110

Trp Ala Leu Met Leu Val Gly Ala Ile Arg Leu Lys Arg Lys Gly Val
        115                 120                 125

Ser His Glu
    130

<210> SEQ ID NO 31
<211> LENGTH: 655
<212> TYPE: PRT
<213> ORGANISM: Escherichia coli

<400> SEQUENCE: 31

Met Asn Val Ile Lys Thr Ala Ile Cys Thr Leu Ile Thr Leu Pro Val
```

```
1               5                   10                  15
Gly Leu Gln Ala Ala Thr Ser His Ser Ser Met Thr Lys Asp Thr
                20                  25                  30
Ile Thr Val Val Ala Thr Gly Asn Gln Asn Thr Val Phe Glu Thr Pro
                35                  40                  45
Ser Met Val Ser Val Val Thr Asn Asp Thr Pro Trp Ser Lys Asn Ala
    50                  55                  60
Val Thr Ser Ala Gly Met Leu Arg Gly Val Ala Gly Leu Ser Gln Thr
65                  70                  75                  80
Gly Ala Gly Arg Thr Asn Gly Gln Thr Phe Asn Leu Arg Gly Tyr Asp
                85                  90                  95
Lys Ser Gly Val Leu Val Leu Val Asp Gly Val Arg Gln Leu Ser Asp
                100                 105                 110
Met Ala Lys Ser Ser Gly Thr Tyr Leu Asp Pro Ala Leu Val Lys Arg
                115                 120                 125
Ile Glu Val Val Arg Gly Pro Asn Ser Ser Leu Tyr Gly Ser Gly Gly
            130                 135                 140
Leu Gly Gly Val Val Asp Phe Arg Thr Ala Asp Ala Ala Asp Phe Leu
145                 150                 155                 160
Pro Pro Gly Glu Thr Asn Gly Val Ser Leu Trp Gly Asn Ile Ala Ser
                165                 170                 175
Gly Asp His Ser Thr Gly Ser Gly Leu Thr Trp Phe Gly Lys Thr Glu
                180                 185                 190
Lys Thr Asp Ala Leu Leu Ser Val Ile Met Arg Lys Arg Gly Ser Ile
            195                 200                 205
Tyr Gln Ser Asp Gly Glu Arg Ala Pro Asn Lys Glu Lys Pro Ala Ala
    210                 215                 220
Leu Phe Ala Lys Gly Ser Val Ser Ile Thr Asp Ser Asn Lys Ala Gly
225                 230                 235                 240
Ala Ser Leu Arg Leu Tyr Arg Asn Ser Thr Thr Glu Pro Gly Asn Pro
                245                 250                 255
Thr Leu Thr His Gly Asp Ser Gly Leu Arg Asp Arg Lys Thr Ala Gln
                260                 265                 270
Asn Asp Met Gln Phe Trp Tyr Gln Tyr Ala Pro Ala Asp Asn Ser Leu
            275                 280                 285
Ile Asn Val Lys Ser Thr Leu Tyr Leu Ser Asp Ile Thr Val Lys Thr
    290                 295                 300
Asn Gly His Asn Lys Thr Ala Glu Trp Arg Asn Asn Arg Thr Ser Gly
305                 310                 315                 320
Val Asn Val Val Asn Arg Ser His Ser Leu Ile Phe Pro Gly Ala His
                325                 330                 335
Gln Leu Ser Tyr Gly Ala Glu Tyr Tyr Arg Gln Gln Lys Pro Glu
                340                 345                 350
Gly Thr Ala Thr Leu Tyr Pro Glu Gly His Ile Asp Phe Thr Ser Leu
            355                 360                 365
Tyr Phe Gln Asp Glu Met Thr Met Glu Ser Tyr Pro Val Asn Ile Ile
    370                 375                 380
Val Gly Ser Arg Tyr Asp Arg Tyr Asn Ser Phe Asn Ala Arg Ala Gly
385                 390                 395                 400
Glu Leu Asn Ala Glu Arg Leu Ser Pro Arg Ala Ala Met Ser Val Ser
                405                 410                 415
Pro Thr Asp Trp Leu Met Met Tyr Gly Ser Ile Ser Ser Ala Phe Arg
                420                 425                 430
```

```
Ala Pro Thr Met Ala Glu Met Tyr Arg Asp Asp Val His Phe Tyr Arg
            435                 440                 445

Lys Gly Lys Pro Asn Tyr Trp Val Pro Asn Leu Asn Leu Lys Pro Glu
450                 455                 460

Asn Asn Thr Thr Arg Glu Ile Gly Ala Gly Ile Gln Leu Asp Ser Leu
465                 470                 475                 480

Leu Thr Asp Asn Asp Arg Leu Gln Leu Lys Gly Gly Tyr Phe Gly Thr
                485                 490                 495

Asp Ala Arg Asn Tyr Ile Ala Thr Arg Val Asp Met Lys Arg Met Arg
            500                 505                 510

Ser Tyr Ser Tyr Asn Val Ser Arg Ala Arg Ile Trp Gly Trp Asp Ile
        515                 520                 525

Gln Gly Asn Tyr Gln Ser Asp Tyr Val Asp Trp Met Leu Ser Tyr Asn
        530                 535                 540

Arg Thr Glu Ser Met Asp Ala Ser Ser Arg Glu Trp Leu Gly Ser Gly
545                 550                 555                 560

Asn Pro Asp Thr Leu Ile Ser Asp Ile Ser Ile Pro Val Gly His Arg
                565                 570                 575

Gly Val Tyr Ala Gly Trp Arg Ala Glu Leu Ser Ala Pro Ala Thr His
            580                 585                 590

Val Lys Lys Gly Asp Pro Cys Gln Asp Gly Tyr Ala Ile His Ser Phe
        595                 600                 605

Ser Leu Ser Tyr Lys Pro Val Ser Val Lys Gly Phe Glu Ala Ser Val
        610                 615                 620

Thr Leu Asp Asn Ala Phe Asn Lys Leu Ala Met Asn Gly Lys Gly Val
625                 630                 635                 640

Pro Leu Ser Gly Arg Thr Val Asn Leu Tyr Thr Arg Tyr Gln Trp
                645                 650                 655

<210> SEQ ID NO 32
<211> LENGTH: 102
<212> TYPE: PRT
<213> ORGANISM: Escherichia coli

<400> SEQUENCE: 32

Met Lys Tyr Leu Leu Ile Phe Leu Leu Val Leu Ala Ile Phe Val Ile
1               5                   10                  15

Ser Val Thr Leu Gly Ala Gln Asn Asp Gln Gln Val Thr Phe Asn Tyr
                20                  25                  30

Leu Leu Ala Gln Gly Glu Tyr Arg Ile Ser Thr Leu Leu Ala Val Leu
            35                  40                  45

Phe Ala Ala Gly Phe Ala Ile Gly Trp Leu Ile Cys Gly Leu Phe Trp
        50                  55                  60

Leu Arg Val Arg Val Ser Leu Ala Arg Ala Glu Arg Lys Ile Lys Arg
65                  70                  75                  80

Leu Glu Asn Gln Leu Ser Pro Ala Thr Asp Val Ala Val Val Pro His
                85                  90                  95

Ser Ser Ala Ala Lys Glu
            100

<210> SEQ ID NO 33
<211> LENGTH: 710
<212> TYPE: PRT
<213> ORGANISM: Stevia rebaudiana

<400> SEQUENCE: 33
```

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
                35                  40                  45

Leu Leu Thr Leu Phe Thr Thr Ser Phe Ala Val Leu Ile Gly Cys Leu
        50                  55                  60

Val Phe Leu Met Trp Arg Arg Ser Ser Lys Lys Leu Val Gln Asp
65              70                  75                  80

Pro Val Pro Gln Val Ile Val Lys Lys Glu Lys Glu Ser Glu
                85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Gly Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
                180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Thr Ser Val Thr Thr Pro
                260                 265                 270

Tyr Thr Ala Ala Val Leu Glu Tyr Arg Val Val Tyr His Asp Lys Pro
    275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
                340                 345                 350

Tyr Ser Glu Asn Leu Ser Glu Val Asp Glu Ala Leu Lys Leu Leu
    355                 360                 365

Gly Leu Ser Pro Asp Thr Tyr Phe Ser Val His Ala Asp Lys Glu Asp
370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415
```

Lys Lys Val Ala Leu Ala Leu Ala Ala His Ala Ser Asp Pro Ser
                420                 425                 430

Glu Ala Asp Arg Leu Lys Phe Leu Ala Ser Pro Ala Gly Lys Asp Glu
            435                 440                 445

Tyr Ala Gln Trp Ile Val Ala Asn Gln Arg Ser Leu Leu Glu Val Met
        450                 455                 460

Gln Ser Phe Pro Ser Ala Lys Pro Pro Leu Gly Val Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710

<210> SEQ ID NO 34
<211> LENGTH: 692
<212> TYPE: PRT
<213> ORGANISM: Arabidopsis thaliana

<400> SEQUENCE: 34

Met Thr Ser Ala Leu Tyr Ala Ser Asp Leu Phe Lys Gln Leu Lys Ser
1               5                   10                  15

Ile Met Gly Thr Asp Ser Leu Ser Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

```
Gly Lys Thr Arg Val Ser Ile Phe Phe Gly Thr Gln Thr Gly Thr Ala
                85                  90                  95
Glu Gly Phe Ala Lys Ala Leu Ser Glu Ile Lys Ala Arg Tyr Glu
            100                 105                 110
Lys Ala Ala Val Lys Val Ile Asp Leu Asp Asp Tyr Ala Asp Asp
            115                 120                 125
Asp Gln Tyr Glu Glu Lys Leu Lys Lys Glu Thr Leu Ala Phe Phe Cys
    130                 135                 140
Val Ala Thr Tyr Gly Asp Gly Glu Pro Thr Asp Asn Ala Ala Arg Phe
145                 150                 155                 160
Ser Lys Trp Phe Thr Glu Glu Asn Glu Arg Asp Ile Lys Leu Gln Gln
                165                 170                 175
Leu Ala Tyr Gly Val Phe Ala Leu Gly Asn Arg Gln Tyr Glu His Phe
            180                 185                 190
Asn Lys Ile Gly Ile Val Leu Asp Glu Glu Leu Cys Lys Lys Gly Ala
                195                 200                 205
Lys Arg Leu Ile Glu Val Gly Leu Gly Asp Asp Asp Gln Ser Ile Glu
    210                 215                 220
Asp Asp Phe Asn Ala Trp Lys Glu Ser Leu Trp Ser Glu Leu Asp Lys
225                 230                 235                 240
Leu Leu Lys Asp Glu Asp Lys Ser Val Ala Thr Pro Tyr Thr Ala
                245                 250                 255
Val Ile Pro Glu Tyr Arg Val Val Thr His Asp Pro Arg Phe Thr Thr
                260                 265                 270
Gln Lys Ser Met Glu Ser Asn Val Ala Asn Gly Asn Thr Thr Ile Asp
    275                 280                 285
Ile His His Pro Cys Arg Val Asp Val Ala Val Gln Lys Glu Leu His
    290                 295                 300
Thr His Glu Ser Asp Arg Ser Cys Ile His Leu Glu Phe Asp Ile Ser
305                 310                 315                 320
Arg Thr Gly Ile Thr Tyr Glu Thr Gly Asp His Val Gly Val Tyr Ala
                325                 330                 335
Glu Asn His Val Glu Ile Val Glu Glu Ala Gly Lys Leu Leu Gly His
            340                 345                 350
Ser Leu Asp Leu Val Phe Ser Ile His Ala Asp Lys Glu Asp Gly Ser
    355                 360                 365
Pro Leu Glu Ser Ala Val Pro Pro Phe Pro Gly Pro Cys Thr Leu
370                 375                 380
Gly Thr Gly Leu Ala Arg Tyr Ala Asp Leu Leu Asn Pro Pro Arg Lys
385                 390                 395                 400
Ser Ala Leu Val Ala Leu Ala Tyr Ala Thr Glu Pro Ser Glu Ala
                405                 410                 415
Glu Lys Leu Lys His Leu Thr Ser Pro Asp Gly Lys Asp Glu Tyr Ser
            420                 425                 430
Gln Trp Ile Val Ala Ser Gln Arg Ser Leu Leu Glu Val Met Ala Ala
    435                 440                 445
Phe Pro Ser Ala Lys Pro Pro Leu Gly Val Phe Phe Ala Ala Ile Ala
450                 455                 460
Pro Arg Leu Gln Pro Arg Tyr Tyr Ser Ile Ser Ser Cys Gln Asp Trp
465                 470                 475                 480
Ala Pro Ser Arg Val His Val Thr Ser Ala Leu Val Tyr Gly Pro Thr
                485                 490                 495
```

```
Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690
```

<210> SEQ ID NO 35
<211> LENGTH: 717
<212> TYPE: PRT
<213> ORGANISM: Taxus cuspidata

<400> SEQUENCE: 35

```
Met Gln Ala Asn Ser Asn Thr Val Glu Gly Ala Ser Gln Gly Lys Ser
1               5                   10                  15

Leu Leu Asp Ile Ser Arg Leu Asp His Ile Phe Ala Leu Leu Leu Asn
            20                  25                  30

Gly Lys Gly Gly Asp Leu Gly Ala Met Thr Gly Ser Ala Leu Ile Leu
        35                  40                  45

Thr Glu Asn Ser Gln Asn Leu Met Ile Leu Thr Thr Ala Leu Ala Val
    50                  55                  60

Leu Val Ala Cys Val Phe Phe Val Trp Arg Arg Gly Gly Ser Asp
65                  70                  75                  80

Thr Gln Lys Pro Ala Val Arg Pro Thr Pro Leu Val Lys Glu Glu Asp
                85                  90                  95

Glu Glu Glu Glu Asp Asp Ser Ala Lys Lys Val Thr Ile Phe Phe
            100                 105                 110

Gly Thr Gln Thr Gly Thr Ala Glu Gly Phe Ala Lys Ala Leu Ala Glu
        115                 120                 125

Glu Ala Lys Ala Arg Tyr Glu Lys Ala Val Phe Lys Val Val Asp Leu
    130                 135                 140

Asp Asn Tyr Ala Ala Asp Asp Glu Gln Tyr Glu Glu Lys Leu Lys Lys
145                 150                 155                 160

Glu Lys Leu Ala Phe Phe Met Leu Ala Thr Tyr Gly Asp Gly Glu Pro
                165                 170                 175
```

```
Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
        195                 200                 205

Asn Arg Gln Tyr Glu His Phe Asn Lys Val Ala Lys Ala Val Asp Glu
    210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Phe Thr Ala Trp Arg Glu Gln
                245                 250                 255

Val Trp Pro Glu Leu Asp Gln Leu Leu Arg Asp Glu Asp Glu Pro
        260                 265                 270

Thr Ser Ala Thr Pro Tyr Thr Ala Ile Pro Glu Tyr Arg Val Glu
    275                 280                 285

Ile Tyr Asp Ser Val Val Ser Val Tyr Glu Glu Thr His Ala Leu Lys
    290                 295                 300

Gln Asn Gly Gln Ala Val Tyr Asp Ile His His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
            340                 345                 350

Gly Asp His Val Gly Val His Thr Glu Asn Ser Ile Glu Thr Val Glu
        355                 360                 365

Glu Ala Lys Leu Leu Gly Tyr Gln Leu Asp Thr Ile Phe Ser Val
    370                 375                 380

His Gly Asp Lys Glu Asp Gly Thr Pro Leu Gly Gly Ser Ser Leu Pro
385                 390                 395                 400

Pro Pro Phe Pro Gly Pro Cys Thr Leu Arg Thr Ala Leu Ala Arg Tyr
                405                 410                 415

Ala Asp Leu Leu Asn Pro Pro Arg Lys Ala Ala Phe Leu Ala Leu Ala
            420                 425                 430

Ala His Ala Ser Asp Pro Ala Glu Ala Glu Arg Leu Lys Phe Leu Ser
        435                 440                 445

Ser Pro Ala Gly Lys Asp Glu Tyr Ser Gln Trp Val Thr Ala Ser Gln
    450                 455                 460

Arg Ser Leu Leu Glu Ile Met Ala Glu Phe Pro Ser Ala Lys Pro Pro
465                 470                 475                 480

Leu Gly Val Phe Phe Ala Ala Ile Ala Pro Arg Leu Gln Pro Arg Tyr
                485                 490                 495

Tyr Ser Ile Ser Ser Ser Pro Arg Phe Ala Pro Ser Arg Ile His Val
            500                 505                 510

Thr Cys Ala Leu Val Tyr Gly Pro Ser Pro Thr Gly Arg Ile His Lys
        515                 520                 525

Gly Val Cys Ser Asn Trp Met Lys Asn Ser Leu Pro Ser Glu Glu Thr
    530                 535                 540

His Asp Cys Ser Trp Ala Pro Val Phe Val Arg Gln Ser Asn Phe Lys
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
            580                 585                 590
```

```
Glu Ala Gly Glu Lys Leu Gly Pro Ala Val Leu Phe Phe Gly Cys Arg
                595                 600                 605

Asn Arg Gln Met Asp Tyr Ile Tyr Glu Asp Glu Leu Lys Gly Tyr Val
            610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
                645                 650                 655

Thr Trp Ser Leu Ile Ala Gln Gly Gly Tyr Leu Tyr Val Cys Gly Asp
            660                 665                 670

Ala Lys Gly Met Ala Arg Asp Val His Arg Thr Leu His Thr Ile Val
            675                 680                 685

Gln Glu Gln Glu Ser Val Asp Ser Ser Lys Ala Glu Phe Leu Val Lys
690                 695                 700

Lys Leu Gln Met Asp Gly Arg Tyr Leu Arg Asp Ile Trp
705                 710                 715

<210> SEQ ID NO 36
<211> LENGTH: 705
<212> TYPE: PRT
<213> ORGANISM: Artemesia annua

<400> SEQUENCE: 36

Met Ala Gln Ser Thr Thr Ser Val Lys Leu Ser Pro Phe Asp Leu Met
1               5                   10                  15

Thr Ala Leu Leu Asn Gly Lys Val Ser Phe Asp Thr Ser Asn Thr Ser
                20                  25                  30

Asp Thr Asn Ile Pro Leu Ala Val Phe Met Glu Asn Arg Glu Leu Leu
            35                  40                  45

Met Ile Leu Thr Thr Ser Val Ala Val Leu Ile Gly Cys Val Val Val
    50                  55                  60

Leu Val Trp Arg Arg Ser Ser Ser Ala Ala Lys Lys Ala Ala Glu Ser
65                  70                  75                  80

Pro Val Ile Val Val Pro Lys Lys Val Thr Glu Asp Glu Val Asp Asp
                85                  90                  95

Gly Arg Lys Lys Val Thr Val Phe Phe Gly Thr Gln Thr Gly Thr Ala
            100                 105                 110

Glu Gly Phe Ala Lys Ala Leu Val Glu Glu Ala Lys Ala Arg Tyr Glu
        115                 120                 125

Lys Ala Val Phe Lys Val Ile Asp Leu Asp Asp Tyr Ala Ala Glu Asp
    130                 135                 140

Asp Glu Tyr Glu Glu Lys Leu Lys Lys Glu Ser Leu Ala Phe Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Glu Glu Lys Gly Glu Trp Leu Asp Lys
            180                 185                 190

Leu Gln Tyr Ala Val Phe Gly Leu Gly Asn Arg Gln Tyr Glu His Phe
        195                 200                 205

Asn Lys Ile Ala Lys Val Val Asp Glu Lys Leu Val Glu Gln Gly Ala
    210                 215                 220

Lys Arg Leu Val Pro Val Gly Met Gly Asp Asp Gln Cys Ile Glu
225                 230                 235                 240

Asp Asp Phe Thr Ala Trp Lys Glu Leu Val Trp Pro Glu Leu Asp Gln
                245                 250                 255
```

```
Leu Leu Arg Asp Glu Asp Asp Thr Ser Val Ala Thr Pro Tyr Thr Ala
            260                 265                 270

Ala Val Ala Glu Tyr Arg Val Val Phe His Asp Lys Pro Glu Thr Tyr
            275                 280                 285

Asp Gln Asp Gln Leu Thr Asn Gly His Ala Val His Asp Ala Gln His
            290                 295                 300

Pro Cys Arg Ser Asn Val Ala Val Lys Lys Glu Leu His Ser Pro Leu
305                 310                 315                 320

Ser Asp Arg Ser Cys Thr His Leu Glu Phe Asp Ile Ser Asn Thr Gly
                325                 330                 335

Leu Ser Tyr Glu Thr Gly Asp His Val Gly Val Tyr Val Glu Asn Leu
            340                 345                 350

Ser Glu Val Val Asp Glu Ala Glu Lys Leu Ile Gly Leu Pro Pro His
            355                 360                 365

Thr Tyr Phe Ser Val His Ala Asp Asn Glu Asp Gly Thr Pro Leu Gly
            370                 375                 380

Gly Ala Ser Leu Pro Pro Phe Pro Pro Cys Thr Leu Arg Lys Ala
385                 390                 395                 400

Leu Ala Ser Tyr Ala Asp Val Leu Ser Ser Pro Lys Lys Ser Ala Leu
            405                 410                 415

Leu Ala Leu Ala Ala His Ala Thr Asp Ser Thr Glu Ala Asp Arg Leu
            420                 425                 430

Lys Phe Leu Ala Ser Pro Ala Gly Lys Asp Glu Tyr Ala Gln Trp Ile
            435                 440                 445

Val Ala Ser His Arg Ser Leu Leu Glu Val Met Glu Ala Phe Pro Ser
            450                 455                 460

Ala Lys Pro Pro Leu Gly Val Phe Phe Ala Ser Val Ala Pro Arg Leu
465                 470                 475                 480

Gln Pro Arg Tyr Tyr Ser Ile Ser Ser Ser Pro Arg Phe Ala Pro Asn
            485                 490                 495

Arg Ile His Val Thr Cys Ala Leu Val Tyr Glu Gln Thr Pro Ser Gly
            500                 505                 510

Arg Val His Lys Gly Val Cys Ser Thr Trp Met Lys Asn Ala Val Pro
            515                 520                 525

Met Thr Glu Ser Gln Asp Cys Ser Trp Ala Pro Ile Tyr Val Arg Thr
530                 535                 540

Ser Asn Phe Arg Leu Pro Ser Asp Pro Lys Val Pro Val Ile Met Ile
545                 550                 555                 560

Gly Pro Gly Thr Gly Leu Ala Pro Phe Arg Gly Phe Leu Gln Glu Arg
            565                 570                 575

Leu Ala Gln Lys Glu Ala Gly Thr Glu Leu Gly Thr Ala Ile Leu Phe
            580                 585                 590

Phe Gly Cys Arg Asn Arg Lys Val Asp Phe Ile Tyr Glu Asp Glu Leu
            595                 600                 605

Asn Asn Phe Val Glu Thr Gly Ala Leu Ser Glu Leu Val Thr Ala Phe
            610                 615                 620

Ser Arg Glu Gly Ala Thr Lys Glu Tyr Val Gln His Lys Met Thr Gln
625                 630                 635                 640

Lys Ala Ser Asp Ile Trp Asn Leu Leu Ser Glu Gly Ala Tyr Leu Tyr
            645                 650                 655

Val Cys Gly Asp Ala Lys Gly Met Ala Lys Asp Val His Arg Thr Leu
            660                 665                 670
```

```
His Thr Ile Val Gln Glu Gln Gly Ser Leu Asp Ser Lys Ala Glu
        675                 680                 685

Leu Tyr Val Lys Asn Leu Gln Met Ala Gly Arg Tyr Leu Arg Asp Val
690                 695                 700

Trp
705

<210> SEQ ID NO 37
<211> LENGTH: 693
<212> TYPE: PRT
<213> ORGANISM: Arabidopsis thaliana

<400> SEQUENCE: 37

Met Ala Thr Ser Ala Leu Tyr Ala Ser Asp Leu Phe Lys Gln Leu Lys
1               5                   10                  15

Ser Ile Met Gly Thr Asp Ser Leu Ser Asp Val Val Leu Val Ile
            20                  25                  30

Ala Thr Thr Ser Leu Ala Leu Val Ala Gly Phe Val Val Leu Leu Trp
            35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140

Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
        195                 200                 205

Ala Lys Arg Leu Ile Glu Val Gly Leu Gly Asp Asp Asp Gln Ser Ile
    210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Lys Ser Val Ala Thr Pro Tyr Thr
                245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
        275                 280                 285

Asp Ile His His Pro Cys Arg Val Asp Val Ala Val Gln Lys Glu Leu
    290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335
```

```
Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
            355                 360                 365

Ser Pro Leu Glu Ser Ala Val Pro Pro Phe Pro Gly Pro Cys Thr
    370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
            405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
            435                 440                 445

Ala Phe Pro Ser Ala Lys Pro Pro Leu Gly Val Phe Phe Ala Ala Ile
            450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
            485                 490                 495

Thr Pro Thr Gly Arg Ile His Lys Gly Val Cys Ser Thr Trp Met Lys
            500                 505                 510

Asn Ala Val Pro Ala Glu Lys Ser His Glu Cys Ser Gly Ala Pro Ile
            515                 520                 525

Phe Ile Arg Ala Ser Asn Phe Lys Leu Pro Ser Asn Pro Ser Thr Pro
            530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
            565                 570                 575

Ser Leu Leu Phe Phe Gly Cys Arg Asn Arg Gln Met Asp Phe Ile Tyr
            580                 585                 590

Glu Asp Glu Leu Asn Asn Phe Val Asp Gln Gly Val Ile Ser Glu Leu
            595                 600                 605

Ile Met Ala Phe Ser Arg Glu Gly Ala Gln Lys Glu Tyr Val Gln His
            610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
            645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
            675                 680                 685

Leu Arg Asp Val Trp
    690

<210> SEQ ID NO 38
<211> LENGTH: 712
<212> TYPE: PRT
<213> ORGANISM: Arabidopsis thaliana

<400> SEQUENCE: 38

Met Ala Ser Ser Ser Ser Ser Ser Ser Thr Ser Met Ile Asp Leu Met
```

-continued

```
  1               5                  10                  15
Ala Ala Ile Ile Lys Gly Glu Pro Val Ile Val Ser Asp Pro Ala Asn
             20                  25                  30

Ala Ser Ala Tyr Glu Ser Val Ala Ala Glu Leu Ser Ser Met Leu Ile
             35                  40                  45

Glu Asn Arg Gln Phe Ala Met Ile Val Thr Thr Ser Ile Ala Val Leu
             50                  55                  60

Ile Gly Cys Ile Val Met Leu Val Trp Arg Arg Ser Gly Ser Gly Asn
 65                  70                  75                  80

Ser Lys Arg Val Glu Pro Leu Lys Pro Leu Val Ile Lys Pro Arg Glu
             85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
            115                 120                 125

Lys Ala Arg Tyr Glu Lys Thr Arg Phe Lys Ile Val Asp Leu Asp Asp
            130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
            165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
            195                 200                 205

Gln Tyr Glu His Phe Asn Lys Val Ala Lys Val Val Asp Asp Ile Leu
            210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
            245                 250                 255

Pro Glu Leu Asp Thr Ile Leu Arg Glu Glu Gly Asp Thr Ala Val Ala
            260                 265                 270

Thr Pro Tyr Thr Ala Ala Val Leu Glu Tyr Arg Val Ser Ile His Asp
            275                 280                 285

Ser Glu Asp Ala Lys Phe Asn Asp Ile Asn Met Ala Asn Gly Asn Gly
            290                 295                 300

Tyr Thr Val Phe Asp Ala Gln His Pro Tyr Lys Ala Asn Val Ala Val
305                 310                 315                 320

Lys Arg Glu Leu His Thr Pro Glu Ser Asp Arg Ser Cys Ile His Leu
            325                 330                 335

Glu Phe Asp Ile Ala Gly Ser Gly Leu Thr Tyr Glu Thr Gly Asp His
            340                 345                 350

Val Gly Val Leu Cys Asp Asn Leu Ser Glu Thr Val Asp Glu Ala Leu
            355                 360                 365

Arg Leu Leu Asp Met Ser Pro Asp Thr Tyr Phe Ser Leu His Ala Glu
            370                 375                 380

Lys Glu Asp Gly Thr Pro Ile Ser Ser Ser Leu Pro Pro Pro Phe Pro
385                 390                 395                 400

Pro Cys Asn Leu Arg Thr Ala Leu Thr Arg Tyr Ala Cys Leu Leu Ser
            405                 410                 415

Ser Pro Lys Lys Ser Ala Leu Val Ala Leu Ala Ala His Ala Ser Asp
            420                 425                 430
```

Pro Thr Glu Ala Glu Arg Leu Lys His Leu Ala Ser Pro Ala Gly Lys
            435                 440                 445

Asp Glu Tyr Ser Lys Trp Val Val Glu Ser Gln Arg Ser Leu Leu Glu
    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
                500                 505                 510

Tyr Glu Lys Met Pro Thr Gly Arg Ile His Lys Gly Val Cys Ser Thr
            515                 520                 525

Trp Met Lys Asn Ala Val Pro Tyr Glu Lys Ser Glu Asn Cys Ser Ser
530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
                580                 585                 590

Leu Gly Pro Ser Val Leu Phe Phe Gly Cys Arg Asn Arg Arg Met Asp
                595                 600                 605

Phe Ile Tyr Glu Glu Glu Leu Gln Arg Phe Val Glu Ser Gly Ala Leu
                610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
                660                 665                 670

Arg Asp Val His Arg Ser Leu His Thr Ile Ala Gln Glu Gln Gly Ser
                675                 680                 685

Met Asp Ser Thr Lys Ala Glu Gly Phe Val Lys Asn Leu Gln Thr Ser
            690                 695                 700

Gly Arg Tyr Leu Arg Asp Val Trp
705                 710

<210> SEQ ID NO 39
<211> LENGTH: 713
<212> TYPE: PRT
<213> ORGANISM: Arabidopsis thaliana

<400> SEQUENCE: 39

Met Ala Ser Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
                20                  25                  30

Ala Ser Ala Tyr Glu Ser Val Ala Ala Glu Leu Ser Ser Met Leu Ile
            35                  40                  45

Glu Asn Arg Gln Phe Ala Met Ile Val Thr Thr Ser Ile Ala Val Leu
    50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu

```
                        85                  90                  95
Glu Glu Ile Asp Asp Gly Arg Lys Lys Val Thr Ile Phe Phe Gly Thr
                    100                 105                 110
Gln Thr Gly Thr Ala Glu Gly Phe Ala Lys Ala Leu Gly Glu Glu Ala
                115                 120                 125
Lys Ala Arg Tyr Glu Lys Thr Arg Phe Lys Ile Val Asp Leu Asp Asp
            130                 135                 140
Tyr Ala Asp Asp Asp Glu Tyr Glu Lys Leu Lys Lys Glu Asp
145                 150                 155                 160
Val Ala Phe Phe Phe Leu Ala Thr Tyr Gly Asp Gly Glu Pro Thr Asp
                165                 170                 175
Asn Ala Ala Arg Phe Tyr Lys Trp Phe Thr Glu Gly Asn Asp Arg Gly
                180                 185                 190
Glu Trp Leu Lys Asn Leu Lys Tyr Gly Val Phe Gly Leu Gly Asn Arg
                195                 200                 205
Gln Tyr Glu His Phe Asn Lys Val Ala Lys Val Val Asp Asp Ile Leu
                210                 215                 220
Val Glu Gln Gly Ala Gln Arg Leu Val Gln Val Gly Leu Gly Asp Asp
225                 230                 235                 240
Asp Gln Cys Ile Glu Asp Phe Thr Ala Trp Arg Glu Ala Leu Trp
                245                 250                 255
Pro Glu Leu Asp Thr Ile Leu Arg Glu Glu Gly Asp Thr Ala Val Ala
                260                 265                 270
Thr Pro Tyr Thr Ala Ala Val Leu Glu Tyr Arg Val Ser Ile His Asp
                275                 280                 285
Ser Glu Asp Ala Lys Phe Asn Asp Ile Thr Leu Ala Asn Gly Asn Gly
                290                 295                 300
Tyr Thr Val Phe Asp Ala Gln His Pro Tyr Lys Ala Asn Val Ala Val
305                 310                 315                 320
Lys Arg Glu Leu His Thr Pro Glu Ser Asp Arg Ser Cys Ile His Leu
                325                 330                 335
Glu Phe Asp Ile Ala Gly Ser Gly Leu Thr Met Lys Leu Gly Asp His
                340                 345                 350
Val Gly Val Leu Cys Asp Asn Leu Ser Glu Thr Val Asp Glu Ala Leu
                355                 360                 365
Arg Leu Leu Asp Met Ser Pro Asp Thr Tyr Phe Ser Leu His Ala Glu
                370                 375                 380
Lys Glu Asp Gly Thr Pro Ile Ser Ser Ser Leu Pro Pro Pro Phe Pro
385                 390                 395                 400
Pro Cys Asn Leu Arg Thr Ala Leu Thr Arg Tyr Ala Cys Leu Leu Ser
                405                 410                 415
Ser Pro Lys Lys Ser Ala Leu Val Ala Leu Ala Ala His Ala Ser Asp
                420                 425                 430
Pro Thr Glu Ala Glu Arg Leu Lys His Leu Ala Ser Pro Ala Gly Lys
                435                 440                 445
Asp Glu Tyr Ser Lys Trp Val Val Glu Ser Gln Arg Ser Leu Leu Glu
                450                 455                 460
Val Met Ala Glu Phe Pro Ser Ala Lys Pro Leu Gly Val Phe Phe
465                 470                 475                 480
Ala Gly Val Ala Pro Arg Leu Gln Pro Arg Phe Tyr Ser Ile Ser Ser
                485                 490                 495
Ser Pro Lys Ile Ala Glu Thr Arg Ile His Val Thr Cys Ala Leu Val
                500                 505                 510
```

-continued

```
Tyr Glu Lys Met Pro Thr Gly Arg Ile His Lys Gly Val Cys Ser Thr
            515                 520                 525

Trp Met Lys Asn Ala Val Pro Tyr Glu Lys Ser Glu Lys Leu Phe Leu
        530                 535                 540

Gly Arg Pro Ile Phe Val Arg Gln Ser Asn Phe Lys Leu Pro Ser Asp
545                 550                 555                 560

Ser Lys Val Pro Ile Ile Met Ile Gly Pro Gly Thr Gly Leu Ala Pro
                565                 570                 575

Phe Arg Gly Phe Leu Gln Glu Arg Leu Ala Leu Val Glu Ser Gly Val
            580                 585                 590

Glu Leu Gly Pro Ser Val Leu Phe Phe Gly Cys Arg Asn Arg Arg Met
        595                 600                 605

Asp Phe Ile Tyr Glu Glu Glu Leu Gln Arg Phe Val Glu Ser Gly Ala
    610                 615                 620

Leu Ala Glu Leu Ser Val Ala Phe Ser Arg Glu Gly Pro Thr Lys Glu
625                 630                 635                 640

Tyr Val Gln His Lys Met Met Asp Lys Ala Ser Asp Ile Trp Asn Met
                645                 650                 655

Ile Ser Gln Gly Ala Tyr Leu Tyr Val Cys Gly Asp Ala Lys Gly Met
            660                 665                 670

Ala Arg Asp Val His Arg Ser Leu His Thr Ile Ala Gln Glu Gln Gly
        675                 680                 685

Ser Met Asp Ser Thr Lys Ala Glu Gly Phe Val Lys Asn Leu Gln Thr
    690                 695                 700

Ser Gly Arg Tyr Leu Arg Asp Val Trp
705                 710

<210> SEQ ID NO 40
<211> LENGTH: 711
<212> TYPE: PRT
<213> ORGANISM: Stevia rebaudiana

<400> SEQUENCE: 40

Met Ala Gln Ser Asp Ser Val Lys Val Ser Pro Phe Asp Leu Val Ser
1               5                   10                  15

Ala Ala Met Asn Gly Lys Ala Met Glu Lys Leu Asn Ala Ser Glu Ser
            20                  25                  30

Glu Asp Pro Thr Thr Leu Pro Ala Leu Lys Met Leu Val Glu Asn Arg
        35                  40                  45

Glu Leu Leu Thr Leu Phe Thr Thr Ser Phe Ala Val Leu Ile Gly Cys
    50                  55                  60

Leu Val Phe Leu Met Trp Arg Arg Ser Ser Lys Lys Leu Val Gln
65                  70                  75                  80

Asp Pro Val Pro Gln Val Ile Val Lys Lys Glu Lys Glu Ser
                85                  90                  95

Glu Val Asp Asp Gly Lys Lys Val Ser Ile Phe Tyr Gly Thr Gln
                100                 105                 110

Thr Gly Thr Ala Glu Gly Phe Ala Lys Ala Leu Val Glu Ala Lys
            115                 120                 125

Val Arg Tyr Glu Lys Thr Ser Phe Lys Val Ile Asp Leu Asp Asp Tyr
        130                 135                 140

Ala Ala Asp Asp Asp Glu Tyr Glu Glu Lys Leu Lys Lys Glu Ser Leu
145                 150                 155                 160

Ala Phe Phe Phe Leu Ala Thr Tyr Gly Asp Gly Glu Pro Thr Asp Asn
```

```
                165                 170                 175
Ala Ala Asn Phe Tyr Lys Trp Phe Thr Glu Gly Asp Asp Lys Gly Glu
                180                 185                 190

Leu Leu Lys Lys Leu Gln Tyr Gly Val Phe Gly Leu Gly Asn Arg Gln
                195                 200                 205

Tyr Glu His Phe Asn Lys Ile Ala Ile Val Val Asp Asp Lys Leu Thr
            210                 215                 220

Glu Met Gly Ala Lys Arg Leu Pro Val Gly Leu Gly Asp Asp
225                 230                 235                 240

Gln Cys Ile Glu Asp Asp Phe Thr Ala Trp Lys Glu Leu Val Trp Pro
                    245                 250                 255

Glu Leu Asp Gln Leu Leu Arg Asp Glu Asp Thr Ser Val Thr Thr
                260                 265                 270

Pro Tyr Thr Ala Ala Val Leu Glu Tyr Arg Val Val Tyr His Asp Lys
                275                 280                 285

Pro Ala Asp Ser Tyr Ala Glu Asp Gln Thr His Thr Asn Gly His Val
            290                 295                 300

Val His Asp Ala Gln His Pro Ser Arg Ser Asn Val Ala Phe Lys Lys
305                 310                 315                 320

Glu Leu His Thr Ser Gln Ser Asp Arg Ser Cys Thr His Leu Glu Phe
                    325                 330                 335

Asp Ile Ser His Thr Gly Leu Ser Tyr Glu Thr Gly Asp His Val Gly
                340                 345                 350

Val Tyr Ser Glu Asn Leu Ser Glu Val Val Asp Glu Ala Leu Lys Leu
            355                 360                 365

Leu Gly Leu Ser Pro Asp Thr Tyr Phe Ser Val His Ala Asp Lys Glu
    370                 375                 380

Asp Gly Thr Pro Ile Gly Gly Ala Ser Leu Pro Pro Phe Pro Pro
385                 390                 395                 400

Cys Thr Leu Arg Asp Ala Leu Thr Arg Tyr Ala Asp Val Leu Ser Ser
                405                 410                 415

Pro Lys Lys Val Ala Leu Leu Ala Leu Ala Ala His Ala Ser Asp Pro
                420                 425                 430

Ser Glu Ala Asp Arg Leu Lys Phe Leu Ala Ser Pro Ala Gly Lys Asp
            435                 440                 445

Glu Tyr Ala Gln Trp Ile Val Ala Asn Gln Arg Ser Leu Leu Glu Val
    450                 455                 460

Met Gln Ser Phe Pro Ser Ala Lys Pro Pro Leu Gly Val Phe Phe Ala
465                 470                 475                 480

Ala Val Ala Pro Arg Leu Gln Pro Arg Tyr Tyr Ser Ile Ser Ser Ser
                485                 490                 495

Pro Lys Met Ser Pro Asn Arg Ile His Val Thr Cys Ala Leu Val Tyr
            500                 505                 510

Glu Thr Thr Pro Ala Gly Arg Ile His Arg Gly Leu Cys Ser Thr Trp
    515                 520                 525

Met Lys Asn Ala Val Pro Leu Thr Glu Ser Pro Asp Cys Ser Gln Ala
            530                 535                 540

Ser Ile Phe Val Arg Thr Ser Asn Phe Arg Leu Pro Val Asp Pro Lys
545                 550                 555                 560

Val Pro Val Ile Met Ile Gly Pro Gly Thr Gly Leu Ala Pro Phe Arg
                565                 570                 575

Gly Phe Leu Gln Glu Arg Leu Ala Leu Lys Glu Ser Gly Thr Glu Leu
            580                 585                 590
```

-continued

```
Gly Ser Ser Ile Phe Phe Phe Gly Cys Arg Asn Arg Lys Val Asp Phe
            595                 600                 605

Ile Tyr Glu Asp Glu Leu Asn Asn Phe Val Glu Thr Gly Ala Leu Ser
610                 615                 620

Glu Leu Ile Val Ala Phe Ser Arg Glu Gly Thr Ala Lys Glu Tyr Val
625                 630                 635                 640

Gln His Lys Met Ser Gln Lys Ala Ser Asp Ile Trp Lys Leu Leu Ser
            645                 650                 655

Glu Gly Ala Tyr Leu Tyr Val Cys Gly Asp Ala Lys Gly Met Ala Lys
            660                 665                 670

Asp Val His Arg Thr Leu His Thr Ile Val Gln Glu Gln Gly Ser Leu
            675                 680                 685

Asp Ser Ser Lys Ala Glu Leu Tyr Val Lys Asn Leu Gln Met Ser Gly
            690                 695                 700

Arg Tyr Leu Arg Asp Val Trp
705                 710

<210> SEQ ID NO 41
<211> LENGTH: 710
<212> TYPE: PRT
<213> ORGANISM: Stevia rebaudiana

<400> SEQUENCE: 41

Met Ala Gln Ser Glu Ser Val Glu Ala Ser Thr Ile Asp Leu Met Thr
1               5                   10                  15

Ala Val Leu Lys Asp Thr Val Ile Asp Thr Ala Asn Ala Ser Asp Asn
            20                  25                  30

Gly Asp Ser Lys Met Pro Pro Ala Leu Ala Met Met Phe Glu Ile Arg
        35                  40                  45

Asp Leu Leu Leu Ile Leu Thr Thr Ser Val Ala Val Leu Val Gly Cys
50                  55                  60

Phe Val Val Leu Val Trp Lys Arg Ser Ser Gly Lys Lys Ser Gly Lys
65                  70                  75                  80

Glu Leu Glu Pro Pro Lys Ile Val Val Pro Lys Arg Arg Leu Glu Gln
            85                  90                  95

Glu Val Asp Asp Gly Lys Lys Val Thr Ile Phe Phe Gly Thr Gln
            100                 105                 110

Thr Gly Thr Ala Glu Gly Phe Ala Lys Ala Leu Phe Glu Glu Ala Lys
        115                 120                 125

Ala Arg Tyr Glu Lys Ala Ala Phe Lys Val Ile Asp Leu Asp Asp Tyr
130                 135                 140

Ala Ala Asp Leu Asp Glu Tyr Ala Glu Lys Leu Lys Lys Glu Thr Tyr
145                 150                 155                 160

Ala Phe Phe Phe Leu Ala Thr Tyr Gly Asp Gly Glu Pro Thr Asp Asn
            165                 170                 175

Ala Ala Lys Phe Tyr Lys Trp Phe Thr Glu Gly Asp Glu Lys Gly Val
            180                 185                 190

Trp Leu Gln Lys Leu Gln Tyr Gly Val Phe Gly Leu Gly Asn Arg Gln
        195                 200                 205

Tyr Glu His Phe Asn Lys Ile Gly Ile Val Asp Asp Gly Leu Thr
    210                 215                 220

Glu Gln Gly Ala Lys Arg Ile Val Pro Val Gly Leu Gly Asp Asp Asp
225                 230                 235                 240

Gln Ser Ile Glu Asp Asp Phe Ser Ala Trp Lys Glu Leu Val Trp Pro
```

```
            245                 250                 255
Glu Leu Asp Leu Leu Arg Asp Glu Asp Lys Ala Ala Ala Thr
            260                 265                 270

Pro Tyr Thr Ala Ala Ile Pro Glu Tyr Arg Val Val Phe His Asp Lys
            275                 280                 285

Pro Asp Ala Phe Ser Asp His Thr Gln Thr Asn Gly His Ala Val
            290                 295                 300

His Asp Ala Gln His Pro Cys Arg Ser Asn Val Ala Val Lys Lys Glu
305                 310                 315                 320

Leu His Thr Pro Glu Ser Asp Arg Ser Cys Thr His Leu Glu Phe Asp
                325                 330                 335

Ile Ser His Thr Gly Leu Ser Tyr Glu Thr Gly Asp His Val Gly Val
                340                 345                 350

Tyr Cys Glu Asn Leu Ile Glu Val Val Glu Glu Ala Gly Lys Leu Leu
                355                 360                 365

Gly Leu Ser Thr Asp Thr Tyr Phe Ser Leu His Ile Asp Asn Glu Asp
        370                 375                 380

Gly Ser Pro Leu Gly Gly Pro Ser Leu Gln Pro Pro Phe Pro Pro Cys
385                 390                 395                 400

Thr Leu Arg Lys Ala Leu Thr Asn Tyr Ala Asp Leu Leu Ser Ser Pro
                405                 410                 415

Lys Lys Ser Thr Leu Leu Ala Leu Ala Ala His Ala Ser Asp Pro Thr
                420                 425                 430

Glu Ala Asp Arg Leu Arg Phe Leu Ala Ser Arg Glu Gly Lys Asp Glu
                435                 440                 445

Tyr Ala Glu Trp Val Val Ala Asn Gln Arg Ser Leu Leu Glu Val Met
        450                 455                 460

Glu Ala Phe Pro Ser Ala Arg Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Glu Pro Asn Arg Ile His Val Thr Cys Ala Leu Val Tyr Glu
                500                 505                 510

Lys Thr Pro Ala Gly Arg Ile His Lys Gly Ile Cys Ser Thr Trp Met
                515                 520                 525

Lys Asn Ala Val Pro Leu Thr Glu Ser Gln Asp Cys Ser Trp Ala Pro
        530                 535                 540

Ile Phe Val Arg Thr Ser Asn Phe Arg Leu Pro Ile Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Leu Phe Phe Gly Cys Arg Asn Arg Lys Val Asp Tyr Ile
                595                 600                 605

Tyr Glu Asn Glu Leu Asn Asn Phe Val Glu Asn Gly Ala Leu Ser Glu
        610                 615                 620

Leu Asp Val Ala Phe Ser Arg Asp Gly Pro Thr Lys Glu Tyr Val Gln
625                 630                 635                 640

His Lys Met Thr Gln Lys Ala Ser Glu Ile Trp Asn Met Leu Ser Glu
                645                 650                 655

Gly Ala Tyr Leu Tyr Val Cys Gly Asp Ala Lys Gly Met Ala Lys Asp
                660                 665                 670
```

Val His Arg Thr Leu His Thr Ile Val Gln Glu Gln Gly Ser Leu Asp
            675                 680                 685

Ser Ser Lys Ala Glu Leu Tyr Val Lys Asn Leu Gln Met Ser Gly Arg
    690                 695                 700

Tyr Leu Arg Asp Val Trp
705                 710

<210> SEQ ID NO 42
<211> LENGTH: 708
<212> TYPE: PRT
<213> ORGANISM: Stevia rebaudiana

<400> SEQUENCE: 42

Met Ala Gln Ser Asn Ser Val Lys Ile Ser Pro Leu Asp Leu Val Thr
1               5                   10                  15

Ala Leu Phe Ser Gly Lys Val Leu Asp Thr Ser Asn Ala Ser Glu Ser
            20                  25                  30

Gly Glu Ser Ala Met Leu Pro Thr Ile Ala Met Ile Met Glu Asn Arg
        35                  40                  45

Glu Leu Leu Met Ile Leu Thr Thr Ser Val Ala Val Leu Ile Gly Cys
    50                  55                  60

Val Val Leu Val Trp Arg Arg Ser Ser Thr Lys Lys Ser Ala Leu
65                  70                  75                  80

Glu Pro Pro Val Ile Val Pro Lys Arg Val Gln Glu Glu Glu Val
                85                  90                  95

Asp Asp Gly Lys Lys Lys Val Thr Val Phe Phe Gly Thr Gln Thr Gly
                100                 105                 110

Thr Ala Glu Gly Phe Ala Lys Ala Leu Val Glu Glu Ala Lys Ala Arg
            115                 120                 125

Tyr Glu Lys Ala Val Phe Lys Val Ile Asp Leu Asp Asp Tyr Ala Ala
        130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Asp Ala Lys Gly Glu Trp Leu
            180                 185                 190

Asn Lys Leu Gln Tyr Gly Val Phe Gly Leu Gly Asn Arg Gln Tyr Glu
        195                 200                 205

His Phe Asn Lys Ile Ala Lys Val Val Asp Asp Gly Leu Val Glu Gln
    210                 215                 220

Gly Ala Lys Arg Leu Val Pro Val Gly Leu Gly Asp Asp Gln Cys
225                 230                 235                 240

Ile Glu Asp Asp Phe Thr Ala Trp Lys Glu Leu Val Trp Pro Glu Leu
                245                 250                 255

Asp Gln Leu Leu Arg Asp Glu Asp Thr Thr Val Ala Thr Pro Tyr
            260                 265                 270

Thr Ala Ala Val Ala Glu Tyr Arg Val Val Phe His Glu Lys Pro Asp
        275                 280                 285

Ala Leu Ser Glu Asp Tyr Ser Tyr Thr Asn Gly His Ala Val His Asp
    290                 295                 300

Ala Gln His Pro Cys Arg Ser Asn Val Ala Val Lys Lys Glu Leu His
305                 310                 315                 320

Ser Pro Glu Ser Asp Arg Ser Cys Thr His Leu Glu Phe Asp Ile Ser

```
                325                 330                 335
Asn Thr Gly Leu Ser Tyr Glu Thr Gly Asp His Val Gly Val Tyr Cys
            340                 345                 350
Glu Asn Leu Ser Glu Val Val Asn Asp Ala Glu Arg Leu Val Gly Leu
            355                 360                 365
Pro Pro Asp Thr Tyr Phe Ser Ile His Thr Asp Ser Glu Asp Gly Ser
            370                 375                 380
Pro Leu Gly Gly Ala Ser Leu Pro Pro Phe Pro Pro Cys Thr Leu
385                 390                 395                 400
Arg Lys Ala Leu Thr Cys Tyr Ala Asp Val Leu Ser Ser Pro Lys Lys
            405                 410                 415
Ser Ala Leu Leu Ala Leu Ala Ala His Ala Thr Asp Pro Ser Glu Ala
            420                 425                 430
Asp Arg Leu Lys Phe Leu Ala Ser Pro Ala Gly Lys Asp Glu Tyr Ser
            435                 440                 445
Gln Trp Ile Val Ala Ser Gln Arg Ser Leu Leu Glu Val Met Glu Ala
            450                 455                 460
Phe Pro Ser Ala Lys Pro Ser Leu Gly Val Phe Phe Ala Ser Val Ala
465                 470                 475                 480
Pro Arg Leu Gln Pro Arg Tyr Tyr Ser Ile Ser Ser Pro Lys Met
            485                 490                 495
Ala Pro Asp Arg Ile His Val Thr Cys Ala Leu Val Tyr Glu Lys Thr
            500                 505                 510
Pro Ala Gly Arg Ile His Lys Gly Val Cys Ser Thr Trp Met Lys Asn
            515                 520                 525
Ala Val Pro Met Thr Glu Ser Gln Asp Cys Ser Trp Ala Pro Ile Tyr
            530                 535                 540
Val Arg Thr Ser Asn Phe Arg Leu Pro Ser Asp Pro Lys Val Pro Val
545                 550                 555                 560
Ile Met Ile Gly Pro Gly Thr Gly Leu Ala Pro Phe Arg Gly Phe Leu
            565                 570                 575
Gln Glu Arg Leu Ala Leu Lys Glu Ala Gly Thr Asp Leu Gly Leu Ser
            580                 585                 590
Ile Leu Phe Phe Gly Cys Arg Asn Arg Lys Val Asp Phe Ile Tyr Glu
            595                 600                 605
Asn Glu Leu Asn Asn Phe Val Glu Thr Gly Ala Leu Ser Glu Leu Ile
            610                 615                 620
Val Ala Phe Ser Arg Glu Gly Pro Thr Lys Glu Tyr Val Gln His Lys
625                 630                 635                 640
Met Ser Glu Lys Ala Ser Asp Ile Trp Asn Leu Leu Ser Glu Gly Ala
            645                 650                 655
Tyr Leu Tyr Val Cys Gly Asp Ala Lys Gly Met Ala Lys Asp Val His
            660                 665                 670
Arg Thr Leu His Thr Ile Val Gln Glu Gln Gly Ser Leu Asp Ser Ser
            675                 680                 685
Lys Ala Glu Leu Tyr Val Lys Asn Leu Gln Met Ser Gly Arg Tyr Leu
            690                 695                 700
Arg Asp Val Trp
705

<210> SEQ ID NO 43
<211> LENGTH: 706
<212> TYPE: PRT
<213> ORGANISM: Pelargonium graveolens
```

<400> SEQUENCE: 43

| | | | | | | | | | | | | | | |
|---|---|---|---|---|---|---|---|---|---|---|---|---|---|---|
| Met | Ala | Gln | Ser | Ser | Gly | Ser | Met | Ser | Pro | Phe | Asp | Phe | Met | Thr |
| 1 | | | | 5 | | | | | 10 | | | | | 15 |
| Ala | Ile | Ile | Lys | Gly | Lys | Met | Glu | Pro | Ser | Asn | Ala | Ser | Leu | Gly | Ala |
| | | | 20 | | | | | 25 | | | | | 30 | | |
| Ala | Gly | Glu | Val | Thr | Ala | Met | Ile | Leu | Asp | Asn | Arg | Glu | Leu | Val | Met |
| | | 35 | | | | | 40 | | | | | 45 | | | |
| Ile | Leu | Thr | Thr | Ser | Ile | Ala | Val | Leu | Ile | Gly | Cys | Val | Val | Val | Phe |
| | 50 | | | | | 55 | | | | | 60 | | | | |
| Ile | Trp | Arg | Arg | Ser | Ser | Ser | Gln | Thr | Pro | Thr | Ala | Val | Gln | Pro | Leu |
| 65 | | | | | 70 | | | | | 75 | | | | | 80 |
| Lys | Pro | Leu | Leu | Ala | Lys | Glu | Thr | Glu | Ser | Glu | Val | Asp | Asp | Gly | Lys |
| | | | | 85 | | | | | 90 | | | | | 95 | |
| Gln | Lys | Val | Thr | Ile | Phe | Phe | Gly | Thr | Gln | Thr | Gly | Thr | Ala | Glu | Gly |
| | | | 100 | | | | | 105 | | | | | 110 | | |
| Phe | Ala | Lys | Ala | Leu | Ala | Asp | Glu | Ala | Lys | Ala | Arg | Tyr | Asp | Lys | Val |
| | | | 115 | | | | | 120 | | | | | 125 | | |
| Thr | Phe | Lys | Val | Val | Asp | Leu | Asp | Asp | Tyr | Ala | Ala | Asp | Asp | Glu | Glu |
| | 130 | | | | | 135 | | | | | 140 | | | | |
| Tyr | Glu | Glu | Lys | Leu | Lys | Lys | Glu | Thr | Leu | Ala | Phe | Phe | Phe | Leu | Ala |
| 145 | | | | | 150 | | | | | 155 | | | | | 160 |
| Thr | Tyr | Gly | Asp | Gly | Glu | Pro | Thr | Asp | Asn | Ala | Ala | Arg | Phe | Tyr | Lys |
| | | | | 165 | | | | | 170 | | | | | 175 | |
| Trp | Phe | Leu | Glu | Gly | Lys | Glu | Arg | Gly | Glu | Trp | Leu | Gln | Asn | Leu | Lys |
| | | | 180 | | | | | 185 | | | | | 190 | | |
| Phe | Gly | Val | Phe | Gly | Leu | Gly | Asn | Arg | Gln | Tyr | Glu | His | Phe | Asn | Lys |
| | | 195 | | | | | 200 | | | | | 205 | | | |
| Ile | Ala | Ile | Val | Val | Asp | Glu | Ile | Leu | Ala | Glu | Gln | Gly | Gly | Lys | Arg |
| | 210 | | | | | 215 | | | | | 220 | | | | |
| Leu | Ile | Ser | Val | Gly | Leu | Gly | Asp | Asp | Gln | Cys | Ile | Glu | Asp | Asp |
| 225 | | | | | 230 | | | | | 235 | | | | | 240 |
| Phe | Thr | Ala | Trp | Arg | Glu | Ser | Leu | Trp | Pro | Glu | Leu | Asp | Gln | Leu | Leu |
| | | | | 245 | | | | | 250 | | | | | 255 | |
| Arg | Asp | Glu | Asp | Asp | Thr | Thr | Val | Ser | Thr | Pro | Tyr | Thr | Ala | Ala | Val |
| | | | 260 | | | | | 265 | | | | | 270 | | |
| Leu | Glu | Tyr | Arg | Val | Val | Phe | His | Asp | Pro | Ala | Asp | Ala | Pro | Thr | Leu |
| | | 275 | | | | | 280 | | | | | 285 | | | |
| Glu | Lys | Ser | Tyr | Ser | Asn | Ala | Asn | Gly | His | Ser | Val | Val | Asp | Ala | Gln |
| | 290 | | | | | 295 | | | | | 300 | | | | |
| His | Pro | Leu | Arg | Ala | Asn | Val | Ala | Val | Arg | Arg | Glu | Leu | His | Thr | Pro |
| 305 | | | | | 310 | | | | | 315 | | | | | 320 |
| Ala | Ser | Asp | Arg | Ser | Cys | Thr | His | Leu | Glu | Phe | Asp | Ile | Ser | Gly | Thr |
| | | | | 325 | | | | | 330 | | | | | 335 | |
| Gly | Ile | Ala | Tyr | Glu | Thr | Gly | Asp | His | Val | Gly | Val | Tyr | Cys | Glu | Asn |
| | | | 340 | | | | | 345 | | | | | 350 | | |
| Leu | Ala | Glu | Thr | Val | Glu | Glu | Ala | Leu | Glu | Leu | Leu | Gly | Leu | Ser | Pro |
| | | 355 | | | | | 360 | | | | | 365 | | | |
| Asp | Thr | Tyr | Phe | Ser | Val | His | Ala | Asp | Lys | Glu | Asp | Gly | Thr | Pro | Leu |
| | 370 | | | | | 375 | | | | | 380 | | | | |
| Ser | Gly | Ser | Ser | Leu | Pro | Pro | Phe | Pro | Pro | Cys | Thr | Leu | Arg | Thr |
| 385 | | | | | 390 | | | | | 395 | | | | | 400 |
| Ala | Leu | Thr | Leu | His | Ala | Asp | Leu | Leu | Ser | Ser | Pro | Lys | Lys | Ser | Ala |

```
                    405                 410                 415

Leu Leu Ala Leu Ala Ala His Ala Ser Asp Pro Thr Glu Ala Asp Arg
            420                 425                 430

Leu Arg His Leu Ala Ser Pro Ala Gly Lys Asp Glu Tyr Ala Gln Trp
        435                 440                 445

Ile Val Ala Ser Gln Arg Ser Leu Leu Glu Val Met Ala Glu Phe Pro
    450                 455                 460

Ser Ala Lys Pro Pro Leu Gly Val Phe Phe Ala Ser Val Ala Pro Arg
465                 470                 475                 480

Leu Gln Pro Arg Tyr Tyr Ser Ile Ser Ser Pro Arg Ile Ala Pro
            485                 490                 495

Ser Arg Ile His Val Thr Cys Ala Leu Val Tyr Glu Lys Thr Pro Thr
            500                 505                 510

Gly Arg Val His Lys Gly Val Cys Ser Thr Trp Met Lys Asn Ser Val
            515                 520                 525

Pro Ser Glu Lys Ser Asp Glu Cys Ser Trp Ala Pro Ile Phe Val Arg
        530                 535                 540

Gln Ser Asn Phe Lys Leu Pro Ala Asp Ala Lys Val Pro Ile Ile Met
545                 550                 555                 560

Ile Gly Pro Gly Thr Gly Leu Ala Pro Phe Arg Gly Phe Leu Gln Glu
                565                 570                 575

Arg Leu Ala Leu Lys Glu Ala Gly Thr Glu Leu Gly Pro Ser Ile Leu
            580                 585                 590

Phe Phe Gly Cys Arg Asn Ser Lys Met Asp Tyr Ile Tyr Glu Asp Glu
        595                 600                 605

Leu Asp Asn Phe Val Gln Asn Gly Ala Leu Ser Glu Leu Val Leu Ala
    610                 615                 620

Phe Ser Arg Glu Gly Pro Thr Lys Glu Tyr Val Gln His Lys Met Met
625                 630                 635                 640

Glu Lys Ala Ser Asp Ile Trp Asn Leu Ile Ser Gln Gly Ala Tyr Leu
                645                 650                 655

Tyr Val Cys Gly Asp Ala Lys Gly Met Ala Arg Asp Val His Arg Thr
            660                 665                 670

Leu His Thr Ile Ala Gln Glu Gln Gly Ser Leu Asp Ser Ser Lys Ala
        675                 680                 685

Glu Ser Met Val Lys Asn Leu Gln Met Ser Gly Arg Tyr Leu Arg Asp
    690                 695                 700

Val Trp
705

<210> SEQ ID NO 44
<211> LENGTH: 7
<212> TYPE: PRT
<213> ORGANISM: Artificial sequence
<220> FEATURE:
<223> OTHER INFORMATION: Synthetic sequence

<400> SEQUENCE: 44

Gly Ser Gly Gly Gly Gly Ser
1               5

<210> SEQ ID NO 45
<211> LENGTH: 8
<212> TYPE: PRT
<213> ORGANISM: Artificial sequence
<220> FEATURE:
<223> OTHER INFORMATION: Synthetic sequence
```

-continued

<400> SEQUENCE: 45

Gly Ser Gly Glu Ala Ala Ala Lys
1               5

<210> SEQ ID NO 46
<211> LENGTH: 13
<212> TYPE: PRT
<213> ORGANISM: Artificial sequence
<220> FEATURE:
<223> OTHER INFORMATION: Synthetic sequence

<400> SEQUENCE: 46

Gly Ser Gly Glu Ala Ala Ala Lys Glu Ala Ala Ala Lys
1               5                  10

<210> SEQ ID NO 47
<211> LENGTH: 9
<212> TYPE: PRT
<213> ORGANISM: Artificial sequence
<220> FEATURE:
<223> OTHER INFORMATION: Synthetic sequence

<400> SEQUENCE: 47

Gly Ser Gly Met Gly Ser Ser Ser Asn
1               5

<210> SEQ ID NO 48
<211> LENGTH: 491
<212> TYPE: PRT
<213> ORGANISM: Zingiber zerumbet

<400> SEQUENCE: 48

Leu Leu Ile Lys Arg Ser Ser Arg Ser Val His Lys Gln Gln Val
1               5                   10                  15

Leu Leu Ala Ser Leu Pro Pro Ser Pro Pro Arg Leu Pro Leu Ile Gly
                20                  25                  30

Asn Ile His Gln Leu Val Gly Gly Asn Pro His Arg Ile Leu Leu Gln
            35                  40                  45

Leu Ala Arg Thr His Gly Pro Leu Ile Cys Leu Arg Leu Gly Gln Val
        50                  55                  60

Asp Gln Val Val Ala Ser Ser Val Glu Ala Val Glu Glu Ile Ile Lys
65                  70                  75                  80

Arg His Asp Leu Lys Phe Ala Asp Arg Pro Arg Asp Leu Thr Phe Ser
                85                  90                  95

Arg Ile Phe Phe Tyr Asp Gly Asn Ala Val Val Met Thr Pro Tyr Gly
            100                 105                 110

Gly Glu Trp Lys Gln Met Arg Lys Ile Tyr Ala Met Glu Leu Leu Asn
        115                 120                 125

Ser Arg Arg Val Lys Ser Phe Ala Ala Ile Arg Glu Asp Val Ala Arg
    130                 135                 140

Lys Leu Thr Gly Glu Ile Ala His Lys Ala Phe Ala Gln Thr Pro Val
145                 150                 155                 160

Ile Asn Leu Ser Glu Met Val Met Ser Met Ile Asn Ala Ile Val Ile
                165                 170                 175

Arg Val Ala Phe Gly Asp Lys Cys Lys Gln Gln Ala Tyr Phe Leu His
            180                 185                 190

Leu Val Lys Glu Ala Met Ser Tyr Val Ser Ser Phe Val Ala Asp
        195                 200                 205

```
Met Tyr Pro Ser Leu Lys Phe Leu Asp Thr Leu Thr Gly Leu Lys Ser
    210                 215                 220

Lys Leu Glu Gly Val His Gly Lys Leu Asp Lys Val Phe Asp Glu Ile
225                 230                 235                 240

Ile Ala Gln Arg Gln Ala Ala Leu Ala Ala Glu Gln Ala Gly Glu Asp
                245                 250                 255

Leu Ile Ile Asp Val Leu Leu Lys Leu Lys Asp Glu Gly Asn Gln Glu
                260                 265                 270

Phe Pro Ile Thr Tyr Thr Ser Val Lys Ala Ile Val Met Glu Ile Phe
                275                 280                 285

Leu Ala Gly Thr Glu Thr Ser Ser Ser Val Ile Asp Trp Val Met Ser
    290                 295                 300

Glu Leu Ile Lys Asn Pro Lys Ala Met Glu Lys Val Gln Lys Glu Met
305                 310                 315                 320

Arg Glu Ala Met Gln Gly Lys Thr Lys Leu Glu Glu Ser Asp Ile Pro
                325                 330                 335

Lys Phe Ser Tyr Leu Asn Leu Val Ile Lys Glu Thr Leu Arg Leu His
                340                 345                 350

Pro Pro Gly Pro Leu Leu Phe Pro Arg Glu Cys Arg Glu Thr Cys Glu
    355                 360                 365

Val Met Gly Tyr Arg Val Pro Ala Gly Ala Arg Leu Leu Ile Asn Ala
    370                 375                 380

Phe Ala Leu Ser Arg Asp Glu Lys Tyr Trp Gly Ser Asp Ala Glu Ser
385                 390                 395                 400

Phe Lys Pro Glu Arg Phe Glu Gly Ile Ser Val Asp Phe Lys Gly Ser
                405                 410                 415

Asn Phe Glu Phe Met Pro Phe Gly Ala Gly Arg Arg Ile Cys Pro Gly
                420                 425                 430

Met Thr Phe Gly Ile Ser Ser Val Glu Val Ala Leu Ala His Leu Leu
                435                 440                 445

Phe His Phe Asp Trp Gln Leu Pro Gln Gly Met Lys Ile Glu Asp Leu
    450                 455                 460

Asp Met Met Glu Val Ser Gly Met Ser Ala Thr Arg Arg Ser Pro Leu
465                 470                 475                 480

Leu Val Leu Ala Lys Leu Ile Ile Pro Leu Pro
                485                 490

<210> SEQ ID NO 49
<211> LENGTH: 476
<212> TYPE: PRT
<213> ORGANISM: Barnadesia spinosa

<400> SEQUENCE: 49

Leu Leu Thr Gly Ser Lys Ser Thr Lys Asn Ser Leu Pro Glu Ala Trp
1               5                   10                  15

Arg Leu Pro Ile Ile Gly His Met His His Leu Val Gly Thr Leu Pro
                20                  25                  30

His Arg Gly Val Thr Asp Met Ala Arg Lys Tyr Gly Ser Leu Met His
            35                  40                  45

Leu Gln Leu Gly Glu Val Ser Thr Ile Val Val Ser Ser Pro Arg Trp
    50                  55                  60

Ala Lys Glu Val Leu Thr Thr Tyr Asp Ile Thr Phe Ala Asn Arg Pro
65              70                  75                  80

Glu Thr Leu Thr Gly Glu Ile Val Ala Tyr His Asn Thr Asp Ile Val
                85                  90                  95
```

```
Leu Ser Pro Tyr Gly Glu Tyr Trp Arg Gln Leu Arg Lys Leu Cys Thr
                100                 105                 110

Leu Glu Leu Leu Ser Ala Lys Lys Val Lys Ser Phe Gln Ser Leu Arg
            115                 120                 125

Glu Glu Glu Cys Trp Asn Leu Val Lys Glu Val Arg Ser Ser Gly Ser
130                 135                 140

Gly Ser Pro Val Asp Leu Ser Glu Ser Ile Phe Lys Leu Ile Ala Thr
145                 150                 155                 160

Ile Leu Ser Arg Ala Ala Phe Gly Lys Gly Ile Lys Asp Gln Arg Glu
                165                 170                 175

Phe Thr Glu Ile Val Lys Glu Ile Leu Arg Leu Thr Gly Gly Phe Asp
            180                 185                 190

Val Ala Asp Ile Phe Pro Ser Lys Lys Ile Leu His His Leu Ser Gly
            195                 200                 205

Lys Arg Ala Lys Leu Thr Asn Ile His Asn Lys Leu Asp Ser Leu Ile
210                 215                 220

Asn Asn Ile Val Ser Glu His Pro Gly Ser Arg Thr Ser Ser Ser Gln
225                 230                 235                 240

Glu Ser Leu Leu Asp Val Leu Leu Arg Leu Lys Asp Ser Ala Glu Leu
                245                 250                 255

Pro Leu Thr Ser Asp Asn Val Lys Ala Val Ile Leu Asp Met Phe Gly
            260                 265                 270

Ala Gly Thr Asp Thr Ser Ser Ala Thr Ile Glu Trp Ala Ile Ser Glu
            275                 280                 285

Leu Ile Arg Cys Pro Arg Ala Met Glu Lys Val Gln Thr Glu Leu Arg
            290                 295                 300

Gln Ala Leu Asn Gly Lys Glu Arg Ile Gln Glu Asp Ile Gln Glu
305                 310                 315                 320

Leu Ser Tyr Leu Lys Leu Val Ile Lys Glu Thr Leu Arg Leu His Pro
                325                 330                 335

Pro Leu Pro Leu Val Met Pro Arg Glu Cys Arg Glu Pro Cys Val Leu
            340                 345                 350

Ala Gly Tyr Glu Ile Pro Thr Lys Thr Lys Leu Ile Val Asn Val Phe
            355                 360                 365

Ala Ile Asn Arg Asp Pro Glu Tyr Trp Lys Asp Ala Glu Thr Phe Met
370                 375                 380

Pro Glu Arg Phe Glu Asn Ser Pro Ile Asn Ile Met Gly Ser Glu Tyr
385                 390                 395                 400

Glu Tyr Leu Pro Phe Gly Ala Gly Arg Arg Met Cys Pro Gly Ala Ala
                405                 410                 415

Leu Gly Leu Ala Asn Val Glu Leu Pro Leu Ala His Ile Leu Tyr Tyr
            420                 425                 430

Phe Asn Trp Lys Leu Pro Asn Gly Ala Arg Leu Asp Glu Leu Asp Met
435                 440                 445

Ser Glu Cys Phe Gly Ala Thr Val Gln Arg Lys Ser Glu Leu Leu Leu
            450                 455                 460

Val Pro Thr Ala Tyr Lys Thr Ala Asn Asn Ser Ala
465                 470                 475

<210> SEQ ID NO 50
<211> LENGTH: 486
<212> TYPE: PRT
<213> ORGANISM: Hyoscyamus muticus
```

<400> SEQUENCE: 50

```
Phe Leu Leu Arg Lys Trp Lys Asn Ser Asn Ser Gln Ser Lys Lys Leu
1               5                   10                  15
Pro Pro Gly Pro Trp Lys Leu Pro Leu Leu Gly Ser Met Leu His Met
            20                  25                  30
Val Gly Gly Leu Pro His His Val Leu Arg Asp Leu Ala Lys Lys Tyr
        35                  40                  45
Gly Pro Leu Met His Leu Gln Leu Gly Glu Val Ser Ala Val Val Val
    50                  55                  60
Thr Ser Pro Asp Met Ala Lys Glu Val Leu Lys Thr His Asp Ile Ala
65                  70                  75                  80
Phe Ala Ser Arg Pro Lys Leu Leu Ala Pro Glu Ile Val Cys Tyr Asn
                85                  90                  95
Arg Ser Asp Ile Ala Phe Cys Pro Tyr Gly Asp Tyr Trp Arg Gln Met
            100                 105                 110
Arg Lys Ile Cys Val Leu Glu Val Leu Ser Ala Lys Asn Val Arg Ser
        115                 120                 125
Phe Ser Ser Ile Arg Arg Asp Glu Val Leu Arg Leu Val Asn Phe Val
    130                 135                 140
Arg Ser Ser Thr Ser Glu Pro Val Asn Phe Thr Glu Arg Leu Phe Leu
145                 150                 155                 160
Phe Thr Ser Ser Met Thr Cys Arg Ser Ala Phe Gly Lys Val Phe Lys
                165                 170                 175
Glu Gln Glu Thr Phe Ile Gln Leu Ile Lys Glu Val Ile Gly Leu Ala
            180                 185                 190
Gly Gly Phe Asp Val Ala Asp Ile Phe Pro Ser Leu Lys Phe Leu His
        195                 200                 205
Val Leu Thr Gly Met Glu Gly Lys Ile Met Lys Ala His His Lys Val
    210                 215                 220
Asp Ala Ile Val Glu Asp Val Ile Asn Glu His Lys Lys Asn Leu Ala
225                 230                 235                 240
Met Gly Lys Thr Asn Gly Ala Leu Gly Gly Glu Asp Leu Ile Asp Val
                245                 250                 255
Leu Leu Arg Leu Met Asn Asp Gly Gly Leu Gln Phe Pro Ile Thr Asn
            260                 265                 270
Asp Asn Ile Lys Ala Ile Ile Phe Asp Met Phe Ala Ala Gly Thr Glu
        275                 280                 285
Thr Ser Ser Ser Thr Leu Val Trp Ala Met Val Gln Met Met Arg Asn
    290                 295                 300
Pro Thr Ile Leu Ala Lys Ala Gln Ala Glu Val Arg Glu Ala Phe Lys
305                 310                 315                 320
Gly Lys Glu Thr Phe Asp Glu Asn Asp Val Glu Glu Leu Lys Tyr Leu
                325                 330                 335
Lys Leu Val Ile Lys Glu Thr Leu Arg Leu His Pro Val Pro Leu
            340                 345                 350
Leu Val Pro Arg Glu Cys Arg Glu Glu Thr Glu Ile Asn Gly Tyr Thr
        355                 360                 365
Ile Pro Val Lys Thr Lys Val Met Val Asn Val Trp Ala Leu Gly Arg
    370                 375                 380
Asp Pro Lys Tyr Trp Asp Asp Ala Asp Asn Phe Lys Pro Glu Arg Phe
385                 390                 395                 400
Glu Gln Cys Ser Val Asp Phe Ile Gly Asn Asn Phe Glu Tyr Leu Pro
                405                 410                 415
```

-continued

```
Phe Gly Gly Gly Arg Arg Ile Cys Pro Gly Ile Ser Phe Gly Leu Ala
            420                 425                 430

Asn Val Tyr Leu Pro Leu Ala Gln Leu Leu Tyr His Phe Asp Trp Lys
        435                 440                 445

Leu Pro Thr Gly Met Glu Pro Lys Asp Leu Asp Leu Thr Glu Leu Val
450                 455                 460

Gly Val Thr Ala Ala Arg Lys Ser Asp Leu Met Leu Val Ala Thr Pro
465                 470                 475                 480

Tyr Gln Pro Ser Arg Glu
                485

<210> SEQ ID NO 51
<211> LENGTH: 469
<212> TYPE: PRT
<213> ORGANISM: Lactuca sativa

<400> SEQUENCE: 51

Lys Leu Ala Thr Arg Pro Lys Ser Thr Lys Gln Leu Pro Glu Ala
1               5                  10                  15

Ser Arg Leu Pro Ile Ile Gly His Met His His Leu Ile Gly Thr Met
            20                  25                  30

Pro His Arg Gly Val Met Asp Leu Ala Arg Lys His Gly Ser Leu Met
        35                  40                  45

His Leu Gln Leu Gly Glu Val Ser Thr Ile Val Val Ser Ser Pro Lys
    50                  55                  60

Trp Ala Lys Glu Ile Leu Thr Thr Tyr Asp Ile Thr Phe Ala Asn Arg
65                  70                  75                  80

Pro Glu Thr Leu Thr Gly Glu Ile Ile Ala Tyr His Asn Thr Asp Ile
                85                  90                  95

Val Leu Ala Pro Tyr Gly Glu Tyr Trp Arg Gln Leu Arg Lys Leu Cys
            100                 105                 110

Thr Leu Glu Leu Leu Ser Val Lys Lys Val Lys Ser Phe Gln Ser Ile
        115                 120                 125

Arg Glu Glu Glu Cys Trp Asn Leu Val Lys Glu Val Lys Glu Ser Gly
130                 135                 140

Ser Gly Lys Pro Ile Asn Leu Ser Glu Ser Ile Phe Thr Met Ile Ala
145                 150                 155                 160

Thr Ile Leu Ser Arg Ala Ala Phe Gly Lys Gly Ile Lys Asp Gln Arg
                165                 170                 175

Glu Phe Thr Glu Ile Val Lys Glu Ile Leu Arg Gln Thr Gly Gly Phe
            180                 185                 190

Asp Val Ala Asp Ile Phe Pro Ser Lys Lys Phe Leu His His Leu Ser
        195                 200                 205

Gly Lys Arg Ala Arg Leu Thr Ser Ile His Lys Lys Leu Asp Asn Leu
    210                 215                 220

Ile Asn Asn Ile Val Ala Glu His His Val Ser Thr Ser Ser Lys Ala
225                 230                 235                 240

Asn Glu Thr Leu Leu Asp Val Leu Leu Arg Leu Lys Asp Ser Ala Glu
                245                 250                 255

Phe Pro Leu Thr Ala Asp Asn Val Lys Ala Ile Ile Leu Asp Met Phe
            260                 265                 270

Gly Ala Gly Thr Asp Thr Ser Ser Ala Thr Val Glu Trp Ala Ile Ser
        275                 280                 285

Glu Leu Ile Arg Cys Pro Arg Ala Met Glu Lys Val Gln Ala Glu Leu
```

```
                290                 295                 300
Arg Gln Ala Leu Asn Gly Lys Glu Lys Ile Gln Glu Glu Asp Ile Gln
305                 310                 315                 320

Asp Leu Ala Tyr Leu Asn Leu Val Ile Arg Glu Thr Leu Arg Leu His
                325                 330                 335

Pro Pro Leu Pro Leu Val Met Pro Arg Glu Cys Arg Glu Pro Val Asn
                340                 345                 350

Leu Ala Gly Tyr Glu Ile Ala Asn Lys Thr Lys Leu Ile Val Asn Val
                355                 360                 365

Phe Ala Ile Asn Arg Asp Pro Glu Tyr Trp Lys Asp Ala Glu Ala Phe
                370                 375                 380

Ile Pro Glu Arg Phe Glu Asn Asn Pro Asn Asn Ile Met Gly Ala Asp
385                 390                 395                 400

Tyr Glu Tyr Leu Pro Phe Gly Ala Gly Arg Arg Met Cys Pro Gly Ala
                405                 410                 415

Ala Leu Gly Leu Ala Asn Val Gln Leu Pro Leu Ala Asn Ile Leu Tyr
                420                 425                 430

His Phe Asn Trp Lys Leu Pro Asn Gly Ala Ser His Asp Gln Leu Asp
                435                 440                 445

Met Thr Glu Ser Phe Gly Ala Thr Val Gln Arg Lys Thr Glu Leu Leu
                450                 455                 460

Leu Val Pro Ser Phe
465

<210> SEQ ID NO 52
<211> LENGTH: 488
<212> TYPE: PRT
<213> ORGANISM: Nicotiani tabacum

<400> SEQUENCE: 52

Phe Leu Leu Arg Lys Trp Lys Asn Ser Asn Ser Gln Ser Lys Lys Leu
1               5                   10                  15

Pro Pro Gly Pro Trp Lys Ile Pro Ile Leu Gly Ser Met Leu His Met
                20                  25                  30

Ile Gly Gly Glu Pro His His Val Leu Arg Asp Leu Ala Lys Lys Tyr
                35                  40                  45

Gly Pro Leu Met His Leu Gln Leu Gly Glu Ile Ser Ala Val Val Val
            50                  55                  60

Thr Ser Arg Asp Met Ala Lys Glu Val Leu Lys Thr His Asp Val Val
65              70                  75                  80

Phe Ala Ser Arg Pro Lys Ile Val Ala Met Asp Ile Ile Cys Tyr Asn
                85                  90                  95

Gln Ser Asp Ile Ala Phe Ser Pro Tyr Gly Asp His Trp Arg Gln Met
                100                 105                 110

Arg Lys Ile Cys Val Met Glu Leu Leu Asn Ala Lys Asn Val Arg Ser
            115                 120                 125

Phe Ser Ser Ile Arg Arg Asp Glu Val Val Arg Leu Ile Asp Ser Ile
130                 135                 140

Arg Ser Asp Ser Ser Gly Glu Leu Val Asn Phe Thr Gln Arg Ile
145                 150                 155                 160

Ile Trp Phe Ala Ser Ser Met Thr Cys Arg Ser Ala Phe Gly Gln Val
                165                 170                 175

Leu Lys Gly Gln Asp Ile Phe Ala Lys Lys Ile Arg Glu Val Ile Gly
                180                 185                 190
```

```
Leu Ala Glu Gly Phe Asp Val Asp Ile Phe Pro Thr Tyr Lys Phe
            195                 200                 205

Leu His Val Leu Ser Gly Met Lys Arg Lys Leu Leu Asn Ala His Leu
210                 215                 220

Lys Val Asp Ala Ile Val Glu Asp Val Ile Asn Glu His Lys Lys Asn
225                 230                 235                 240

Leu Ala Ala Gly Lys Ser Asn Gly Ala Leu Gly Gly Glu Asp Leu Ile
            245                 250                 255

Asp Val Leu Leu Arg Leu Met Asn Asp Thr Ser Leu Gln Phe Pro Ile
            260                 265                 270

Thr Asn Asp Asn Ile Lys Ala Val Ile Val Asp Met Phe Ala Ala Gly
            275                 280                 285

Thr Glu Thr Ser Ser Thr Thr Thr Val Trp Ala Met Ala Glu Met Met
    290                 295                 300

Lys Asn Pro Ser Val Phe Thr Lys Ala Gln Ala Glu Val Arg Glu Ala
305                 310                 315                 320

Phe Arg Asp Lys Val Ser Phe Asp Glu Asn Asp Val Glu Glu Leu Lys
                325                 330                 335

Tyr Leu Lys Leu Val Ile Lys Glu Thr Leu Arg Leu His Pro Pro Ser
            340                 345                 350

Pro Leu Leu Val Pro Arg Glu Cys Arg Glu Asp Thr Asp Ile Asn Gly
            355                 360                 365

Tyr Thr Ile Pro Ala Lys Thr Lys Val Met Val Asn Val Trp Ala Leu
    370                 375                 380

Gly Arg Asp Pro Lys Tyr Trp Asp Asp Ala Glu Ser Phe Lys Pro Glu
385                 390                 395                 400

Arg Phe Glu Gln Cys Ser Val Asp Phe Phe Gly Asn Asn Phe Glu Phe
                405                 410                 415

Leu Pro Phe Gly Gly Gly Arg Arg Ile Cys Pro Gly Met Ser Phe Gly
            420                 425                 430

Leu Ala Asn Leu Tyr Leu Pro Leu Ala Gln Leu Leu Tyr His Phe Asp
            435                 440                 445

Trp Lys Leu Pro Thr Gly Ile Met Pro Arg Asp Leu Asp Leu Thr Glu
450                 455                 460

Leu Ser Gly Ile Thr Ile Ala Arg Lys Gly Gly Leu Tyr Leu Asn Ala
465                 470                 475                 480

Thr Pro Tyr Gln Pro Ser Arg Glu
            485

<210> SEQ ID NO 53
<211> LENGTH: 496
<212> TYPE: PRT
<213> ORGANISM: Citrus x paradisi

<400> SEQUENCE: 53

Trp Val Trp Leu Arg Pro Lys Lys Leu Glu Lys Phe Leu Arg Gln Gln
1               5                   10                  15

Gly Leu Lys Gly Asn Ser Tyr Arg Leu Leu Phe Gly Asp Leu Lys Glu
            20                  25                  30

Asn Ser Ile Glu Leu Lys Glu Ala Lys Ala Arg Pro Leu Ser Leu Asp
        35                  40                  45

Asp Asp Ile Ala Ile Arg Val Asn Pro Phe Leu His Lys Leu Val Asn
    50                  55                  60

Asp Tyr Gly Lys Asn Ser Phe Met Trp Phe Gly Pro Thr Pro Arg Val
65                  70                  75                  80
```

```
Asn Ile Met Asn Pro Asp Gln Ile Lys Ala Ile Phe Thr Lys Ile Asn
                85                  90                  95
Asp Phe Gln Lys Val Asn Ser Ile Pro Leu Ala Arg Leu Leu Ile Val
            100                 105                 110
Gly Leu Ala Thr Leu Glu Gly Glu Lys Trp Ala Lys His Arg Lys Leu
        115                 120                 125
Ile Asn Pro Ala Phe His Gln Glu Lys Leu Lys Leu Met Leu Pro Ala
    130                 135                 140
Phe Tyr Leu Ser Cys Ile Glu Ile Ile Thr Lys Trp Glu Lys Gln Met
145                 150                 155                 160
Ser Val Glu Gly Ser Ser Glu Leu Asp Val Trp Pro Tyr Leu Ala Asn
                165                 170                 175
Leu Thr Ser Asp Val Ile Ser Arg Thr Ala Phe Gly Ser Ser Tyr Glu
            180                 185                 190
Glu Gly Arg Arg Ile Phe Gln Leu Gln Ala Glu Leu Ala Glu Leu Thr
        195                 200                 205
Met Gln Val Phe Arg Ser Val His Ile Pro Gly Trp Arg Phe Leu Pro
    210                 215                 220
Thr Lys Arg Asn Arg Arg Met Lys Glu Ile Asp Lys Glu Ile Arg Ala
225                 230                 235                 240
Ser Leu Met Gly Ile Ile Lys Asn Arg Glu Lys Ala Met Arg Ala Gly
                245                 250                 255
Glu Ala Ala Asn Asn Asp Leu Leu Gly Ile Leu Met Glu Thr Ser Phe
            260                 265                 270
Arg Glu Ile Glu Glu His Gly Asn Asn Lys Asn Val Gly Phe Ser Met
        275                 280                 285
Asn Asp Val Ile Glu Glu Cys Lys Leu Phe Tyr Phe Ala Gly Gln Glu
    290                 295                 300
Thr Thr Ser Val Leu Leu Asn Trp Thr Met Val Leu Leu Ser Lys His
305                 310                 315                 320
Gln Asp Trp Gln Glu Arg Ala Arg Gln Glu Val Leu Gln Val Phe Gly
                325                 330                 335
Asn Asn Lys Pro Asp Tyr Asp Gly Leu Asn His Leu Lys Ile Val Gln
            340                 345                 350
Met Ile Leu Tyr Glu Val Leu Arg Leu Tyr Pro Pro Val Thr Val Leu
        355                 360                 365
Ser Arg Ala Val Phe Lys Glu Thr Lys Leu Gly Asn Leu Thr Leu Pro
    370                 375                 380
Ala Gly Val Gln Ile Gly Leu Pro Met Ile Leu Val His Gln Asp Pro
385                 390                 395                 400
Glu Leu Trp Gly Asp Asp Ala Val Glu Phe Lys Pro Glu Arg Phe Ala
                405                 410                 415
Glu Gly Ile Ser Lys Ala Ala Lys Asn Gln Val Ser Tyr Phe Pro Phe
            420                 425                 430
Ala Leu Gly Pro Arg Ile Cys Val Gly Gln Asn Phe Ala Leu Val Glu
        435                 440                 445
Ala Lys Met Ala Thr Ala Met Ile Leu Gln Asn Tyr Ser Phe Glu Leu
    450                 455                 460
Ser Pro Ser Tyr Val His Ala Pro Thr Ala Val Pro Thr Leu His Pro
465                 470                 475                 480
Glu Leu Gly Thr Gln Leu Ile Leu Arg Lys Leu Trp Cys Lys Asn Asn
                485                 490                 495
```

<210> SEQ ID NO 54
<211> LENGTH: 472
<212> TYPE: PRT
<213> ORGANISM: Artemesia annua

<400> SEQUENCE: 54

```
Phe Val Tyr Lys Phe Ala Thr Arg Ser Lys Ser Thr Lys Lys Ser Leu
1               5                   10                  15

Pro Glu Pro Trp Arg Leu Pro Ile Ile Gly His Met His His Leu Ile
            20                  25                  30

Gly Thr Thr Pro His Arg Gly Val Arg Asp Leu Ala Arg Lys Tyr Gly
        35                  40                  45

Ser Leu Met His Leu Gln Leu Gly Glu Val Pro Thr Ile Val Val Ser
    50                  55                  60

Ser Pro Lys Trp Ala Lys Glu Ile Leu Thr Thr Tyr Asp Ile Thr Phe
65                  70                  75                  80

Ala Asn Arg Pro Glu Thr Leu Thr Gly Glu Ile Val Leu Tyr His Asn
                85                  90                  95

Thr Asp Val Val Leu Ala Pro Tyr Gly Glu Tyr Trp Arg Gln Leu Arg
            100                 105                 110

Lys Ile Cys Thr Leu Glu Leu Leu Ser Val Lys Val Lys Ser Phe
        115                 120                 125

Gln Ser Leu Arg Glu Glu Glu Cys Trp Asn Leu Val Gln Glu Ile Lys
    130                 135                 140

Ala Ser Gly Ser Gly Arg Pro Val Asn Leu Ser Glu Asn Val Phe Lys
145                 150                 155                 160

Leu Ile Ala Thr Ile Leu Ser Arg Ala Ala Phe Gly Lys Gly Ile Lys
                165                 170                 175

Asp Gln Lys Glu Leu Thr Glu Ile Val Lys Glu Ile Leu Arg Gln Thr
            180                 185                 190

Gly Gly Phe Asp Val Ala Asp Ile Phe Pro Ser Lys Lys Phe Leu His
        195                 200                 205

His Leu Ser Gly Lys Arg Ala Arg Leu Thr Ser Leu Arg Lys Lys Ile
    210                 215                 220

Asp Asn Leu Ile Asp Asn Leu Val Ala Glu His Thr Val Asn Thr Ser
225                 230                 235                 240

Ser Lys Thr Asn Glu Thr Leu Leu Asp Val Leu Leu Arg Leu Lys Asp
                245                 250                 255

Ser Ala Glu Phe Pro Leu Thr Ser Asp Asn Ile Lys Ala Ile Ile Leu
            260                 265                 270

Asp Met Phe Gly Ala Gly Thr Asp Thr Ser Ser Ser Thr Ile Glu Trp
        275                 280                 285

Ala Ile Ser Glu Leu Ile Lys Cys Pro Lys Ala Met Glu Lys Val Gln
    290                 295                 300

Ala Glu Leu Arg Lys Ala Leu Asn Gly Lys Glu Lys Ile His Glu Glu
305                 310                 315                 320

Asp Ile Gln Glu Leu Ser Tyr Leu Asn Met Val Ile Lys Glu Thr Leu
                325                 330                 335

Arg Leu His Pro Pro Leu Pro Leu Val Leu Pro Arg Glu Cys Arg Gln
            340                 345                 350

Pro Val Asn Leu Ala Gly Tyr Asn Ile Pro Asn Lys Thr Lys Leu Ile
        355                 360                 365

Val Asn Val Phe Ala Ile Asn Arg Asp Pro Glu Tyr Trp Lys Asp Ala
    370                 375                 380
```

```
Glu Ala Phe Ile Pro Glu Arg Phe Glu Asn Ser Ser Ala Thr Val Met
385                 390                 395                 400

Gly Ala Glu Tyr Glu Tyr Leu Pro Phe Gly Ala Gly Arg Arg Met Cys
            405                 410                 415

Pro Gly Ala Ala Leu Gly Leu Ala Asn Val Gln Leu Pro Leu Ala Asn
            420                 425                 430

Ile Leu Tyr His Phe Asn Trp Lys Leu Pro Asn Gly Val Ser Tyr Asp
            435                 440                 445

Gln Ile Asp Met Thr Glu Ser Ser Gly Ala Thr Met Gln Arg Lys Thr
        450                 455                 460

Glu Leu Leu Leu Val Pro Ser Phe
465                 470

<210> SEQ ID NO 55
<211> LENGTH: 488
<212> TYPE: PRT
<213> ORGANISM: Arabidopsis thaliana

<400> SEQUENCE: 55

Phe Phe Phe Lys Lys Leu Leu Ser Phe Ser Arg Lys Asn Met Ser Glu
1               5                   10                  15

Val Ser Thr Leu Pro Ser Val Pro Val Pro Gly Phe Pro Val Ile
            20                  25                  30

Gly Asn Leu Leu Gln Leu Lys Glu Lys Lys Pro His Lys Thr Phe Thr
            35                  40                  45

Arg Trp Ser Glu Ile Tyr Gly Pro Ile Tyr Ser Ile Lys Met Gly Ser
50                  55                  60

Ser Ser Leu Ile Val Leu Asn Ser Thr Glu Thr Ala Lys Glu Ala Met
65                  70                  75                  80

Val Thr Arg Phe Ser Ser Ile Ser Thr Arg Lys Leu Ser Asn Ala Leu
                85                  90                  95

Thr Val Leu Thr Cys Asp Lys Ser Met Val Ala Thr Ser Asp Tyr Asp
            100                 105                 110

Asp Phe His Lys Leu Val Lys Arg Cys Leu Leu Asn Gly Leu Leu Gly
            115                 120                 125

Ala Asn Ala Gln Lys Arg Lys Arg His Tyr Arg Asp Ala Leu Ile Glu
            130                 135                 140

Asn Val Ser Ser Lys Leu His Ala His Ala Arg Asp His Pro Gln Glu
145                 150                 155                 160

Pro Val Asn Phe Arg Ala Ile Phe Glu His Glu Leu Phe Gly Val Ala
                165                 170                 175

Leu Lys Gln Ala Phe Gly Lys Asp Val Glu Ser Ile Tyr Val Lys Glu
            180                 185                 190

Leu Gly Val Thr Leu Ser Lys Asp Glu Ile Phe Lys Val Leu Val His
        195                 200                 205

Asp Met Met Glu Gly Ala Ile Asp Val Asp Trp Arg Asp Phe Phe Pro
        210                 215                 220

Tyr Leu Lys Trp Ile Pro Asn Lys Ser Phe Glu Ala Arg Ile Gln Gln
225                 230                 235                 240

Lys His Lys Arg Arg Leu Ala Val Met Asn Ala Leu Ile Gln Asp Arg
                245                 250                 255

Leu Lys Gln Asn Gly Ser Glu Ser Asp Asp Asp Cys Tyr Leu Asn Phe
            260                 265                 270

Leu Met Ser Glu Ala Lys Thr Leu Thr Lys Glu Gln Ile Ala Ile Leu
```

```
            275                 280                 285
Val Trp Glu Thr Ile Ile Glu Thr Ala Asp Thr Thr Leu Val Thr Thr
290                 295                 300

Glu Trp Ala Ile Tyr Glu Leu Ala Lys His Pro Ser Val Gln Asp Arg
305                 310                 315                 320

Leu Cys Lys Glu Ile Gln Asn Val Cys Gly Gly Glu Lys Phe Lys Glu
                325                 330                 335

Glu Gln Leu Ser Gln Val Pro Tyr Leu Asn Gly Val Phe His Glu Thr
            340                 345                 350

Leu Arg Lys Tyr Ser Pro Ala Pro Leu Val Pro Ile Arg Tyr Ala His
        355                 360                 365

Glu Asp Thr Gln Ile Gly Gly Tyr His Val Pro Ala Gly Ser Glu Ile
370                 375                 380

Ala Ile Asn Ile Tyr Gly Cys Asn Met Asp Lys Lys Arg Trp Glu Arg
385                 390                 395                 400

Pro Glu Asp Trp Trp Pro Glu Arg Phe Leu Asp Asp Gly Lys Tyr Glu
                405                 410                 415

Thr Ser Asp Leu His Lys Thr Met Ala Phe Gly Ala Gly Lys Arg Val
            420                 425                 430

Cys Ala Gly Ala Leu Gln Ala Ser Leu Met Ala Gly Ile Ala Ile Gly
        435                 440                 445

Arg Leu Val Gln Glu Phe Glu Trp Lys Leu Arg Asp Gly Glu Glu Glu
450                 455                 460

Asn Val Asp Thr Tyr Gly Leu Thr Ser Gln Lys Leu Tyr Pro Leu Met
465                 470                 475                 480

Ala Ile Ile Asn Pro Arg Arg Ser
                485

<210> SEQ ID NO 56
<211> LENGTH: 483
<212> TYPE: PRT
<213> ORGANISM: Stevia rebaudiana

<400> SEQUENCE: 56

Trp Tyr Leu Lys Ser Tyr Thr Ser Ala Arg Arg Ser Gln Ser Asn His
1               5                   10                  15

Leu Pro Arg Val Pro Glu Val Pro Gly Val Pro Leu Leu Gly Asn Leu
            20                  25                  30

Leu Gln Leu Lys Glu Lys Lys Pro Tyr Met Thr Phe Thr Arg Trp Ala
        35                  40                  45

Ala Thr Tyr Gly Pro Ile Tyr Ser Ile Lys Thr Gly Ala Thr Ser Met
    50                  55                  60

Val Val Val Ser Ser Asn Glu Ile Ala Lys Glu Ala Leu Val Thr Arg
65                  70                  75                  80

Phe Gln Ser Ile Ser Thr Arg Asn Leu Ser Lys Ala Leu Lys Val Leu
                85                  90                  95

Thr Ala Asp Lys Thr Met Val Ala Met Ser Asp Tyr Asp Asp Tyr His
            100                 105                 110

Lys Thr Val Lys Arg His Ile Leu Thr Ala Val Leu Gly Pro Asn Ala
        115                 120                 125

Gln Lys Lys His Arg Ile His Arg Asp Ile Met Met Asp Asn Ile Ser
    130                 135                 140

Thr Gln Leu His Glu Phe Val Lys Asn Asn Pro Glu Gln Glu Glu Val
145                 150                 155                 160
```

Asp Leu Arg Lys Ile Phe Gln Ser Glu Leu Phe Gly Leu Ala Met Arg
            165                 170                 175

Gln Ala Leu Gly Lys Asp Val Glu Ser Leu Tyr Val Glu Asp Leu Lys
        180                 185                 190

Ile Thr Met Asn Arg Asp Glu Ile Phe Gln Val Leu Val Asp Pro
    195                 200                 205

Met Met Gly Ala Ile Asp Val Asp Trp Arg Asp Phe Phe Pro Tyr Leu
    210                 215                 220

Lys Trp Val Pro Asn Lys Phe Glu Asn Thr Ile Gln Gln Met Tyr
225                 230                 235                 240

Ile Arg Arg Glu Ala Val Met Lys Ser Leu Ile Lys Glu His Lys Lys
                245                 250                 255

Arg Ile Ala Ser Gly Glu Lys Leu Asn Ser Tyr Ile Asp Tyr Leu Leu
            260                 265                 270

Ser Glu Ala Gln Thr Leu Thr Asp Gln Gln Leu Leu Met Ser Leu Trp
        275                 280                 285

Glu Pro Ile Ile Glu Ser Ser Asp Thr Thr Met Val Thr Thr Glu Trp
    290                 295                 300

Ala Met Tyr Glu Leu Ala Lys Asn Pro Lys Leu Gln Asp Arg Leu Tyr
305                 310                 315                 320

Arg Asp Ile Lys Ser Val Cys Gly Ser Glu Lys Ile Thr Glu Glu His
                325                 330                 335

Leu Ser Gln Leu Pro Tyr Ile Thr Ala Ile Phe His Glu Thr Leu Arg
            340                 345                 350

Arg His Ser Pro Val Pro Ile Ile Pro Leu Arg His Val His Glu Asp
        355                 360                 365

Thr Val Leu Gly Gly Tyr His Val Pro Ala Gly Thr Glu Leu Ala Val
    370                 375                 380

Asn Ile Tyr Gly Cys Asn Met Asp Lys Asn Val Trp Glu Asn Pro Glu
385                 390                 395                 400

Glu Trp Asn Pro Glu Arg Phe Met Lys Glu Asn Glu Thr Ile Asp Phe
                405                 410                 415

Gln Lys Thr Met Ala Phe Gly Gly Gly Lys Arg Val Cys Ala Gly Ser
            420                 425                 430

Leu Gln Ala Leu Leu Thr Ala Ser Ile Gly Ile Gly Arg Met Val Gln
        435                 440                 445

Glu Phe Glu Trp Lys Leu Lys Asp Met Thr Gln Glu Val Asn Thr
    450                 455                 460

Ile Gly Leu Thr Thr Gln Met Leu Arg Pro Leu Arg Ala Ile Ile Lys
465                 470                 475                 480

Pro Arg Ile

<210> SEQ ID NO 57
<211> LENGTH: 494
<212> TYPE: PRT
<213> ORGANISM: Physcomitrella patens

<400> SEQUENCE: 57

Phe Val Ala Arg Thr Cys Leu Arg Asn Lys Lys Arg Leu Pro Pro Ala
1               5                   10                  15

Ile Pro Gly Gly Leu Pro Val Leu Gly Asn Leu Leu Gln Leu Thr Glu
            20                  25                  30

Lys Lys Pro His Arg Thr Phe Thr Ala Trp Ser Lys Glu His Gly Pro
        35                  40                  45

```
Ile Phe Thr Ile Lys Val Gly Ser Val Pro Gln Ala Val Asn Asn
     50                  55                  60
Ser Glu Ile Ala Lys Glu Val Leu Val Thr Lys Phe Ala Ser Ile Ser
 65                  70                  75                  80
Lys Arg Gln Met Pro Met Ala Leu Arg Val Leu Thr Arg Asp Lys Thr
                 85                  90                  95
Met Val Ala Met Ser Asp Tyr Gly Glu His Arg Met Leu Lys Lys
                100                 105                 110
Leu Val Met Thr Asn Leu Leu Gly Pro Thr Thr Gln Asn Lys Asn Arg
                115                 120                 125
Ser Leu Arg Asp Asp Ala Leu Ile Gly Met Ile Glu Gly Val Leu Ala
130                 135                 140
Glu Leu Lys Ala Ser Pro Thr Ser Pro Lys Val Val Asn Val Arg Asp
145                 150                 155                 160
Tyr Val Gln Arg Ser Leu Phe Pro Phe Ala Leu Gln Gln Val Phe Gly
                165                 170                 175
Tyr Ile Pro Asp Gln Val Glu Val Leu Glu Leu Gly Thr Cys Val Ser
                180                 185                 190
Thr Trp Asp Met Phe Asp Ala Leu Val Val Ala Pro Leu Ser Ala Val
        195                 200                 205
Ile Asn Val Asp Trp Arg Asp Phe Phe Pro Ala Leu Arg Trp Ile Pro
210                 215                 220
Asn Arg Ser Val Glu Asp Leu Val Arg Thr Val Asp Phe Lys Arg Asn
225                 230                 235                 240
Ser Ile Met Lys Ala Leu Ile Arg Ala Gln Arg Met Arg Leu Ala Asn
                245                 250                 255
Leu Lys Glu Pro Pro Arg Cys Tyr Ala Asp Ile Ala Leu Thr Glu Ala
                260                 265                 270
Thr His Leu Thr Glu Lys Gln Leu Glu Met Ser Leu Trp Glu Pro Ile
        275                 280                 285
Ile Glu Ser Ala Asp Thr Thr Leu Val Thr Ser Glu Trp Ala Met Tyr
290                 295                 300
Glu Ile Ala Lys Asn Pro Asp Cys Gln Asp Arg Leu Tyr Arg Glu Ile
305                 310                 315                 320
Val Ser Val Ala Gly Thr Glu Arg Met Val Thr Glu Asp Asp Leu Pro
                325                 330                 335
Asn Met Pro Tyr Leu Gly Ala Ile Ile Lys Glu Thr Leu Arg Lys Tyr
                340                 345                 350
Thr Pro Val Pro Leu Ile Pro Ser Arg Phe Val Glu Glu Asp Ile Thr
        355                 360                 365
Leu Gly Gly Tyr Asp Ile Pro Lys Gly Tyr Gln Ile Leu Val Asn Leu
370                 375                 380
Phe Ala Ile Ala Asn Asp Pro Ala Val Trp Ser Asn Pro Glu Lys Trp
385                 390                 395                 400
Asp Pro Glu Arg Met Leu Ala Asn Lys Val Asp Met Gly Phe Arg
                405                 410                 415
Asp Phe Ser Leu Met Pro Phe Gly Ala Gly Lys Arg Met Cys Ala Gly
                420                 425                 430
Ile Thr Gln Ala Met Phe Ile Ile Pro Met Asn Val Ala Ala Leu Val
                435                 440                 445
Gln His Cys Glu Trp Arg Leu Ser Pro Gln Glu Ile Ser Asn Ile Asn
450                 455                 460
Asn Lys Ile Glu Asp Val Val Tyr Leu Thr Thr His Lys Leu Ser Pro
```

```
                465                 470                 475                 480
Leu Ser Cys Glu Ala Thr Pro Arg Ile Ser His Arg Leu Pro
                    485                 490

<210> SEQ ID NO 58
<211> LENGTH: 381
<212> TYPE: PRT
<213> ORGANISM: Pleurotus sapidus

<400> SEQUENCE: 58

Met Gly Lys Leu His Pro Leu Ala Ile Ile Pro Asp Tyr Lys Gly Ser
1               5                   10                  15

Met Ala Ala Ser Val Thr Ile Phe Asn Lys Arg Thr Asn Pro Leu Asp
                20                  25                  30

Ile Ser Val Asn Gln Ala Asn Asp Trp Pro Trp Arg Tyr Ala Lys Thr
            35                  40                  45

Cys Val Leu Ser Ser Asp Trp Ala Leu His Glu Met Ile Ile His Leu
        50                  55                  60

Asn Asn Thr His Leu Val Glu Glu Ala Val Ile Val Ala Ala Gln Arg
65                  70                  75                  80

Lys Leu Ser Pro Ser His Ile Val Phe Arg Leu Leu Glu Pro His Trp
                85                  90                  95

Val Val Thr Leu Ser Leu Asn Ala Leu Ala Arg Ser Val Leu Ile Pro
            100                 105                 110

Glu Val Ile Val Pro Ile Ala Gly Phe Ser Ala Pro His Ile Phe Gln
        115                 120                 125

Phe Ile Arg Glu Ser Phe Thr Asn Phe Asp Trp Lys Ser Leu Tyr Val
130                 135                 140

Pro Ala Asp Leu Glu Ser Arg Gly Phe Pro Val Asp Gln Leu Asn Ser
145                 150                 155                 160

Pro Lys Phe His Asn Tyr Ala Tyr Ala Arg Asp Ile Asn Asp Met Trp
                165                 170                 175

Thr Thr Leu Lys Lys Phe Val Ser Ser Val Leu Gln Asp Ala Gln Tyr
            180                 185                 190

Tyr Pro Asp Asp Ala Ser Val Ala Gly Asp Thr Gln Ile Gln Ala Trp
        195                 200                 205

Cys Asp Glu Met Arg Ser Gly Met Gly Ala Gly Met Thr Asn Phe Pro
210                 215                 220

Glu Ser Ile Thr Thr Val Asp Asp Leu Val Asn Met Val Thr Met Cys
225                 230                 235                 240

Ile His Ile Ala Ala Pro Gln His Thr Ala Val Asn Tyr Leu Gln Gln
                245                 250                 255

Tyr Tyr Gln Thr Phe Val Ser Asn Lys Pro Ser Ala Leu Phe Ser Pro
            260                 265                 270

Leu Pro Thr Ser Ile Ala Gln Leu Gln Lys Tyr Thr Glu Ser Asp Leu
        275                 280                 285

Met Ala Ala Leu Pro Leu Asn Ala Lys Arg Gln Trp Leu Leu Met Ala
290                 295                 300

Gln Ile Pro Tyr Leu Leu Ser Met Gln Val Gln Glu Asp Glu Asn Ile
305                 310                 315                 320

Val Thr Tyr Ala Ala Asn Ala Ser Thr Asp Lys Asp Pro Ile Ile Ala
                325                 330                 335

Ser Ala Gly Arg Gln Leu Ala Ala Asp Leu Lys Lys Leu Ala Ala Val
            340                 345                 350
```

```
Phe Leu Val Asn Ser Ala Gln Leu Asp Asp Gln Asn Thr Pro Tyr Asp
            355                 360                 365

Val Leu Ala Pro Glu Gln Leu Ala Asn Ala Ile Val Ile
    370                 375                 380

<210> SEQ ID NO 59
<211> LENGTH: 475
<212> TYPE: PRT
<213> ORGANISM: Cichorium intybus

<400> SEQUENCE: 59

Leu Leu Thr Arg Thr Thr Ser Lys Lys Asn Leu Leu Pro Glu Pro Trp
1               5                   10                  15

Arg Leu Pro Ile Ile Gly His Met His His Leu Ile Gly Thr Met Pro
            20                  25                  30

His Arg Gly Val Met Glu Leu Ala Arg Lys His Gly Ser Leu Met His
        35                  40                  45

Leu Gln Leu Gly Glu Val Ser Thr Ile Val Val Ser Ser Pro Arg Trp
    50                  55                  60

Ala Lys Glu Val Leu Thr Thr Tyr Asp Ile Thr Phe Ala Asn Arg Pro
65                  70                  75                  80

Glu Thr Leu Thr Gly Glu Ile Val Ala Tyr His Asn Thr Asp Ile Val
                85                  90                  95

Leu Ala Pro Tyr Gly Glu Tyr Trp Arg Gln Leu Arg Lys Leu Cys Thr
            100                 105                 110

Leu Glu Leu Leu Ser Asn Lys Lys Val Lys Ser Phe Gln Ser Leu Arg
        115                 120                 125

Glu Glu Glu Cys Trp Asn Leu Val Lys Asp Ile Arg Ser Thr Gly Gln
    130                 135                 140

Gly Ser Pro Ile Asn Leu Ser Glu Asn Ile Phe Lys Met Ile Ala Thr
145                 150                 155                 160

Ile Leu Ser Arg Ala Ala Phe Gly Lys Gly Ile Lys Asp Gln Met Lys
                165                 170                 175

Phe Thr Glu Leu Val Lys Glu Ile Leu Arg Leu Thr Gly Gly Phe Asp
            180                 185                 190

Val Ala Asp Ile Phe Pro Ser Lys Lys Leu Leu His His Leu Ser Gly
        195                 200                 205

Lys Arg Ala Lys Leu Thr Asn Ile His Asn Lys Leu Asp Asn Leu Ile
    210                 215                 220

Asn Asn Ile Ile Ala Glu His Pro Gly Asn Arg Thr Ser Ser Ser Gln
225                 230                 235                 240

Glu Thr Leu Leu Asp Val Leu Arg Leu Lys Glu Ser Ala Glu Phe
                245                 250                 255

Pro Leu Thr Ala Asp Asn Val Lys Ala Val Ile Leu Asp Met Phe Gly
            260                 265                 270

Ala Gly Thr Asp Thr Ser Ser Ala Thr Ile Glu Trp Ala Ile Ser Glu
        275                 280                 285

Leu Ile Arg Cys Pro Arg Ala Met Glu Lys Val Gln Thr Glu Leu Arg
    290                 295                 300

Gln Ala Leu Asn Gly Lys Glu Arg Ile Gln Glu Asp Leu Gln Glu
305                 310                 315                 320

Leu Asn Tyr Leu Lys Leu Val Ile Lys Glu Thr Leu Arg Leu His Pro
                325                 330                 335

Pro Leu Pro Leu Val Met Pro Arg Glu Cys Arg Glu Pro Cys Val Leu
            340                 345                 350
```

```
Gly Gly Tyr Asp Ile Pro Ser Lys Thr Lys Leu Ile Val Asn Val Phe
            355                 360                 365

Ala Ile Asn Arg Asp Pro Glu Tyr Trp Lys Asp Ala Glu Thr Phe Met
        370                 375                 380

Pro Glu Arg Phe Glu Asn Ser Pro Ile Thr Val Met Gly Ser Glu Tyr
385                 390                 395                 400

Glu Tyr Leu Pro Phe Gly Ala Gly Arg Arg Met Cys Pro Gly Ala Ala
                405                 410                 415

Leu Gly Leu Ala Asn Val Glu Leu Pro Leu Ala His Ile Leu Tyr Phe
            420                 425                 430

Asn Trp Lys Leu Pro Asn Gly Lys Thr Phe Glu Asp Leu Asp Met Thr
        435                 440                 445

Glu Ser Phe Gly Ala Thr Val Gln Arg Lys Thr Glu Leu Leu Leu Val
        450                 455                 460

Pro Thr Asp Phe Gln Thr Leu Thr Ala Ser Thr
465                 470                 475

<210> SEQ ID NO 60
<211> LENGTH: 468
<212> TYPE: PRT
<213> ORGANISM: Helianthus annuus

<400> SEQUENCE: 60

Leu Leu Thr Arg Pro Thr Ser Ser Lys Asn Arg Leu Pro Glu Pro Trp
1               5                   10                  15

Arg Leu Pro Ile Ile Gly His Met His His Leu Ile Gly Thr Met Pro
            20                  25                  30

His Arg Gly Val Met Asp Leu Ala Arg Lys Tyr Gly Ser Leu Met His
        35                  40                  45

Leu Gln Leu Gly Glu Val Ser Ala Ile Val Val Ser Ser Pro Lys Trp
    50                  55                  60

Ala Lys Glu Ile Leu Thr Thr Tyr Asp Ile Pro Phe Ala Asn Arg Pro
65                  70                  75                  80

Glu Thr Leu Thr Gly Glu Ile Ile Ala Tyr His Asn Thr Asp Ile Val
                85                  90                  95

Leu Ala Pro Tyr Gly Glu Tyr Trp Arg Gln Leu Arg Lys Leu Cys Thr
            100                 105                 110

Leu Glu Leu Leu Ser Val Lys Lys Val Lys Ser Phe Gln Ser Leu Arg
        115                 120                 125

Glu Glu Glu Cys Trp Asn Leu Val Gln Glu Ile Lys Ala Ser Gly Ser
    130                 135                 140

Gly Thr Pro Phe Asn Leu Ser Glu Gly Ile Phe Lys Val Ile Ala Thr
145                 150                 155                 160

Val Leu Ser Arg Ala Ala Phe Gly Lys Gly Ile Lys Asp Gln Lys Gln
                165                 170                 175

Phe Thr Glu Ile Val Lys Glu Ile Leu Arg Glu Thr Gly Gly Phe Asp
            180                 185                 190

Val Ala Asp Ile Phe Pro Ser Lys Lys Phe Leu His His Leu Ser Gly
        195                 200                 205

Lys Arg Gly Arg Leu Thr Ser Ile His Asn Lys Leu Asp Ser Leu Ile
    210                 215                 220

Asn Asn Leu Val Ala Glu His Thr Val Ser Lys Ser Ser Lys Val Asn
225                 230                 235                 240

Glu Thr Leu Leu Asp Val Leu Leu Arg Leu Lys Asn Ser Glu Glu Phe
```

245                 250                 255

Pro Leu Thr Ala Asp Asn Val Lys Ala Ile Ile Leu Asp Met Phe Gly
                    260                 265                 270

Ala Gly Thr Asp Thr Ser Ser Ala Thr Val Glu Trp Ala Ile Ser Glu
                    275                 280             285

Leu Ile Arg Cys Pro Arg Ala Met Glu Lys Val Gln Ala Glu Leu Arg
            290                 295                 300

Gln Ala Leu Asn Gly Lys Glu Arg Ile Lys Glu Glu Ile Gln Asp
        305                 310                 315                 320

Leu Pro Tyr Leu Asn Leu Val Ile Arg Glu Thr Leu Arg Leu His Pro
                        325                 330                 335

Pro Leu Pro Leu Val Met Pro Arg Glu Cys Arg Gln Ala Met Asn Leu
                    340                 345                 350

Ala Gly Tyr Asp Val Ala Asn Lys Thr Lys Leu Ile Val Asn Val Phe
                    355                 360                 365

Ala Ile Asn Arg Asp Pro Glu Tyr Trp Lys Asp Ala Glu Ser Phe Asn
            370                 375                 380

Pro Glu Arg Phe Glu Asn Ser Asn Thr Thr Ile Met Gly Ala Asp Tyr
        385                 390                 395                 400

Glu Tyr Leu Pro Phe Gly Ala Gly Arg Arg Met Cys Pro Gly Ser Ala
                        405                 410                 415

Leu Gly Leu Ala Asn Val Gln Leu Pro Leu Ala Asn Ile Leu Tyr Tyr
                    420                 425                 430

Phe Lys Trp Lys Leu Pro Asn Gly Ala Ser His Asp Gln Leu Asp Met
                    435                 440                 445

Thr Glu Ser Phe Gly Ala Thr Val Gln Arg Lys Thr Glu Leu Met Leu
            450                 455                 460

Val Pro Ser Phe
        465

<210> SEQ ID NO 61
<211> LENGTH: 12
<212> TYPE: PRT
<213> ORGANISM: Artificial Sequence
<220> FEATURE:
<223> OTHER INFORMATION: Synthetic sequence

<400> SEQUENCE: 61

His Val Tyr Gly Arg Ala Val Val Glu Gln Trp Arg
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence

<400> SEQUENCE: 62

Val Tyr Gly Arg Ala Val Val Glu Gln Trp Arg
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 63

```
Phe Trp Tyr Leu Lys Ser Tyr Thr Ser Ala Arg Arg
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 64

Trp Tyr Leu Lys Ser Tyr Thr Ser Ala Arg Arg
1               5                   10
```

INCREASING PRODUCTIVITY OF *E. COLI* HOST CELLS THAT FUNCTIONALLY EXPRESS P450 ENZYMES

FIELD OF THE INVENTION

The present invention relates to production of chemical species through oxidative chemistry in bacterial host cells. Particularly, the present invention provides P450 enzymes engineered for functional expression in bacterial host cells such as *E. coli*.

BACKGROUND OF THE INVENTION

*E. coli* is widely used for production of chemicals by the recombinant expression of biosynthetic pathways, which can involve overexpression of several native and/or foreign genes. However, where the biosynthetic pathway involves recombinant expression of one or more cytochrome P450 enzymes (e.g., to perform oxidative chemistry), other host organisms such as yeast are generally preferred. See Chang & Keasling, *Nat. Chem. Bio.* 2006. The perceived limitations of the bacterial system for oxidative chemistry include the absence of electron transfer machinery and P450-reductases (CPRs), and translational incompatibility of the membrane signal modules of P450 enzymes due to the lack of an endoplasmic reticulum. Thus, it remains a commonly held belief in the scientific community that *E. coli* is a generally unsuitable host for P450 expression and expression of biosynthetic pathways incorporating the same. See Tippman et al., *Biotech. Journal* (2013); Thodey et al., *Nat. Chem. Bio.* (2014).

It is an object of the invention to improve productivity of P450 enzymes in bacterial platforms such as *E. coli*, to thereby expand the utility of these platforms for P450 chemistry.

SUMMARY OF THE INVENTION

In various aspects, the invention provides P450 enzymes engineered for functional expression in bacterial cells (e.g., *E. coli*), and polynucleotides encoding the same. The invention further provides bacterial host cells expressing the engineered P450 enzymes, and methods for producing chemical species through recombinant expression of biosynthetic pathways involving P450 enzymes.

The engineered P450 enzymes described herein have a deletion of all or part of the wild type P450 N-terminal transmembrane region, and the addition of a transmembrane domain derived from an *E. coli* inner membrane, cytoplasmic C-terminus protein. It is believed that the transmembrane domain acts to anchor the P450 in the *E. coli* inner membrane. In various embodiments, the transmembrane domain is a single-pass transmembrane domain.

In various embodiments, the transmembrane domain (or "N-terminal anchor") is derived from an *E. coli* gene selected from waaA, ypfN, yhcB, yhbM, yhhm, zipA, ycgG, djlA, sohB, lpxK, F11O, motA, htpx, pgaC, ygdD, hemr, and ycls. These genes were identified as inner membrane, cytoplasmic C-terminus proteins through bioinformatic prediction as well as experimental validation. The invention may employ an N-terminal anchor sequence that is a derivative of the *E. coli* wild-type transmembrane domain, that is, having one or more mutations with respect to the wild-type sequence.

In some aspects, the invention provides methods for the production of chemical species by expressing in *E. coli* cells one or more biosynthetic pathways including at least one membrane-anchored P450 (CYP) enzyme, and culturing the *E. coli* cells to produce the chemical species. At least one membrane-anchored P450 enzyme contains a transmembrane domain derived from an *E. coli* inner membrane, cytoplasmic C-terminus protein. As demonstrated herein, previous methods for expressing P450 proteins in *E. coli* can result in a substantial stress response, which limits productivity of the host cell. *E. coli* cells expressing the engineered P450 enzymes described herein do not exhibit a substantially stressed phenotype in some embodiments, thereby improving pathway productivity.

The invention in various aspects is applicable to various P450 enzymes, including plant-derived P450 enzymes, which can be further engineered for productivity in a bacterial host cell system. These engineered P450 enzymes can be used in the production of a variety of chemical species through recombinant pathway expression, including but not limited to production of terpenoid compounds. Terpenoids represent a diverse class of molecules that provide beneficial health and nutritional attributes, as well as numerous other commercial applications. For example, terpenoids find use in the food and beverage industries as well as the perfume, cosmetic and health care industries.

In various embodiments, the *E. coli* cell is used for the production of chemicals by the recombinant expression of biosynthetic pathways, which can involve overexpression of several native and/or foreign genes. Often, expression of several foreign genes in *E. coli* and/or overexpression of native *E. coli* genes can induce a substantial stress response, which limits productivity. Conventional expression of P450 enzymes in *E. coli*, together with cytochrome P450 reductase (CPR) partners to regenerate the cofactor, can substantially add to this stress response, as exhibited for example by overexpression of IbpA, a protein that is overexpressed in *E. coli* under conditions of high protein aggregation and stress. It is critical that the P450 enzyme expression induce as little cell stress as possible to avoid limits on pathway productivity. Accordingly, the invention helps minimize cellular stress in a host *E. coli* cell to increase productivity of the host cell for production of chemical species.

Other aspects and embodiments of the invention will be apparent from the following detailed disclosure.

DETAILED DESCRIPTION OF THE INVENTION

Figure 1:
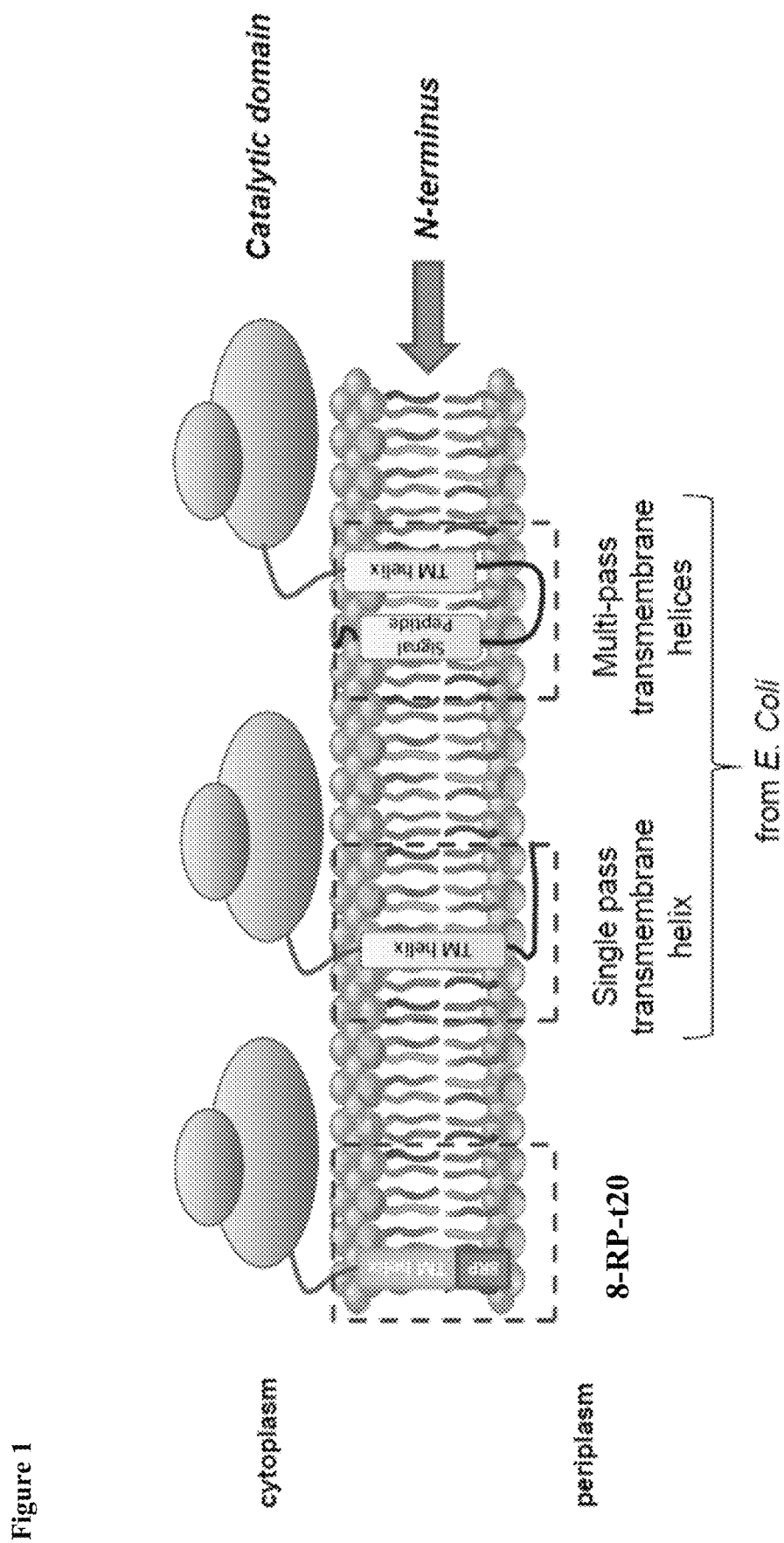
FIG. 1 illustrates N-terminal anchors for expressing P450 proteins in *E. coli*, including the previous designs based on truncation of the P450 transmembrane helix with the addition of an 8-amino acid peptide (8RP), and the use of single-pass and multi-pass transmembrane helices from *E. coli* proteins as described herein.

The invention provides for improved functional expression of P450 enzymes in bacterial host cells, and in particular, bacterial cells that do not naturally possess P450 enzymes, such as *E. coli*. While these bacterial platforms are widely used for production of a wide variety of chemicals, they are generally considered insufficient when P450 chemistry is required. The perceived limitations of bacterial systems such as *E. coli* for oxidative chemistry include the absence of electron transfer machinery and P450-reductases (CPRs), and translational incompatibility of the membrane signal modules of P450 enzymes due to the lack of an endoplasmic reticulum.

Basic P450 expression in *E. coli* has been obtained by co-expression of the P450 with a CPR. The P450 enzyme contained a truncation of at least part of the native P450 transmembrane region, which was replaced with the 8 amino acid tag MALLLAVF (SEQ ID NO: 61; which is derived from bovine P45017α) at the N-terminus. The present invention demonstrates that this tag is far from optimal, and results in a substantial cell stress response.

The invention provides P450 enzymes engineered for functional expression in bacterial platforms such as *E. coli*. The P450 enzymes comprise an N-terminal membrane anchor sequence derived from a native *E. coli* inner membrane protein having a cytoplasmic C-terminus. The N-terminal membrane anchor sequence replaces some or the entire native P450 N-terminal transmembrane region, where present in the wild-type enzyme. Expression of the engineered P450 enzymes in bacteria induces less cell stress than previous attempts to functionally express P450 enzymes in *E. coli*, for example. The invention allows for increases in biosynthetic productivity in bacterial host platforms, due in-part, to substantial improvements in P450 efficiency and to minimizing the cell stress response.

In one aspect, the present invention relates to a P450 enzyme having a transmembrane domain derived from an *E. coli* inner membrane protein having a cytoplasmic C-terminus. The *E. coli* transmembrane domain (or derivative thereof) replaces part or the entire native P450 N-terminal transmembrane region. In some embodiments, the transmembrane domain is a single-pass transmembrane domain, or in other embodiments, is a multi-pass (e.g., 2, 3, or more transmembrane helices) transmembrane domain.

The P450 enzyme may be derived from any source, including plants, animals, or microbes. The P450 enzyme may be a CYP70, CYP71, CYP73, CYP76 (e.g., CYP76F), CYP82 or CYP92 family P450. The P450 may be an enzyme disclosed in U.S. Pat. No. 8,722,363, which is hereby incorporated by reference. In some embodiments, the P450 is a plant P450 enzyme. Plant cytochrome P450s are involved in a wide range of biosynthetic reactions, leading to various fatty acid conjugates, plant hormones, defensive compounds, or medically and commercially important compounds, including terpenoids. Terpenoids represent the largest class of characterized natural plant compounds and are often substrates for plant P450 enzymes. In some embodiments, the P450 is derived from a species selected from *Zingiber* sp., *Barnadesia* sp., *Hyoscyamus* sp., *Latuca* sp., *Nicotiana* sp., *Citrus* sp., *Artemesia* sp., *Arabidopsis* sp, *Stevia* sp., *Bacillus* sp., *Pleurotus* sp., *Cichorium* sp., *Helianthus* sp., and *Physcomitrella* sp., *Taxus* sp., *Rosa* sp., *Cymbopogon* sp., *Humulus* sp., *Pogostemon* sp., and *Cannabis* sp. Wild-type P450 enzyme sequences are known and publically available, and/or can be obtained by genetic analysis of select plants based on well-known P450 motifs. See, for example, Saxena A. et al., *Identification of cytochrome P450 heme motif in plants proteome, Plant Omics* (2013); Chapple C., *Molecular-genetic analysis of*

*plant cytochrome p450-dependent monooxygenases*, Annual Review of Plant Physiology and Plant Molecular Biology Vol. 49:311-343 (1998).

Table 1 provides a list of exemplary P450 enzymes that may be engineered in accordance with the invention:

TABLE 1

| Species | Name | Native Substrate | Native Reaction Product |
|---|---|---|---|
| *Zingiber zerumbet* | zzHO | α-humulene | 8-hydroxy-α-humulene |
| *Barnadesia spinosa* | BsGAO | germacrene A | germacra-1(10),4,11(13)-trien-12-ol |
| *Hyoscyamus muticus* | HmPO | premnaspirodiene | solavetivol |
| *Latuca spicata* | LsGAO | germacrene A | germacra-1(10),4,11(13)-trien-12-ol |
| *Nicotiana tabacum* | NtEAO | 5-epi-aristolochene | capsidiol |
| *Citrus × paradisi* | CpVO | valencene | nootkatol |
| *Artemesia annua* | AaAO | amorphadiene | artemisinic acid |
| *Arabidopsis thaliana* | AtKO | kaurene | kaurenoic acid |
| *Stevia rebaudiana* | SrKO | kaurene | kaurenoic acid |
| *Physcomitrella patens* | PpKO | kaurene | kaurenoic acid |
| *Bacillus megaterium* | BmVO | fatty acids | hydroxylated FAs |
| *Pleurotus sapidus* | PsVO | valencene | nootkatone |
| *Pleurotus ostreatus* | PoLO | unknown | unknown |
| *Cichorium intybus* | CiVO | valencene | nootkatone |
| *Helianthus annuus* | HaGAO | germacrene A | germacrene A acid |

Thus, the engineered P450 enzyme may be based on wild-type sequences of ZzHO (SEQ ID NO: 1), BsGAO (SEQ ID NO: 2), HmPO (SEQ ID NO: 3), LsGAO (SEQ ID NO: 4), NtEAO (SEQ ID NO: 5), CpVO (SEQ ID NO: 6), AaAO (SEQ ID NO: 7), AtKO (SEQ ID NO: 8), SrKO (SEQ ID NO: 9), PpKO (SEQ ID NO:10), BmVO (SEQ ID NO: 11), PsVO (SEQ ID NO:12), PoLO (SEQ ID NO: 13), CiVO (SEQ ID NO: 14), or HaGAO (SEQ ID NO: 15).

Additional P450 enzymes that can be engineered in accordance with the invention include limonene-6-hydroxylase (AAQ18706.1, AAD44150.1), (−)-limonene-3-hydroxylase (EF426464, AY622319), kaurenoic acid 13-hydroxylase (EU722415.1), carotenoid cleavage dioxygenase (ABY60886.1, BAJ05401.1), beta-carotene hydroxylase (AAA64983.1), amorpha-4,11-diene monoxygenase (DQ315671), taxadiene 5-alpha hydroxylase (AY289209.2), 5-alpha-taxadienol-10-beta-hydroxylase (AF318211.1), taxoid 10-beta hydroxylase (AY563635.1), taxane 13-alpha-hydroxylase (AY056019.1), taxane 14b-hydroxylase (AY188177.1), taxoid 7-beta-hydroxylase (AY307951.1). The amino acid and encoding nucleotide sequences of these enzymes are hereby incorporated by reference. Derivatives of these P450s may be constructed in accordance with this disclosure.

The particular P450 enzyme scaffold can be selected based on the desired substrate specificity, which may be its natural substrate, or a non-natural substrate similar to the natural substrate, or otherwise determined experimentally. P450's can have varying substrate specificities, and thus can be engineered for chemistry on non-natural substrates. See, for example, Wu et al., *Expansion of substrate specificity of cytochrome P450 2A6 by random and site-directed mutagenesis*, J. Biol. Chem. 280(49): 41090-100 (2005). Exemplary substrates for P450 chemistry include various secondary metabolites such as, without limitation, terpenoids, alkaloids, cannabinoids, steroids, saponins, glycosides, stilbenoids, polyphenols, antibiotics, polyketides, fatty acids, and non-ribosomal peptides. Exemplary products that may be produced through P450 chemistry include, without limitation, lutein, tocopherol, abietic acid, mogroside, forskolin, amyrin, lupeol, butyrospermol, quillic acid, triterpenoid saponins, oleanic acid, betulinic acid, boswellic acid, gymnemic acid, banaba/corosolic acid, cissus keto-steroid, curcurbitane triterpenoid, santalol, marrubiin, montbretin A, tropolone, sclareol, pseudolaric acid, grindelic acid, kauralexin, viteagnusin, diterpenoid epoxide triptolide, quinone triterpene celastrol, gibberellic acid, pseudolaric acid, carveol, carvone, nootkatol, nootkatone, piperitone, steviol, perillaldehyde, tagetone, verbenone, menthol, thymol, 3-oxo-alpha-Ionone, zeanthin, artemisinin, taxol, gingkolide, gossypol, pseudoterosin, crotophorbolone, englerin, psiguadial, stemodinone, maritimol, cyclopamine, veratramine, aplyviolene, macfarlandin E, betulinic acid, oleanolic acid, ursoloic acid, dolichol, lupeol, euphol, cassaic acid, erthroxydiol, trisporic acid, podocarpic acid, retene, dehydroleucodine, phorbol, cafestol, kahweol, tetrahydrocannabinol, androstenol, tanshinone IIA or JIB or VI, cryptotanshinone, 15,16-dihydrotanshinone, trijuganone A or B, dihydrotanshinone I, miltirone, ferruginol, hydrotanshinone IIA, and 1,2-dihydrocrytotanshinone.

Exemplary terpenoid products that may be produced in accordance with the invention are described in U.S. Pat. No. 8,927,241, which is hereby incorporated by reference, and include: alpha-sinensal, beta-Thujone, Camphor, Carveol, Carvone, Cineole, Citral, Citronellal, Cubebol, Geraniol, Limonene, Menthol, Menthone, Nootkatone, Nootkatol, Patchouli, Piperitone, Sabinene, Steviol, Steviol glycoside, Taxadiene, and Thymol.

In various embodiments, the engineered P450 enzyme comprises an amino acid sequence that has at least about 30% sequence identity, at least about 40% sequence identity, or at least about 50% sequence identity to any one of SEQ ID NOS: 1-15, or other P450 enzyme described herein. While the P450 need not display high sequence identity to these exemplary P450 enzymes in some embodiments, the P450 exhibits well-known P450 motifs and/or secondary structure. Generally, P450 sequence identity is determined by alignment of the full amino acid sequences, except for the N-terminal transmembrane regions (e.g., the alignment does not include about the first 30 amino acids of the wild-type sequence). In some embodiments, the engineered P450 enzyme comprises an amino acid sequence that has at least about 60% identity, at least about 70% identity, at least about 75% identity, at least about 80% identity, at least about 85% identity, at least about 90% identity, at least about 95% identity, at least about 96% identity, at least about 97% identity, or at least about 98% identity to any one of SEQ ID NOS: 48 to 60. SEQ ID NOS: 48 to 60 show P450 enzymes without the predicted transmembrane region (txx is the length of the N-terminal truncation): t22ZzHO (SEQ ID NO:48), t20BsGAO (SEQ ID NO:49), t16HmPO (SEQ ID NO:50), t19LsGAO (SEQ ID NO:51), t16NtEAO (SEQ ID NO:52), t26CpVO (SEQ ID NO:53), t23AaAO (SEQ ID NO:54), t21AtKO (SEQ ID NO:55), t30SrKO (SEQ ID NO:56), t52PpKO (SEQ ID NO:57), t15PsVO (SEQ ID NO:58), t20CiVO (SEQ ID NO:59), t20HaGAO (SEQ ID NO:60).

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, hmmer.wustl.edu/) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J. Mol. Biol.* 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used. Sequence matching analysis may be supplemented by established homology mapping techniques like Shuffle-LAGAN (Brudno M., *Bioinformatics* 2003b, 19 Suppl 1:154-162) or Markov random fields.

In various embodiments, the engineered P450 enzyme may comprise an amino acid sequence having one or more amino acid mutations relative to the wild-type sequence, not including the modifications to the N-terminal transmembrane region (e.g., about the first 18 to 30 amino acids). For example, the P450 enzyme may comprise an amino acid sequence having from 1 to about 50, or from 1 to about 40, or from 1 to about 30, or from 1 to about 25, or from 1 to about 20, or from 1 to about 15, or from 1 to about 10, or from 1 to about 5 mutations relative to the wild-type sequence (e.g., any one of SEQ ID NOS: 48 to 60). In some embodiments, the one or more amino acid mutations may be independently selected from substitutions, insertions, deletions, and truncations. In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe.

As used herein, "non-conservative substitutions" are defined as exchanges of an amino acid by another amino acid listed in a different group of the six standard amino acid groups (1) to (6) shown above.

In various embodiments, the engineered P450 enzyme has a deletion or truncation of part or all of it native transmembrane domain. Generally, the deletion or truncation is about the first 15 to 30 amino acids, and the desired length can be determined based on the present disclosure and using predictive tools known in the art (e.g., PHOBIUS, phobius.sbc.su.se/). See Lukas K, et al., *A Combined Transmembrane Topology and Signal Peptide Prediction Method*, Journal of Molecular Biology, 338(5):1027-1036 (2004); Lukas K, et al., *An HMM posterior decoder for sequence feature prediction that includes homology information*, Bioinformatics, 21 (Suppl 1):i251-i257 (2005); Lukas K, et al., *Advantages of combined transmembrane topology and signal peptide prediction—the Phobius web server*, Nucleic Acids Res., 35:W429-32 (2007).

In various embodiments, the engineered P450 enzyme may have an N-terminal truncation of from about 10 to about 55 amino acids, or from about 15 to about 45 amino acids, or from about 15 to about 40 amino acids, or from about 15 to about 35 amino acids with respect to the wild-type enzyme. In various embodiments, the engineered P450 enzyme may have an N-terminal truncation of about 10, about 11, about 12, about 13, about 14, about 15, about 16, about 17, about 18, about 19, about 20, about 21, about 22, about 23 about 24, about 25, about 26, about 27, about 28, about 29, about 30, about 31, about 32, about 33, about 34, about 35, about 36, about 37, about 38, about 39, or about 40 amino acids with respect to the wild-type enzyme.

The wild-type transmembrane region is replaced with a membrane anchor sequence derived from an *E. coli* protein. The *E. coli* protein is an inner membrane protein with its C-terminus in the cytoplasm. The membrane anchor derived from *E. coli* may be a single-pass transmembrane domain or a multiple-pass transmembrane domain. In some embodiments, the membrane anchor is a single-pass transmembrane domain. Exemplary single-pass transmembrane domains derived from *E. coli* include, but are not limited to, N-terminal domains from the following genes: waaA (SEQ ID NO: 16), ypfN (SEQ ID NO: 17), yhcB (SEQ ID NO: 18), yhbM (SEQ ID NO: 19), yhhm (SEQ ID NO: 20), zipA (SEQ ID NO: 21), ycgG (SEQ ID NO: 22), djlA (SEQ ID NO: 23), sohB (SEQ ID NO: 24), lpxK (SEQ ID NO: 25), F11O (SEQ ID NO: 26), motA (SEQ ID NO: 27), htpx (SEQ ID NO: 28), pgaC (SEQ ID NO: 29), ygdD (SEQ ID NO: 30), hemr (SEQ ID NO: 31), and ycls (SEQ ID NO: 32). In an embodiment, the transmembrane domain is derived from yhcB, yhhm, zipA, sohB, and waaA. The transmembrane regions can likewise be determined by predictive tools known in the art (including PHOBIUS).

In various embodiments, the membrane anchor sequence is from about 8 to about 75 amino acids in length. For example, the membrane anchor may be from about 15 to about 50, or from about 15 to about 40, or from about 15 to about 30, or from about 20 to about 40, or from about 20 to about 30 amino acids in length. In various embodiments, the membrane anchor is about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, or about 75 amino acids in length.

In an embodiment, the transmembrane domain is a yhcB transmembrane domain or a derivative thereof. For example, the transmembrane domain may include the N-terminal 15 to 30 amino acids of yhcB, such as the N-terminal 20 to 22 amino acids of yhcB. For example, the transmembrane domain may include the N-terminal 20, 21, or 22 amino acids of yhcB. The transmembrane domain may have one or more amino acid mutations relative to the wild-type yhcB domain (SEQ ID NO: 18). In some embodiments, the transmembrane domain may have from about 1 to about 8, or from about 1 to about 7, or from about 1 to about 6, or from about 1 to about 5, or from 1 to about 3 mutations relative to the wild-type yhcB sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In an embodiment, the transmembrane domain is a yhhM transmembrane domain or derivative thereof. For example, the transmembrane domain may include the N-terminal 15 to 30, or 19 to 21, amino acids of yhhM. For example, the transmembrane domain may include the N-terminal 19, 20, or 21 amino acids of yhhM. The transmembrane domain may have one or more amino acid mutations relative to the wild type yhhM domain (SEQ ID NO: 20). In some embodiments, the transmembrane domain may have from about 1 to about 8, or from about 1 to about 7, or from about 1 to about 6, or from about 1 to about 5, or from 1 to about 3 mutations relative to the wild-type yhhM sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In an embodiment, the transmembrane domain is a zipA transmembrane domain or derivative thereof. In such an embodiment, the transmembrane domain may include the N-terminal 15 to 30, or 24 to 26, amino acids of zipA. For example, the transmembrane domain may include the N-terminal 24, 25, or 26 amino acids of zipA. The transmembrane domain may have one or more amino acid mutations relative to the wild type zipA domain (SEQ ID NO: 21). In some embodiments, the transmembrane domain may have from about 1 to about 8, or from about 1 to about 7, or from about 1 to about 6, or from about 1 to about 5, or from 1 to about 3 mutations relative to the wild-type zipA sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In an embodiment, the transmembrane domain is a ypfN transmembrane domain or derivative thereof. In such an embodiment, the transmembrane domain may include the N-terminal 15 to 30, or 21 to 23, amino acids of ypfN. For example, the transmembrane domain may include the N-terminal 21, 22, or 23 amino acids of ypfN. The transmembrane domain may have one or more amino acid mutations relative to the wild-type ypfN domain (SEQ ID NO: 17). In some embodiments, the transmembrane domain may have from about 1 to about 8, or from about 1 to about 7, or from about 1 to about 6, or from about 1 to about 5, or from 1 to about 3 mutations relative to the wild-type ypfN sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In an embodiment, the transmembrane domain is a sohB transmembrane domain or derivative. In such an embodiment, the transmembrane domain may include the N-terminal 20 to 35, or 27 to 29, amino acids, of sohB. For example, the transmembrane domain may include the N-terminal 27, 28, or 29 amino acids of sohB. The transmembrane domain may have one or more amino acid mutations relative to the wild-type sohB domain (SEQ ID NO: 24). In some embodiments, the transmembrane domain may have from about 1 to about 8, or from about 1 to about 7, or from about 1 to about 6, or from about 1 to about 5, or from 1 to about 3 mutations relative to the wild-type sohB sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In an embodiment, the transmembrane domain is a waaA transmembrane domain or derivative thereof. In such an embodiment, the transmembrane domain may include the N-terminal 15 to 30, or 20 to 22, amino acids of waaA. For example, the transmembrane domain may include the N-terminal 20, 21, or 22 amino acids of waaA. The transmembrane domain may have one or more amino acid mutations relative to the wild-type waaA domain (SEQ ID NO: 16). In some embodiments, the transmembrane domain may have from about 1 to about 8, or from about 1 to about 7, or from about 1 to about 6, or from about 1 to about 5, or from 1 to about 3 mutations relative to the wild-type waaA sequence. The one or more amino acid mutations may be independently selected from substitutions, insertions, or deletions. In some embodiments, the amino acid mutations are amino acid substitutions. In some embodiments, mutations are selected based on their predicted score as a transmembrane region, using known predictive tools.

In still other embodiments, the transmembrane domain is a transmembrane domain of yhbM (SEQ ID NO: 19), ycgG (SEQ ID NO: 22), djlA (SEQ ID NO: 23), lpxK (SEQ ID NO: 25), F11O (SEQ ID NO: 26), motA (SEQ ID NO: 27), htpx (SEQ ID NO: 28), pgaC (SEQ ID NO: 29), ygdD (SEQ ID NO: 30), hemr (SEQ ID NO: 31), or ycls (SEQ ID NO: 32), or a derivative thereof. The derivative may have one or more amino acid mutations relative to the wild-type *E. coli* sequence. In some embodiments, the transmembrane domain may have from about 1 to about 10, or from about 1 to about 8, or from about 1 to about 5, or from about 1 to about 3 mutations relative to the wild-type *E. coli* sequence. In some embodiments, the one or more amino acid mutations may be independently selected from substitutions, insertions, and deletions. In some embodiments, the amino acid mutations are amino acid substitutions. In some embodiments, mutations are selected based on their predicted score as a transmembrane region, using known predictive tools.

In other aspects, the invention provides polynucleotides comprising a nucleotide sequence encoding an engineered P450 enzyme described above. The polynucleotide may be codon optimized for expression in *E. coli* in some embodiments. In another example, the polynucleotide may comprise a nucleotide sequence encoding at least one engineered P450 enzyme with one or more cytochrome P450 reductase (CPR) enzymes described herein as a translational fusion or operon. Such polynucleotides may further comprise, in addition to sequences encoding the engineered P450 enzyme, one or more expression control elements. For example, the polynucleotide may comprise one or more promoters or transcriptional enhancers, ribosomal binding sites, transcription termination signals, as expression control elements. The polynucleotide may be inserted within any suitable vector, including an expression vector, and which may be contained within any suitable host cell for expression. The polynucleotide may be designed for introduction and/or protein expression in any suitable host cell, including bacterial cells such as *E. coli* cells.

In other aspects, the invention provides *E. coli* host cells expressing the engineered P450 enzyme, either integrated into the genome, or extrachromosomally (e.g., on a plasmid). In some embodiments, the P450 enzyme is expressed by a strong promoter, such as T7, T5, T3, or Trc, or a promoter having promoter strength in *E. coli* equal to or more than T7, T5, T3, or Trc. The promoter may be a strong constitutive *E. coli* promoter or a coliphage promoter, or a variant thereof. Deuschle et al., *Promoters of Escherichia coli: a hierarchy of in vivo strength indicates alternate structures*, EMBO J. 5(11): 2987-2994 (1986); parts.i-gem.org/Promoters/Catalog/Ecoli/Constitutive. When expressed from a plasmid, the plasmid may be a low or high copy number plasmid (e.g., p5, p10, p20). In another embodiment, the P450 gene is chromosomally integrated into the genome of the host *E. coli* cell, which may further include tandem repeats of the gene to increase the expression level. See US 20110236927, which is hereby incorporated by reference in its entirety.

The *E. coli* cells may be fed the desired P450 substrate for chemical transformation, or biochemical pathways may be expressed in the host cell to generate the substrate in vivo.

In some embodiments the bacterial host expresses one or more recombinant biosynthetic pathways. For example, an *E. coli* host cell may express one or more recombinant biosynthetic pathways that include at least 1, at least 2, at least 3, at least 4, or at least 5 recombinant enzymes. The biosynthetic pathways may produce a secondary metabolite through the overexpression of at least 1, at least 2, at least 3, at least 4, or at least 5 foreign genes. In these or other embodiments, the *E. coli* host cell may overexpress at least 1, at least 2, at least 3, at least 4, or at least 5 *E. coli* genes. Overexpression of several *E. coli* genes and/or foreign genes can produce substantial cell stress responses. Where these pathways include one or more P450 enzymes, these stress responses can be substantially higher. For example, as shown herein, P450 enzymes can induce substantial overexpression of the IbpA protein, a protein that is overexpressed under conditions of protein aggregation and cell stress. For example, overexpression of native *E. coli* genes as well as foreign genes can result in conditions of protein aggregation that induce a cell stress response (e.g., as observed by overexpression of IbpA).

In various embodiments, the invention results in reduced cell stress such that the *E. coli* cell does not exhibit a substantially stressed phenotype during culturing, or the cell stress is minimized. Cell stress may be assessed by measuring the expression of various cell stress proteins including, but not limited to, IbpA, DnaK, GrpE, and GroL. In some embodiments, methods of the invention do not result in overexpression of the cell stress protein IbpA. In this context, overexpression refers to at least two times the IbpA expression level of the parent strain. In some embodiments, the engineering of the P450 enzyme of the invention may be guided by testing IbpA expression in cultures. For example, a determination of the length of the truncation of the P450 enzyme and/or the anchor size and/or sequence may be guided by IbpA expression levels in the culture.

In some embodiments, at least one foreign gene is expressed by a strong promoter, such as T7, T5, T3, or Trc, or a promoter having promoter strength in *E. coli* equal to or more than T7, T5, T3, or Trc. The promoter may be a strong constitutive *E. coli* promoter or a coliphage promoter, or a variant thereof. Deuschle et al., *Promoters of Escherichia coli: a hierarchy of in vivo strength indicates alternate structures*, EMBO J. 5(11): 2987-2994 (1986); parts.i-gem.org/Promoters/Catalog/Ecoli/Constitutive. In an embodiment, the genes are expressed from a plasmid, which may be a low or high copy number plasmid (e.g., p5, p10, p20). In another embodiment, the genes are chromosomally integrated into the genome of the host *E. coli* cell, which may further include tandem repeats of the gene to increase the expression level. See US 20110236927, which is hereby incorporated by reference in its entirety.

In some embodiments, the *E. coli* produces a compound from isopentyl pyrophosphate (IPP) and/or dimethylallyl pyrophosphate DMAPP, such as a terpene or terpenoid compound. In an exemplary embodiment, the *E. coli* cell may overexpress at least one gene in the MEP pathway, which is endogenous to *E. coli*. The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. In the MEP pathway, pyruvate and D-glyceraldehyde-3-phosphate are converted via a series of reactions to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, ispA, and ispB. In some embodiments, one or more terpenoid compounds are produced at least in part by metabolic flux through an MEP pathway. In an embodiment, the *E. coli* host cell may express at least one additional copy of a dxs and/or idi gene. In some embodiments, the *E. coli* host as at least one additional copy of dxs, ispD, ispF, and/or idi gene, so as to overexpress these gene products.

In various embodiments, the *E. coli* cell expresses one or more biosynthetic pathways that include at least one membrane-anchored engineered P450 enzyme as described herein. In some embodiments, the P450 enzyme is not strongly expressed, but the more efficient membrane anchoring in accordance with the invention allows for sufficient activity without stronger expression. In various embodiments, the *E. coli* cell expresses at least 1, at least 2, at least 3, at least 4, or at least 5 P450 enzymes, which may operate in serial fashion in a biosynthetic pathway.

In some embodiments, the P450 enzyme is expressed from a strong (e.g., constitutive or inducible) *E. coli* or coliphage promoter, or variant thereof (e.g., Trc, T7, T5, or T3, or variant thereof). While overexpression of P450 enzymes can induce significant cell stress, the membrane anchoring system in accordance with the invention renders the P450-membrane association more productive, with less protein misfolding and/or aggregation, which would otherwise induce cell stress.

In various embodiments, the *E. coli* host cell expresses the engineered P450 enzyme alongside one or more cytochrome P450 reductase (CPR) partner that regenerates the P450 enzyme. As used herein, the term "cytochrome P450 reductase partner" or "CPR partner" refers to a cytochrome P450 reductase capable of regenerating the cofactor component of the cytochrome P450 oxidase of interest for oxidative chemistry. The CPR may be a natural CPR partner for the P450 enzyme, and in other embodiments, the CPR partner is not the natural CPR partner for the P450 enzyme. In nature, cytochrome P450 reductase is a membrane protein generally found in the endoplasmic reticulum. It catalyzes pyridine nucleotide dehydration and electron transfer to membrane bound cytochrome P450s. CPRs may be derived from any species that naturally employs P450 biochemistry, including: *Zingiber* sp., *Barnadesia* sp., *Hyoscyamus* sp., *Latuca* sp., *Nicotiana* sp., *Citrus* sp., *Artemesia* sp., *Arabidopsis* sp, *Stevia* sp., *Bacillus* sp., *Pleurotus* sp., *Cichorium* sp., *Helianthus* sp., and *Physcomitrella* sp., *Taxus* sp., *Rosa* sp., *Cymbopogon* sp., *Humulus* sp., *Pogostemon* sp., and *Cannabis* sp. Exemplary CPRs include those from *Stevia rebaudiana* (e.g., SEQ ID NO: 33, 40, 41, and 42), *Arabidopsis thaliana* (SEQ ID NO: 34, 37, 38, and 39), *Taxus cuspidata* (SEQ ID NO: 35), *Atemisia annua* (SEQ ID NO:36), and *Pelargonium graveolans* (SEQ ID NO: 43). In various embodiments, the wild-type CPR or derivative thereof is expressed separately from the P450 enzymes (e.g., from the same or different operon), or in some embodiments as a translational fusion with the P450 enzyme. Generally, CPR derivatives comprise amino acid sequences having at least 70%, or at least 80%, or at least 90%, or at least 95% identity to the wild-type sequence (e.g., SEQ ID NOS: 33-43), and which can be employed in the various embodiments.

In an embodiment, the CPR may be expressed as a translational fusion protein with an engineered P450 enzyme. The CPR may be fused to the P450 enzyme through a linker. Exemplary linker sequences can be predominantly serine, glycine, and/or alanine, and may be from three to one hundred amino acids in various embodiments. Linker sequences include, for example, GSG, GSGGGS (SEQ ID NO: 44), GSGEAAAK (SEQ ID NO: 45), GSGEAAAKEAAAK (SEQ ID NO: 46), and GSGMGSSSN (SEQ ID NO: 47).

In some embodiments, the invention allows for better control of P450 enzyme efficiency, by allowing for efficient ratios of expression of P450 enzymes in relation to the CPR partner (when expressed separately). In some embodiments, the ratio of the expression levels of the P450 enzyme(s) and the CPR partners may range from about 5:1 to about 1:5, for example, about 5:1, or about 4:1, or about 3:1, or about 2:1, or about 1:1, or about 1:2, or about 1:3, or about 1:4, or about 1:5. For example, the ratio of the expression levels of the P450 enzyme(s) and the CPR partner may be from about 2:1 to about 1:2. In various embodiments, the CPR may also be modified to include at least one membrane anchor sequence derived from an *E. coli* protein as described herein. In an embodiment, the *E. coli* cell expresses a single CPR protein, and optionally expresses more than one P450 enzyme.

In various embodiments, the *E. coli* host cell expresses a biosynthetic pathway that produces a secondary metabolite selected from a terpenoid, alkaloid, cannabinoid, steroid, saponin, glycoside, stilbenoid, polyphenol, antibiotic, polyketide, fatty acid, or non-ribosomal peptide. In certain embodiments, the *E. coli* cell produces one or more terpenoid compounds. A terpenoid, also referred to as an isoprenoid, is an organic chemical derived from a five-carbon isoprene unit (C5). Several non-limiting examples of terpenoids, classified based on the number of isoprene units that they contain, include: hemiterpenoids (1 isoprene unit), monoterpenoids (2 isoprene units), sesquiterpenoids (3 isoprene units), diterpenoids (4 isoprene units), sesterterpenoids (5 isoprene units), triterpenoids (6 isoprene units), tetraterpenoids (8 isoprene units), and polyterpenoids with a larger number of isoprene units. In an embodiment, the *E. coli* host cell produces a terpenoid selected from a monoterpenoid, a sesquiterpenoid, diterpenoid, a sesterpenoid, or a triterpenoid. Terpenoids represent a diverse class of molecules that provide numerous commercial applications, including in the food and beverage industries as well as the perfume, cosmetic and health care industries. By way of example, terpenoid compounds find use in perfumery (e.g. patchoulol), in the flavor industry (e.g., nootkatone), as sweeteners (e.g., steviol), or therapeutic agents (e.g., taxol) and many are conventionally extracted from plants. Nevertheless, terpenoid molecules are found in ppm levels in nature, and therefore require massive harvesting to obtain sufficient amounts for commercial applications.

Where the chemical species is a terpenoid, the host cell will generally contain a recombinant downstream pathway that produces the terpenoid from IPP and DMAPP precursors. Terpenes such as Monoterpenes (C10), Sesquiterpenes (C15) and Diterpenes (C20) are derived from the prenyl diphosphate substrates, geranyl diphosphate (GPP), farnesyl diphosphate (FPP) and geranylgeranyl diphosphate (GGPP) respectively through the action of a very large group of enzymes called the terpene (terpenoid) synthases. These enzymes are often referred to as terpene cyclases since the product of the reactions are cyclized to various monoterpene, sesquiterpene and diterpene carbon skeleton products. Many of the resulting carbon skeletons undergo subsequence oxygenation by cytochrome P450 hydrolysase enzymes to give rise to large families of derivatives. In various embodiments, the *E. coli* cell expresses a biosynthetic pathway involving the overexpression of a geranyl diphosphate synthase (GPS), a gernanylgeranyl diphosphate synthase (GGPS), a farnsesyl diphosphate synthase (FPS), or a farnesyl geranyl diphosphate synthase (FGPPS).

The product of the invention in some embodiments is one or more oxygenated terpenoids. As used herein, the term "oxygenated terpenoid" refers to a terpene scaffold having one or more oxygenation events, producing a corresponding alcohol, aldehyde, carboxylic acid and/or ketone. In some embodiments, the *E. coli* cell produces at least one terpenoid selected from alpha-sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Sabinene, Steviol, Steviol glycoside, Taxadiene, Thymol, and Valencene, either as a P450 oxygenated product or as a substrate for P450 chemistry.

In another embodiment, the *E. coli* cell produces Valencene and/or Nootkatone. In such an embodiment, the *E. coli* cell may express a biosynthetic pathway that further includes a farnesyl pyrophosphate synthase, a Valencene Synthase, and a Valencene Oxidase (the VO comprising the membrane anchor described herein). Farnesyl pyrophosphate synthases (FPPS) produce farnesyl pyrophosphates from iso-pentyl pyrophosphate (IPP) and dimethylallyl pyrophosphate (DMAPP). An exemplary farnesyl pyrophosphate synthase is ERG20 of *Saccharomyces cerevisiae* (NCBI accession P08524) and *E. coli* ispA. Valencene synthase produces sesquiterpene scaffolds and are described in, for example, US 2012/0107893, US 2012/0246767, and U.S. Pat. No. 7,273,735, which are hereby incorporated by reference in their entireties.

In an embodiment, the *E. coli* cell produces steviol or steviol glycoside (e.g., RebM). Steviol is produced from kaurene by the action of two P450 enzymes, kaurene oxidase (KO) and kaurenoic acid hydroxylase (KAH). After production of steviol, various steviol glycoside products may be produced through a series of glycosylation reactions, which can take place in vitro or in vivo. Pathways and enzymes for production of steviol and steviol glycosides are disclosed in US 2013/0171328, US 2012/0107893, WO 2012/075030, WO 2014/122328, which are hereby incorporated by reference in their entireties.

In various embodiments, the *E. coli* cell may express a biosynthetic pathway involving a geranylgeranyl pyrophosphate synthase (GPPS), a copalyl diphosphate synthase (CPPS), and a kaurene synthase (KS), as well as a kaurene oxidase (KO) and a kaureneoic acid hydroxylase (KAH) having a single pass transmembrane domain derived from an *E. coli* gene. In some embodiments, the biosynthetic pathway may further include or more uridine diphosphate dependent glycosyltransferase enzymes (UGT).

Other biosynthetic pathways for production of terpenoid compounds are disclosed in U.S. Pat. No. 8,927,241, which is hereby incorporated by reference in its entirety.

In various embodiments, *E. coli* cell is cultured to produce the one or more chemical species. For example, the *E. coli* cell may be cultured to produce one or more terpenoid compounds.

While commercial biosynthesis in *E. coli* can be limited by the temperature at which overexpressed and/or foreign enzymes are stable, the substantial improvements in stability of the P450 enzymes described herein, may allow for cultures to be maintained at higher temperatures, resulting in higher yields and higher overall productivity. In some embodiments, the culturing is conducted at about 30° C. or greater, about 31° C. or greater, about 32° C. or greater, about 33° C. or greater, about 34° C. or greater, about 35° C. or greater, about 36° C. or greater, or about 37° C. or greater.

The host cells are further suitable for commercial production of chemical species, and therefor can be productive at commercial scale. In some embodiments, the size of the culture is at least about 100 L, at least about 200 L, at least about 500 L, at least about 1,000 L, or at least about 10,000 L. In an embodiment, the culturing may be conducted in batch culture, continuous culture, or semi-continuous culture.

In various embodiments, methods of the invention further include recovering the one or more chemical species such as one or more terpenoid compounds from the cell culture or from cell lysates. In some embodiments, the culture produces at least about 20 mg/L, at least about 25 mg/L, at least about 30 mg/L, at least about 35 mg/L, at least about 40 mg/L, at least about 45 mg/L, at least about 50 mg/L, at least about 55 mg/L, at least about 60 mg/L, at least about 65 mg/L, at least about 70 mg/L, at least about 75 mg/L, at least about 80 mg/L, at least about 85 mg/L, at least about 90 mg/L, at least about 95 mg/L, at least about 100 mg/L, at least about 150 mg/L, or at least about 200 mg/L of the chemical species.

In some embodiments involving the production of a terpenoid compound, the production of indole is used as a surrogate marker for terpenoid production, and/or the accumulation of indole in the culture is controlled to increase terpenoid production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach as described in U.S. Pat. No. 8,927,241 (which is hereby incorporated by reference), and/or is controlled by chemical means.

The oxidized product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, particularly in relation to terpenoids, oxidized oil is extracted from aqueous reaction medium using an organic solvent, such as an alkane such as heptane, followed by fractional distillation. Terpenoid components of fractions may be measured quantitatively by GC/MS, followed by blending of fractions to generate a desired product profile.

In various embodiments, the recovered chemical species such as one or more terpenoid compounds are incorporated into a product (e.g., a consumer or industrial product). For example, the product may be a flavor product, a fragrance product, a sweetener, a cosmetic, a cleaning product, a detergent or soap, or a pest control product. In some embodiments, the oxygenated product recovered is nootkatol and/or nootkatone, and the product is a flavor product selected from a beverage, a chewing gum, a candy, or a flavor additive, or the product is an insect repellant. In some embodiments, the oxygenated product is steviol or a steviol glycoside, which is provided as a sweetener, or is incorporated into beverages or food products.

The invention further provides methods of making products such as foods, beverages, texturants (e.g., starches, fibers, gums, fats and fat mimetics, and emulsifiers), pharmaceutical products, tobacco products, nutraceutical products, oral hygiene products, and cosmetic products, by incorporating the chemical species produced herein. The higher yields of such species produced in embodiments of the invention can provide significant cost advantages as well as sustainability.

EXAMPLES

Example 1. Identification of Candidate *E. coli* Genes with Membrane Anchor Sequences FIG. 1 illustrates the N-terminal membrane anchor concept. Previously, P450 enzymes were expressed in *E. coli* by truncation of at least a portion of the P450 N-terminal transmembrane region, with the addition of an 8 amino acid peptide (MALLLAVF; SEQ ID NO: 61) derived from bovine P45017α. See, for example, Barnes H J, et al., Expression and enzymatic activity of recombinant cytochrome P450 17α-hydroxylase in *Escherichia coli*, *PNAS* 88: 5597-5601 (1991); Ajikumar P K, et al., Isoprenoid pathway optimization for taxol precursor overproduction in *Escherichia coli*, *Science* 330(6000): 70-74 (2010). However, activity of these P450 constructs in *E. coli* was generally limiting, making eukaryotes such as yeast the preferred hosts for oxidative transformations involving P450 enzymes. In part, the lack of P450 productivity in *E. coli* could result from a cell stress response triggered by the non-native membrane anchoring. By engineering P450 proteins to contain an N-terminal anchor derived from an *E. coli* protein that is natively anchored in the inner membrane by its N-terminus (either by single pass or multi-pass transmembrane helices), this cell stress response could be minimized, and other benefits for the functional expression of P450 enzymes might be identified.

Figure 2:
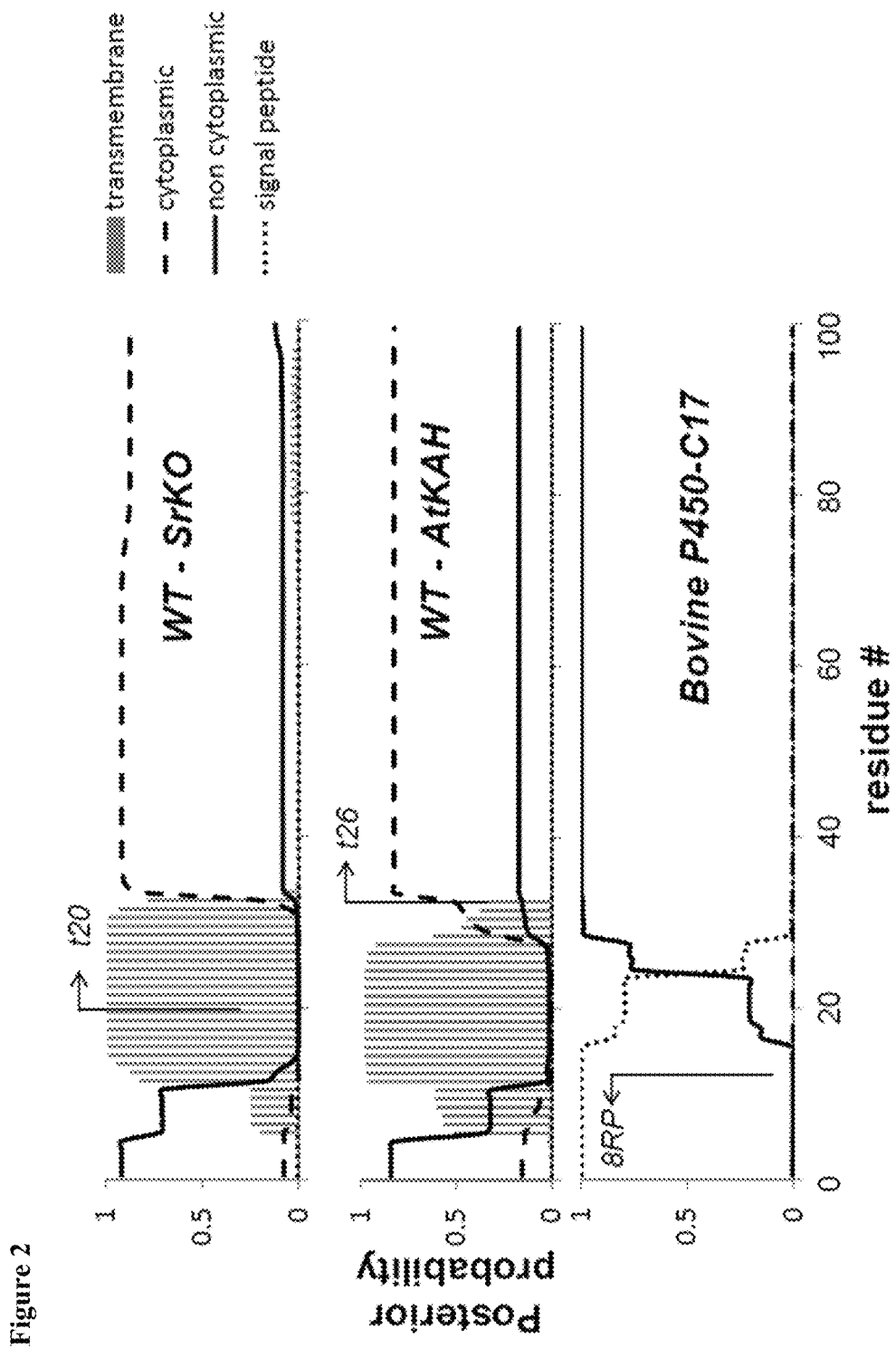
FIG. 2 shows a computational prediction of signal peptides and/or transmembrane helices using the Phobius predictive tool. SrKO and AtKAH are predicted to have an N-terminal transmembrane region. Bovine P450-C17 N-terminus is predicted as a signal peptide.

A proteomic analysis was carried out to identify candidate *E. coli* anchor sequences for functional expression in *E. coli*. Specifically, the EcoGene 3.0 software was used to identify *E. coli* inner membrane proteins that include a C-terminus in the cytoplasm. The Phobius predictive tool was used to assess candidate *E. coli* genes for the presence of signal peptides and/or transmembrane regions. The analysis identified 395 genes which were experimentally determined to be inner membrane proteins. In addition, 85 predicted inner membrane genes were identified. The prediction of transmembrane helices or signal peptides is illustrated in FIG. 2 for three known membrane-anchored P450 enzymes. *Stevia rebaudiana* Kaurene Oxidase (SrKO) and *Arabidopsis thaliana* kaurenoic acid 13-hydroxylase (AtKAH) were predicted to include transmembrane domains. The bovine P450-C17 enzyme was predicted to have a N-terminal signal peptide—8rp.

Example 2. Construction and Functional Analysis of Engineered Valencene Oxidase (VO) Enzymes Various N-terminal anchors based on single pass *E. coli* transmembrane regions were constructed and incorporated into Valencene Oxidase (VO) truncated at residue 30. The Valencene Oxidase is derived from *Stevia rebaudiana* Kaurene Oxidase (SrKO), which has been shown to be functional for oxidative transformation of Valencene to Nootkatone and Nootkatol, which are sesquiterpene compounds. Constructs were cloned into the p5Trc-tc-CPR plasmid which includes a translationally coupled cytochrome P450 reductase (CPR). As a control, the 8rp signal peptide was also incorporated into VO truncated at either residue 20 or residue 30 (8rp-t20 or 8rp-t30).

Figure 3:
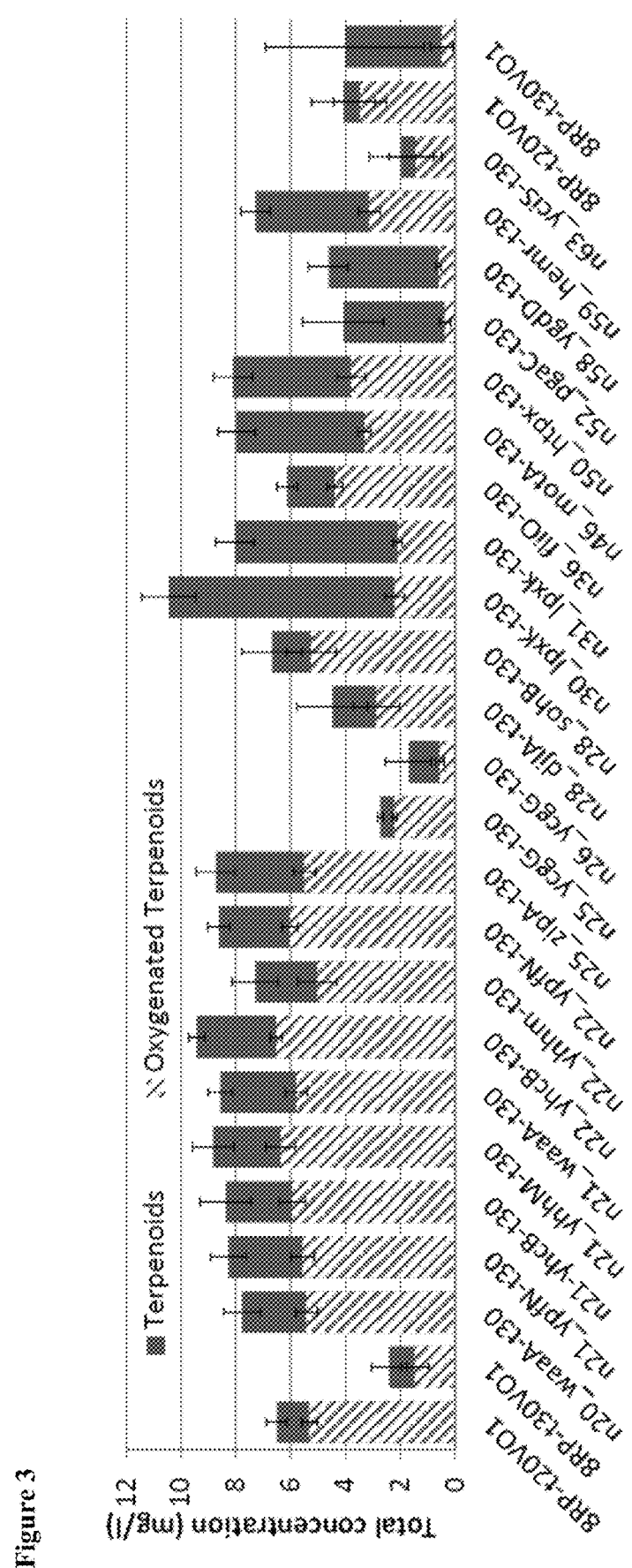
FIG. 3 shows the total terpenoid flux and oxygenated terpenoid formation upon expression in *E. coli* of Valencene Oxidase (VO) enzymes truncated at residue 30 and having various *E. coli* anchors. The *E. coli* cells express a valencene synthesis pathway, producing the valencene substrate. Results with control VO enzymes having the 8rp signal peptide with truncation of 20 or 30 residues are also shown. Enzymes include a translationally coupled CPR.

The engineered VO enzymes with candidate *E. coli* anchor sequences were expressed in host *E. coli* cells that produce valencene through a recombinant valencene synthesis pathway. The cells were incubated at 30° C. for 48 hours in 96 dispensing well plates with a dodecane overlayer. As shown in FIG. 3, many of the *E. coli* anchored enzymes outperformed the 8rp-t20 and 8rp-t30 constructs in both total terpenoid flux and oxygenated product formation.

Figure 4:
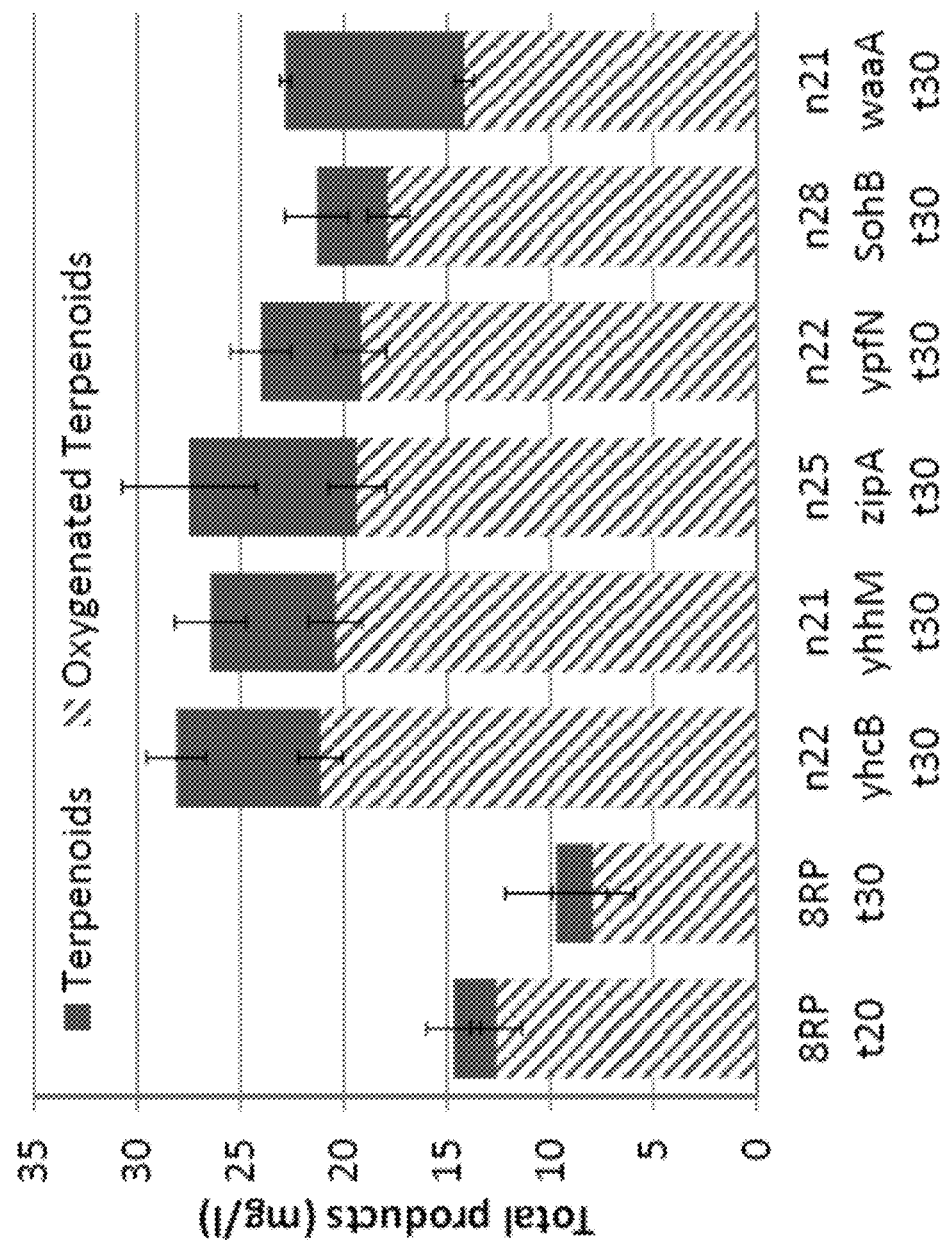
FIG. 4 shows the total terpenoid flux and oxygenated terpenoid formation upon expression in *E. coli* of VO enzymes truncated at residue 30 with candidate *E. coli* anchors (sequences from yhcB, yhhM, zipA, ypfN, sohB, and waaA).

Lead VO constructs with *E. coli* anchor sequences were assessed. The constructs were expressed in host *E. coli* cells which were incubated at 30° C. for 48 hours in 24 dispensing well plates with a vegetable oil overlay. Consistent with previous results, the *E. coli* anchored enzymes outperformed the 8rp-t20 and 8rp-t30 constructs in both total terpenoid flux and oxygenated product formation (FIG. 4).

Figure 5:
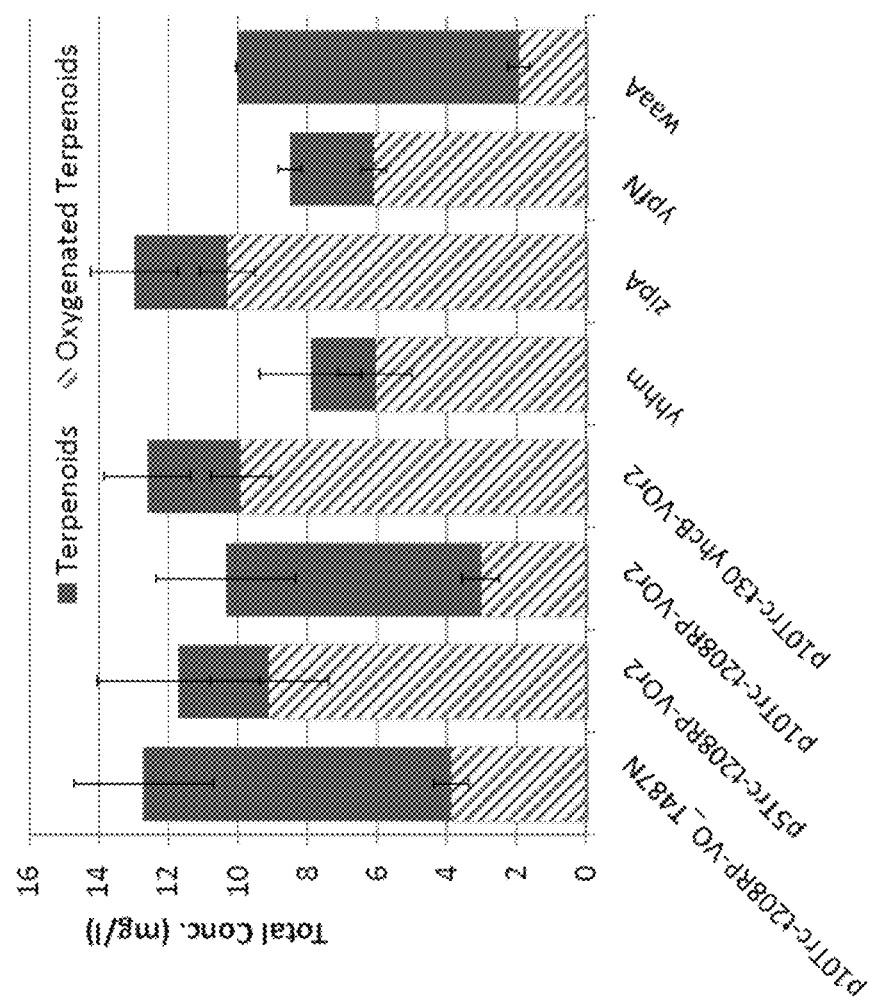
FIG. 5 shows the total terpenoid flux and oxygenated terpenoid formation upon expression of VO enzymes from a p10 expression plasmid or a p5 expression plasmid. While the 8RP anchor shows markedly decreased productivity at the higher expression level provided by a p10 plasmid, the higher expression level has little impact on productivity with the VO enzymes engineered with the *E. coli* anchor sequences.

The effects of increased expression of engineered P450 constructs on *E. coli* cells were evaluated. Specifically, VO constructs with lead *E. coli* anchor sequences were cloned into a p10 plasmid and expressed in valencene-producing *E. coli* cells which were incubated at 30° C. for 48 hours in 24 dispensing well plates with a vegetable oil overlay. As shown in FIG. 5, overexpression of 8rp anchored P450 enzymes (from the p10 plasmid) resulted in reduced activity including a three-fold loss in the formation of oxygenated terpenoids compared to a weaker expressed enzyme (from a p5 plasmid). In contrast, the P450 enzymes with *E. coli* anchors (particularly yhcB and ZipA) showed only a modest loss of oxygenated product when expressed from a p10 plasmid. Further, P450 enzymes with *E. coli* anchors expressed from a p10 plasmid produced as much product as the 8rp anchored enzyme expressed from a p5 plasmid. Accordingly, the *E. coli* anchored P450 enzymes allowed for high functional expression in *E. coli* cells.

Figure 6:
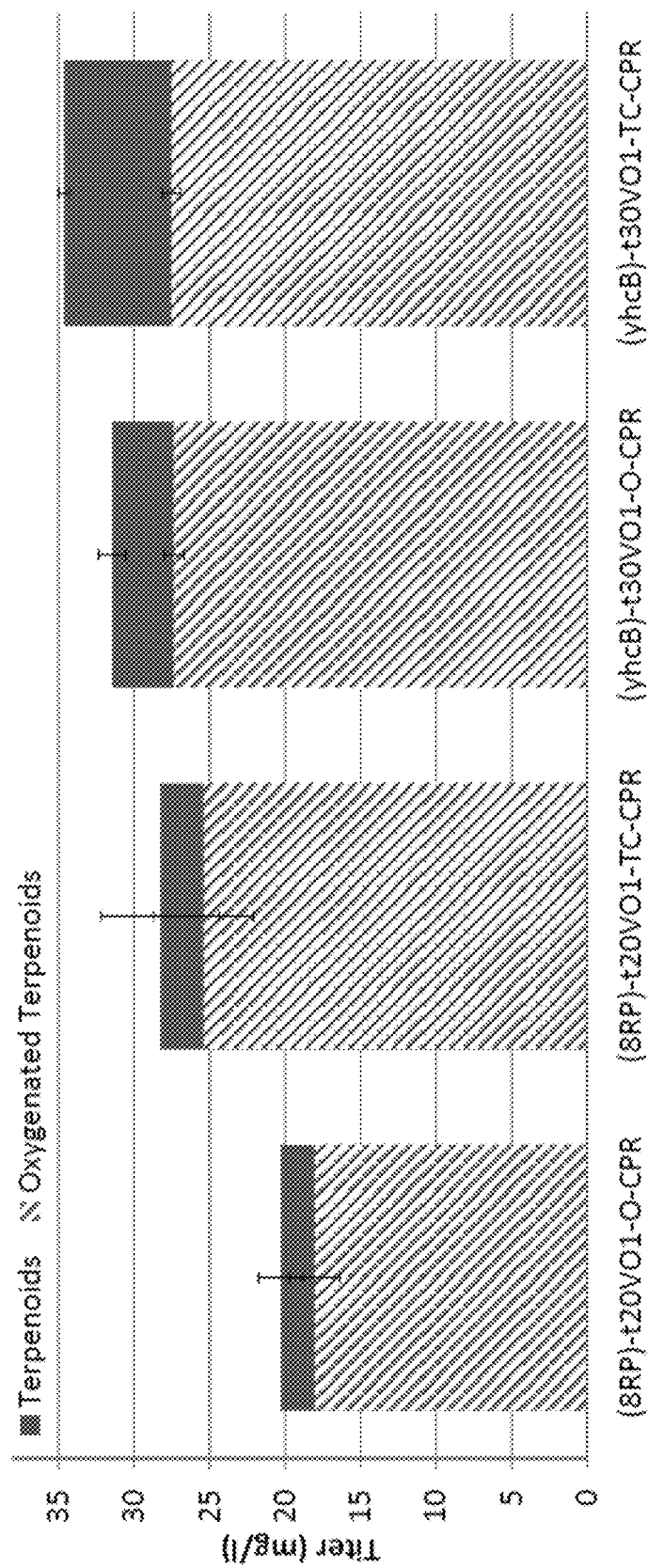
FIG. 6 shows the total terpenoid flux and oxygenated terpenoid titers upon expression of the VO enzymes in a valencene-producing *E. coli* strain with a cytochrome P450 reductase (CPR) partner. The VO enzymes were expressed with the CPR either as separate proteins from the same operon or were translationally coupled.

Functional expression with the CPR partner (from *Stevia*) was also assessed. In particular, the CPR enzyme was expressed in *E. coli* cells with the P450 enzymes either in the same operon or translationally coupled from one plasmid. The cells were incubated at 30° C. for 48 hours in 24 dispensing well plates with a vegetable oil overlay. It was observed that membrane anchors based on native *E. coli* sequences (e.g., yhcB) provided increased oxygenated titer when translationally coupled to a CPR partner or when expressed separately (FIG. 6). In addition, cells with the *E. coli* anchors grew to a higher final OD and with less emulsion, suggesting that the cells are less stressed, despite overexpressing an upstream MEP pathway and downstream terpenoid biosynthesis (Nootkatone) pathway.

Figure 7:
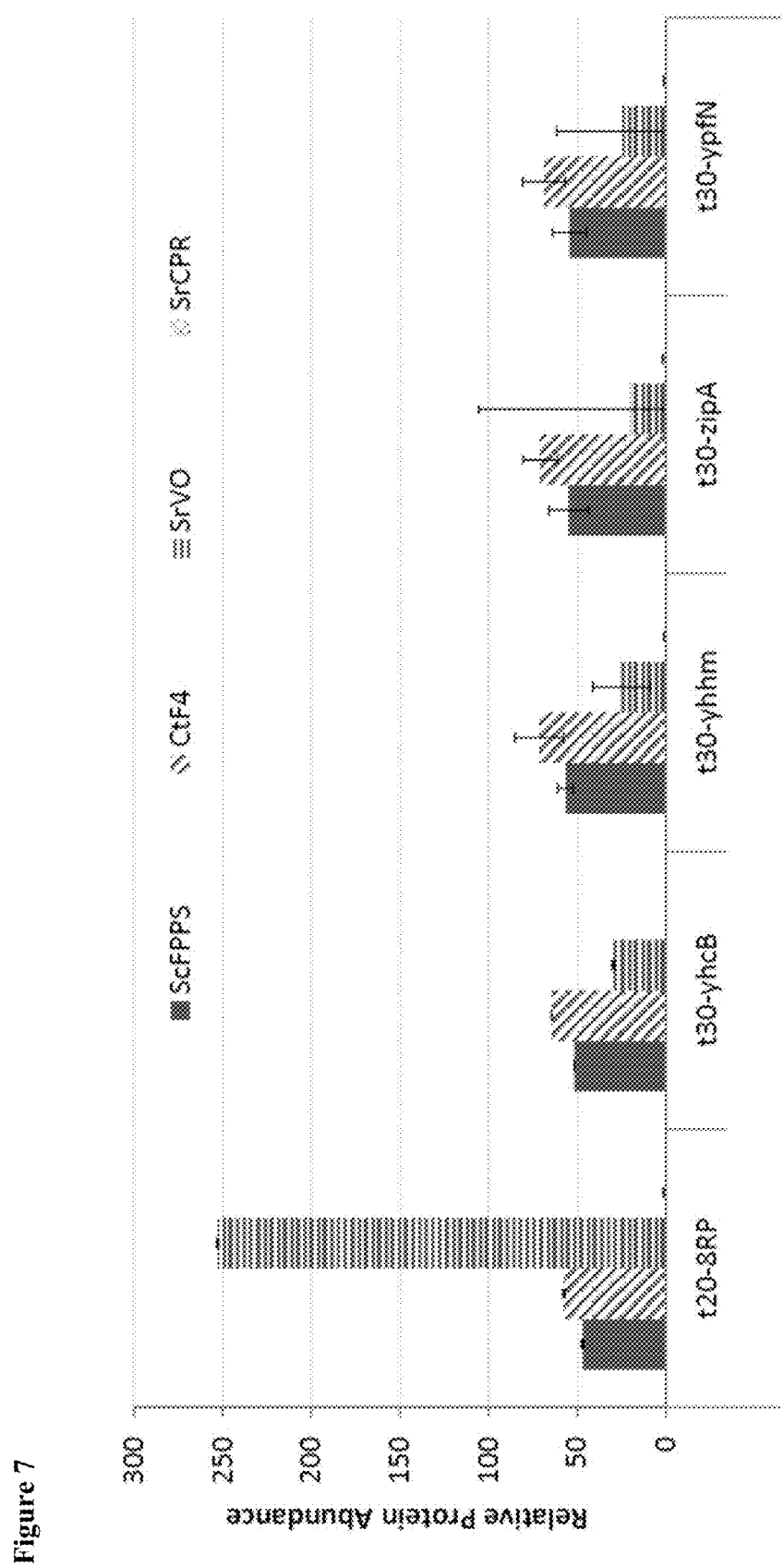
FIG. 7 shows the level of VO protein expression with candidate N-terminal *E. coli* anchors (i.e., yhcB, yhhm, zipA, and ypfN), in comparison to t20-8RP. All four of the native *E. coli* anchors show lower total VO expression compared to 8RP, which results in a significantly lower relative VO/CPR ratio.

During translation initiation, N-terminal sequences can significantly affect the expression of a protein. As such, a comparison was conducted to examine VO expression and VO/CPR ratio with different N-terminal anchor regions. As shown in FIG. 7, four anchors tested (yhcB, yhhm, zipA, and ypfN) showed lower total VO expression compared to the control 8rp anchor, allowing for a five-fold lower expression relative to CPR expression. This ratio is important for efficient P450 electron transfer without deleterious effects on coupling efficiency.

Figure 8:
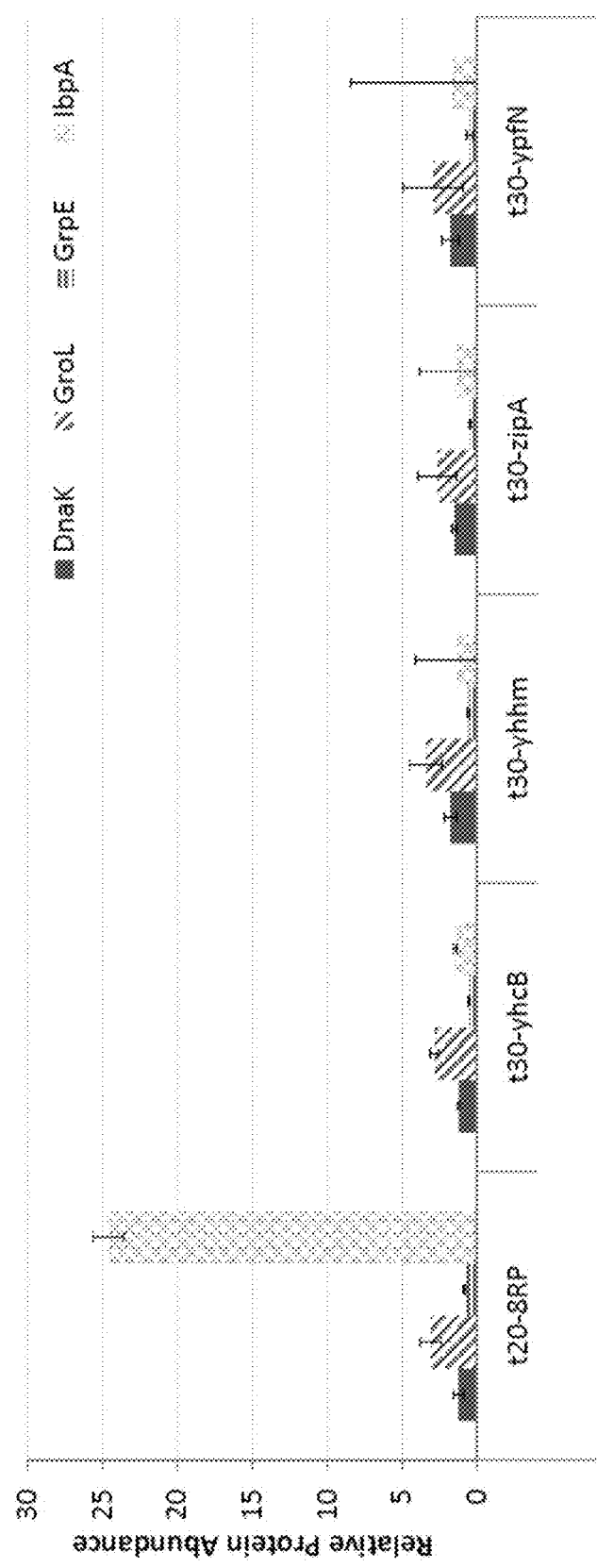
FIG. 8 shows the cellular stress response to VO expression with different N-terminal *E. coli* anchors, by assessing known *E. coli* stress response proteins. The IbpA protein, which is overexpressed in *E. coli* under conditions of high protein aggregation, was highly expressed in response to t20-8RP expression, but not with the native *E. coli* anchors.

A proteomics approach was undertaken to assess cellular stress response to variable P450 expression. For example, IbpA, which is overexpressed in *E. coli* under conditions of high protein aggregation and stress, is strongly expressed with the 8rp anchored P450 enzyme, but not with the enzymes with *E. coli* anchors (FIG. 8).

Figure 9:
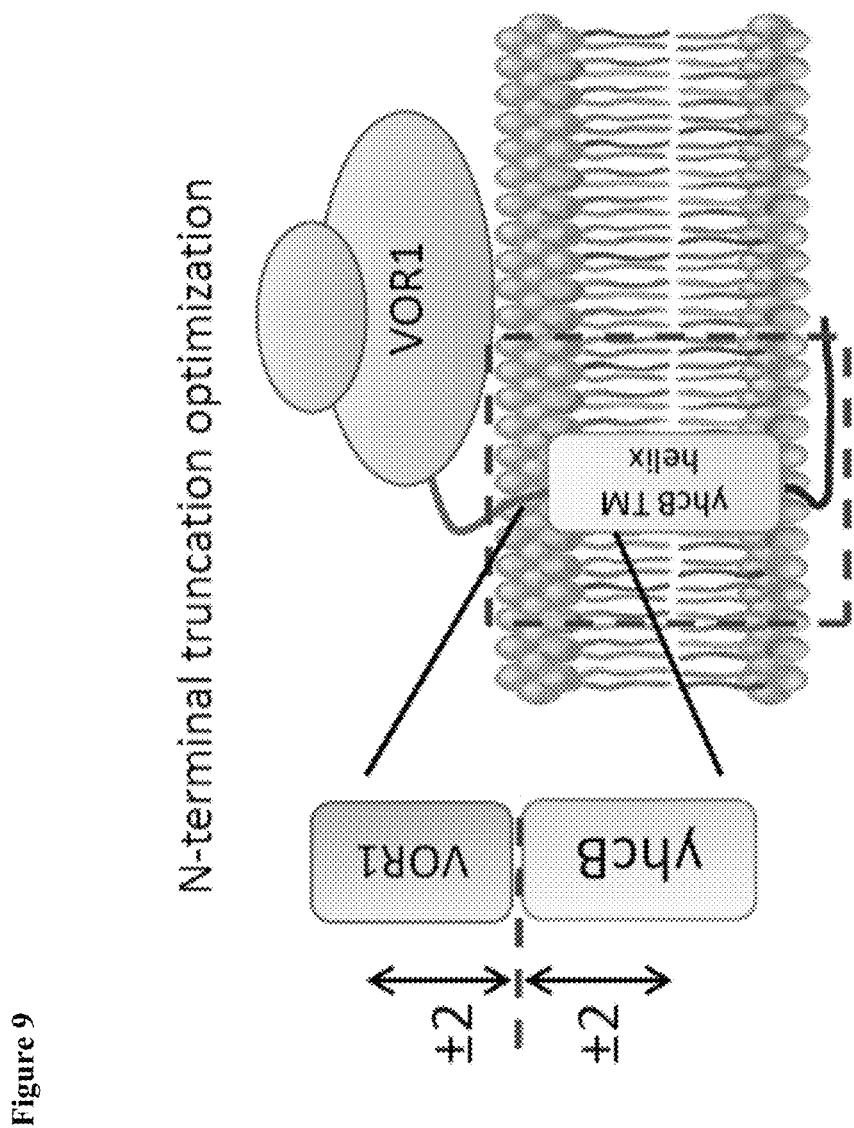
FIG. 9 is a diagram showing the optimization of truncation length and anchor length of yhcB anchored VO enzymes.

The yhcB-anchored VO enzyme was further analyzed to determine the impact of anchor and P450 truncation length on overall productivity (FIG. 9). Variants with truncations in anchor and P450 sequences were generated using the GeneArt technology and subcloned into a p5T7-BCD18 screening plasmid. A list of the variants is provided in Table 2.

TABLE 2

| Truncation Optimization |
| --- |
| n20yhcB_t28VOR1 |
| n20yhcB_t29VOR1 |
| n20yhcB_t30VOR1 |
| n20yhcB_t31VOR1 |
| n20yhcB_t32VOR1 |
| n21yhcB_t28VOR1 |
| n21yhcB_t29VOR1 |
| n21yhcB_t30VOR1 |
| n21yhcB_t31VOR1 |
| n21yhcB_t32VOR1 |
| n22yhcB_t28VOR1 |
| n22yhcB_t29VOR1 |

TABLE 2-continued

Truncation Optimization n22yhcB_t31VOR1
n22yhcB_t32VOR1
n23yhcB_t28VOR1
n23yhcB_t29VOR1
n23yhcB_t30VOR1
n23yhcB_t31VOR1
n23yhcB_t32VOR1
n24yhcB_t28VOR1
n24yhcB_t29VOR1
n24yhcB_t30VOR1
n24yhcB_t31VOR1
n24yhcB_t32VOR1

Figure 10:
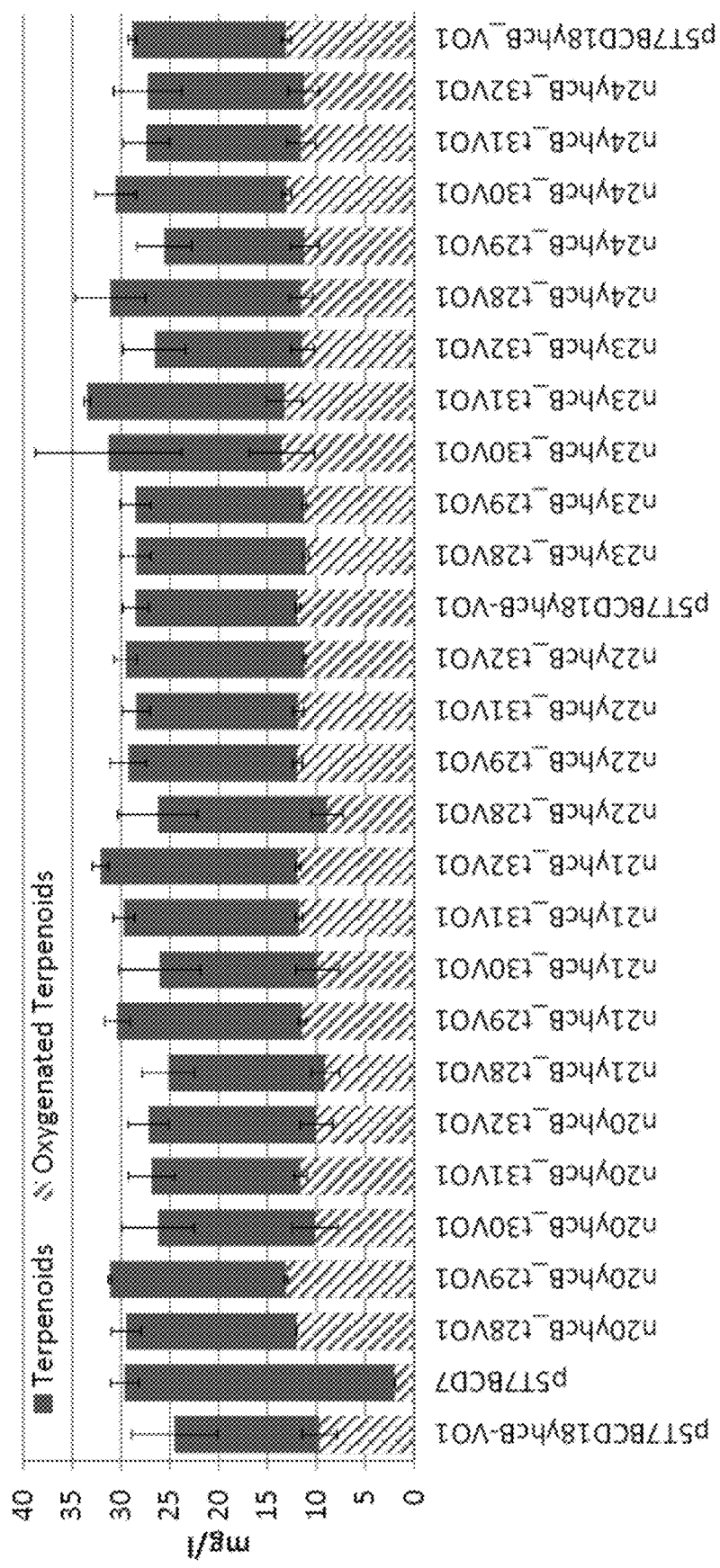
FIG. 10 shows the total terpenoid flux and oxygenated terpenoid production with various truncated and yhcB anchored VO enzymes. Truncations varied from 28 to 32 amino acids of the Valencene Oxidase, and the anchored VO included from 20 to 24 amino acids of the yhcB N-terminus.

The variants were assayed for product formation in a MEP/FPPS/VS integrated *E. coli* strain. The *E. coli* cells were incubated at 30° C. for 48 hours in 96 dispensing well plates with a dodecane overlay. Products were subsequently extracted with ethyl acetate. As shown in FIG. 10, modification of the anchor and P450 truncation lengths has only modest impact on overall productivity. For example, the n20yhcB-t29VO1 construct yielded an approximately 1.2-fold increase in total terpenoid flux and oxygenated products. These results suggest that the *E. coli* anchored P450 enzymes are relatively robust to changes in anchor and truncation length.

Example 3. Construction and Functional Analysis of Additional Engineered P450 Enzymes Modified *Arabidopsis thaliana* kaurenoic acid 13-hydroxylase (AtKAH) and *Stevia rebaudiana* Kaurene Oxidase (SrKO) enzymes with *E. coli* anchor sequences were generated.

Engineered enzymes were produced with the AtKAH enzymes truncated at position 26. The N-terminus of the truncated AtKAH enzyme is shown below:

```
                                            (SEQ ID NO: 61)
t25 AtKAH
HVYGRAVVEQWR (SEQ ID NO: 62)
t26 AtKAH
VYGRAVVEQWR
```

Figure 11:
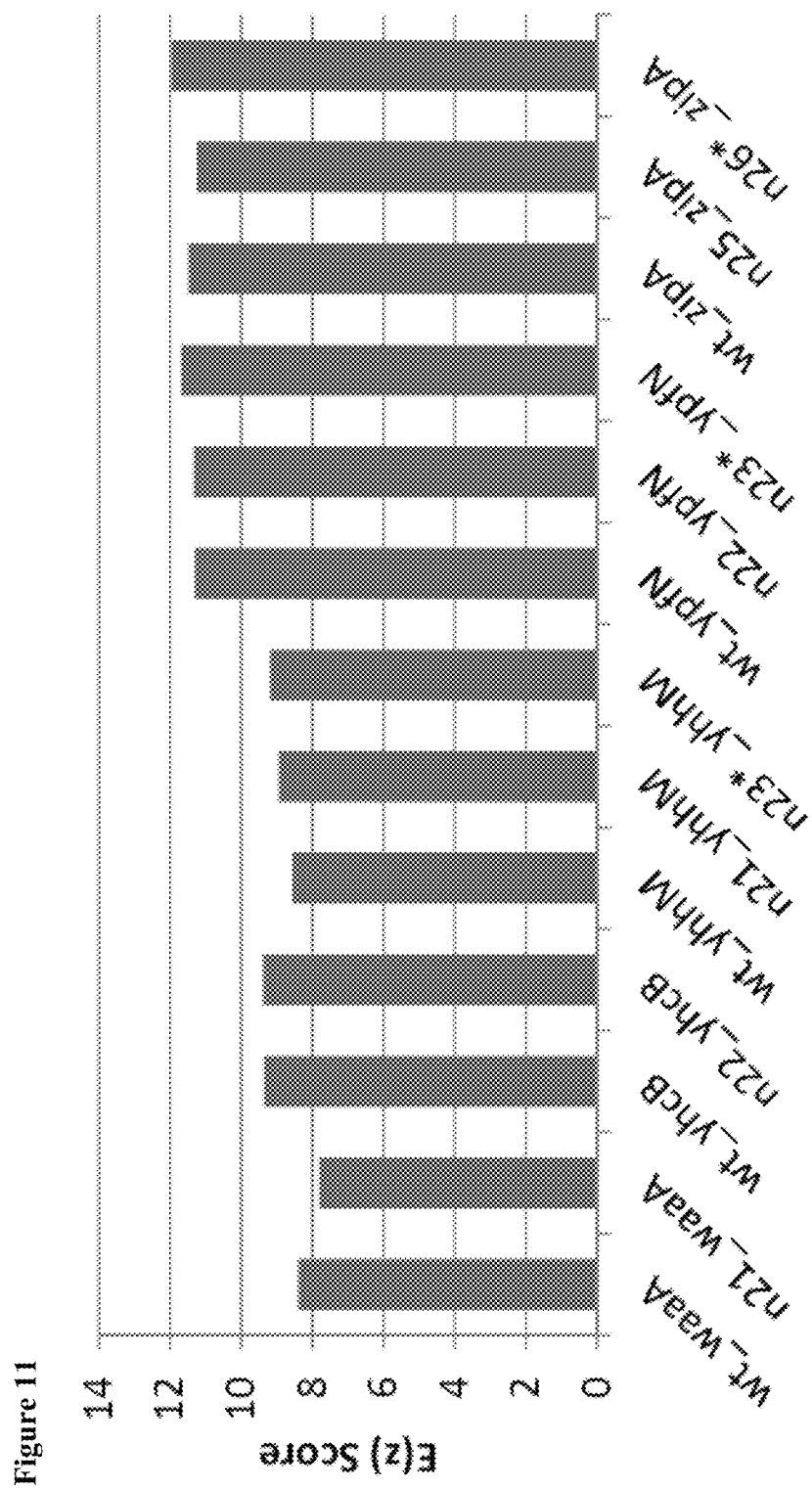
FIG. 11 shows the E(z) score of AtKAH enzymes truncated at residue 26 with various *E. coli* anchors. Wild-type (wt) is the score in the wild-type *E. coli* enzyme, nXX is the number of residues taken from the protein for a swap with the *E. coli* anchor, and the name of the source protein. Asterisks show truncations not tested with VO. E(z) score estimates the suitability of a protein sequence for insertion into a cell membrane based on statistics from solved transmembrane crystal structures.

The E(z) scoring system was used to guide truncation of the *E. coli* anchor sequence by similarity of scoring to the parent protein (FIG. 11). Eight combinations of *E. coli* anchored N-terminal segments and AtKAH truncation lengths were selected for in vivo screening.

*E. coli* membrane anchors (e.g., zipA, yhhm, and yhcB) were also incorporated into SrKO for production of kaurenoic acid in *E. coli*. The N-terminus of the truncated SrKO enzyme is shown below:

```
                                            (SEQ ID NO: 63)
t29 SrVO
FWYLKSYTSARR (SEQ ID NO: 64)
t30 SrVO
WYLKSYTSARR
```

Figure 12A:
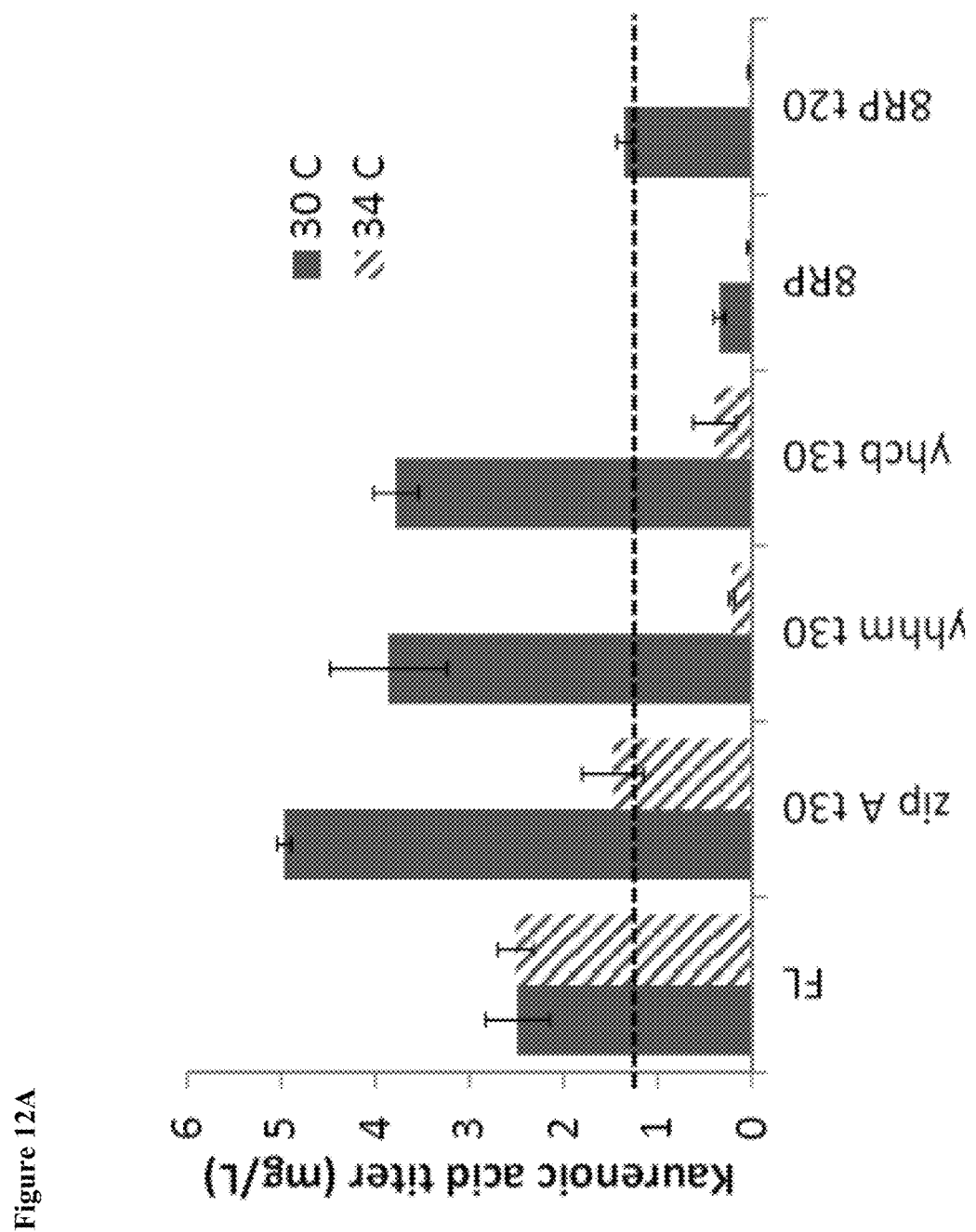
FIG. 12A shows kaurenoic acid formation upon expression in kaurene-producing strains of SrKO enzymes engineered by truncation at residue 30, and with addition of *E. coli* anchors. The enzymes were expressed from a p5 plasmid along with a cytochrome P450 reductase (CPR) in the same operon. Kaurenoic acid formation is shown at 30° C. and 34° C.
Figure 12B:
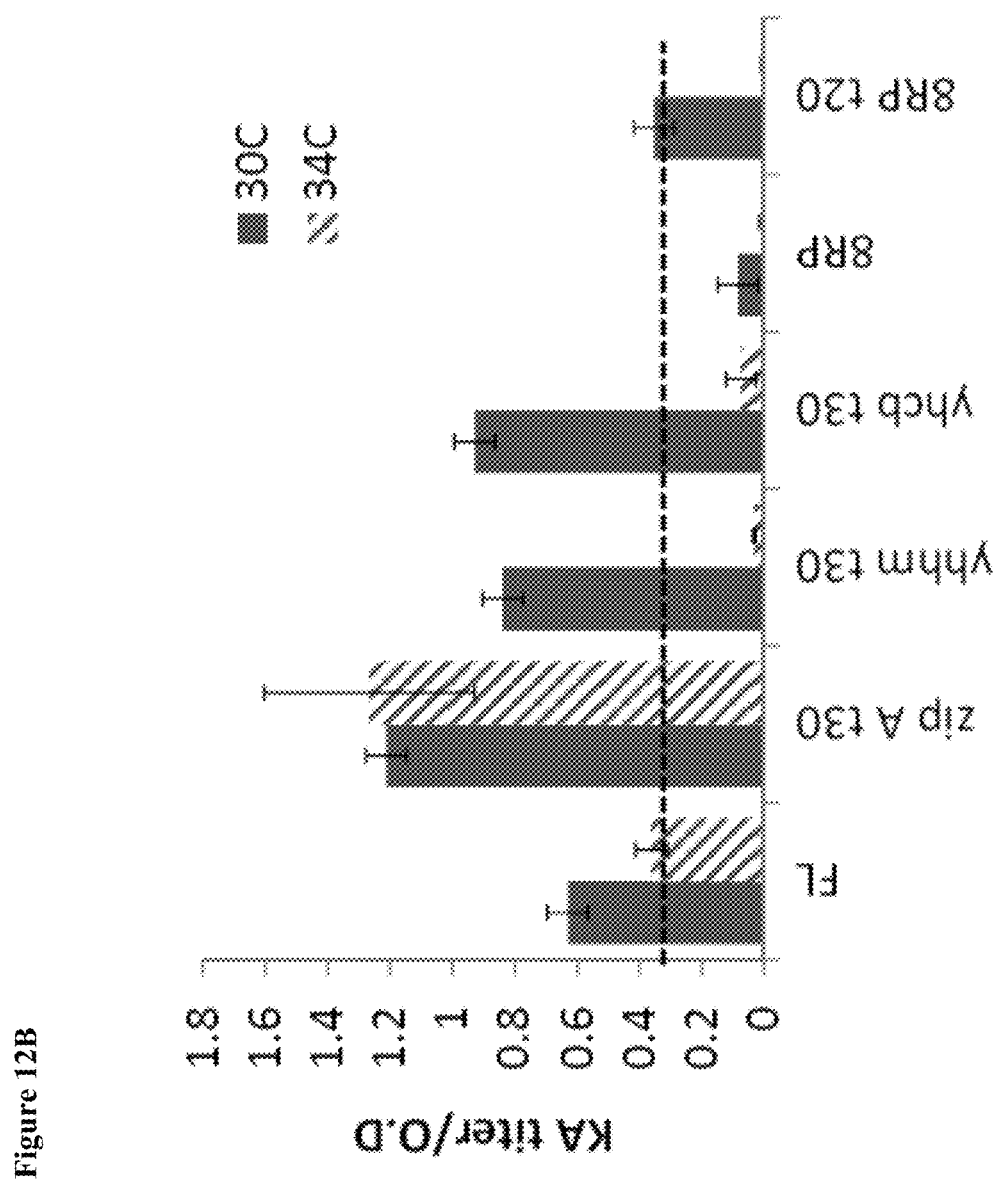
FIG. 12B shows the kaurenoic acid formation/OD of the *E. coli* strains.

The constructs were cloned into the p5Trc plasmid which include an operon expressed CPR. The *E. coli* cells were incubated at either 30° C. or 34° C. for 72 hours in 96 dispensing well plates. Similar to results obtained with the engineered VO enzymes, variant SrKO enzymes with *E. coli* anchor sequences also showed improved activity compared to enzymes with 8rp anchor sequences. Particularly, as shown in FIG. 12A, the zipA anchored P450 enzyme produced the highest kaurenoic acid titer (about 5 mg/L). In addition, all SrKO variants showed a drop in activity at 34° C. FIG. 12B shows that the final OD is higher in all variants except zipA when incubated at 34° C.

Figure 13:
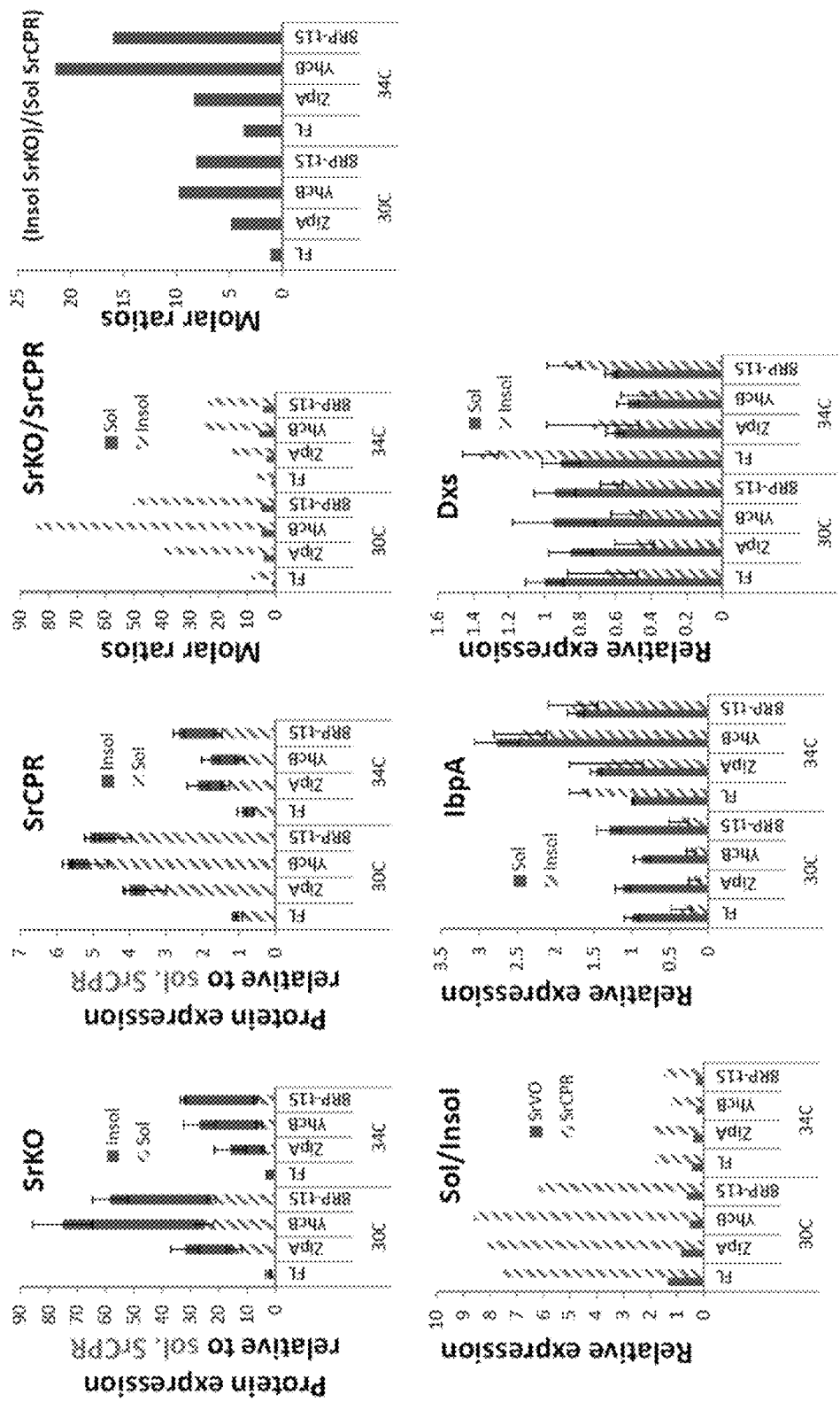
FIG. 13 shows a detailed proteomic analysis of SrKO expressing cells. The relative abundance of various pathway and stress response proteins is assessed. SrKO is significantly over expressed when paired with non-native anchors (*E. coli* or 8rp) although the increased expression is dampened at higher temperatures (34° C. vs. 30° C.). IbpA stress response is also significantly increased at the higher temperature.

A proteomics analysis was undertaken to examine the relative abundance of various pathway and stress response proteins in cells expressing SrKO. Both soluble and insoluble cell fractions were analyzed by tryptic digest proteomics. As shown in FIG. 13, SrKO enzymes with either *E. coli* anchors zipA and yhcB or control anchor 8rP all showed higher expressions than full-length SrKO at 30° C. and 34° C. Similar results were seen in the insoluble fractions, including higher expression of the upstream pathway enzyme dxs. At the higher temperature of 34° C., there was also an increase in the stress response gene IbpA in the insoluble fractions.

In summary, P450 enzymes with *E. coli* anchor sequences showed improvement in total terpenoid flux and oxygenated terpenoid formation, and provided higher catalytic efficiency and reduced stress response, as compared to 8rp anchored P450 enzymes. This N-terminal engineering approach is broadly applicable to *E. coli* cells having several overexpressed genes, including complete biosynthetic pathways, and including one or multiple P450 enzymes, where managing cell stress is crucial to obtaining commercial yields.

Sequences

P450 ENZYMES

>ZzHO [*Zingiber zerumbet*]
MEAISLFSPFFFITLFLGFFITLLIKRSSRSSVHKQQVLLASLPPSPPRLPLIGNIHQLVGGNPHR
ILLQLARTHGPLICLRLGQVDQVVASSVEAVEEIIKRHDLKFADRPRDLTFSRIFFYDGNAVVMTP
YGGEWKQMRKIYAMELLNSRRVKSFAAIREDVARKLTGEIAHKAFAQTPVINLSEMVMSMINAIVI
RVAFGDKCKQQAYFLHLVKEAMSYVSSFSVADMYPSLKFLDTLTGLKSKLEGVHGKLDKVFDEIIA
QRQAALAAEQAEEDLIIDVLLKLKDEGNQEFPITYTSVKAIVMEIFLAGTETSSSVIDWVMSELIK
NPKAMEKVQKEMREAMQGKTKLEESDIPKFSYLNLVIKETLRLHPPGPLLFPRECRETCEVMGYRV
PAGARLLINAFALSRDEKYWGSDAESFKPERFEGISVDFKGSNFEFMPFGAGRRICPGMTFGISSV
EVALAHLLFHFDWQLPQGMKIEDLDMMEVSGMSATRRSPLLVLAKLIIPLP (SEQ ID NO: 1)

>BsGAO [*Barnadesia spinosa*]
MELTLTTSLGLAVFVFILFKLLTGSKSTKNSLPEAWRLPIIGHMHHLVGTLPHRGVTDMARKYGSL
MHLQLGEVSTIVVSSPRWAKEVLITYDITFANRPETLTGEIVAYHNTDIVLSPYGEYWRQLRKLCT
LELLSAKKVKSFQSLREEECWNLVKEVRSSGSGSPVDLSESIFKLIATILSRAAFGKGIKDQREFT
EIVKEILRLTGGFDVADIFPSKKILHHLSGKRAKLTNIHNKLDSLINNIVSEHPGSRTSSSQESLL
DVLLRLKDSAELPLTSDNVKAVILDMFGAGTDTSSATIEWAISELIRCPRAMEKVQTELRQALNGK -continued ERIQEEDIQELSYLKLVIKETLRLHPPLPLVMPRECREPCVLAGYEIPTKTKLIVNVFAINRDPEY
WKDAETFMPERFENSPINIMGSEYEYLPFGAGRRMCPGAALGLANVELPLAHILYYFNWKLPNGAR
LDELDMSECFGATVQRKSELLLVPTAYKTANNSA (SEQ ID NO: 2)

>HmPO [Hyoscyamus muticus]
MQFFSLVSIFLFLSFLFLLRKWKNSNSQSKKLPPGPWKLPLLGSMLHMVGGLPHHVLRDLAKKYGP
LMHLQLGEVSAVVVTSPDMAKEVLKTHDIAFASRPKLLAPEIVCYNRSDIAFCPYGDYWRQMRKIC
VLEVLSAKNVRSFSSIRRDEVLRLVNFVRSSTSEPVNFTERLFLFTSSMTCRSAFGKVFKEQETFI
QLIKEVIGLAGGFDVADIFPSLKFLHVLTGMEGKIMKAHHKVDAIVEDVINEHKKNLAMGKTNGAL
GGEDLIDVLLRLMNDGGLQFPITNDNIKAIIFDMFAAGTETSSSTLVWAMVQMMRNPTILAKAQAE
VREAFKGKETFDENDVEELKYLKLVIKETLRLHPPVPLLVPRECREETEINGYTIPVKTKVMVNVW
ALGRDPKYWDDADNFKPERFEQCSVDFIGNNFEYLPFGGGRRICPGISFGLANVYLPLAQLLYHFD
WKLPTGMEPKDLDLTELVGVTAARKSDLMLVATPYQPSRE (SEQ ID NO: 3)

>LsGAO [Lactuca sativa]
MELSITTSIALATIVFFLYKLATRPKSTKKQLPEASRLPIIGHMHHLIGTMPHRGVMDLARKHGSL
MHLQLGEVSTIVVSSPKWAKEILTTYDITFANRPETLTGEIIAYHNTDIVLAPYGEYWRQLRKLCT
LELLSVKKVKSFQSIREEECWNLVKEVKESGSGKPINLSESIFTMIATILSRAAFGKGIKDQREFT
EIVKEILRQTGGFDVADIFPSKKFLHHLSGKRARLTSIHKKLDNLINNIVAEHHVSTSSKANETLL
DVLLRLKDSAEFPLTADNVKAIILDMFGAGTDTSSATVEWAISELIRCPRAMEKVQAELRQALNGK
EKIQEEDIQDLAYLNLVIRETLRLHPPLPLVMPRECREPVNLAGYEIANKTKLIVNVFAINRDPEY
WKDAEAFIPERFENNPNNIMGADYEYLPFGAGRRMCPGAALGLANVQLPLANILYHFNWKLPNGAS
HDQLDMTESFGATVQRKTELLLVPSF (SEQ ID NO: 4)

>NtEAO [Nicotiani tabacum]
MQFFSLVSIFLFLSFLFLLRKWKNSNSQSKKLPPGPWKIPILGSMLHMIGGEPHHVLRDLAKKYGP
LMHLQLGEISAVVVTSRDMAKEVLKTHDVVFASRPKIVAMDIICYNQSDIAFSPYGDHWRQMRKIC
VMELLNAKNVRSFSSIRRDEVVRLIDSIRSDSSSGELVNFTQRIIWFASSMTCRSAFGQVLKGQDI
FAKKIREVIGLAEGFDVVDIFPTYKFLHVLSGMKRKLLNAHLKVDAIVEDVINEHKKNLAAGKSNG
ALGGEDLIDVLRLMNDTSLQFPITNDNIKAVIVDMFAAGTETSSTTWVWAMAEMMKNPSVFTKAQ
AEVREAFRDKVSFDENDVEELKYLKLVIKETLRLHPPSPLLVPRECREDTDINGYTIPAKTKVMVN
VWALGRDPKYWDDAESPKPERFEQCSVDFFGNNFEFLPFGGGRRICPGMSFGLANLYLPLAQLLYH
FDYNKLPTGIMPRDLDLTELSGITIARKGGLYLNATPYQPSRE (SEQ ID NO: 5)

>CpVO [Citrus x paradisi]
MELPLKSIALTIVIVTVLIVAWRVLNWVWLRPKKLEKFLRQQGLKGNSYRLLFGDLKENSIELKEA
KARPLSLDDDIAIRVNPFLHKLVNDYGKNSFMWFGPTPRVNIMNPDQIKAIFTKINDFQKVNSIPL
ARLLIVGLATLEGEKWAKHRKLINPAFHQEKLKLMLPAFYLSCIEIITKWEKQMSVEGSSELDVWP
YLANLTSDVISRTAFGSSYEEGRRIFQLQAELAELTMQVFRSVHIPGWRFLPTKRNRRMKEIDKEI
RASLMGIIKNREKAMRAGEAANNDLLGILMETSFREIEEHGNNKNVGFSMNDVIEECKLFYFAGQE
TTSVLLNWTMVLLSKHQDWQERARQEVLQVFGNNKPDYDGLNHLKIVQMILYEVLRLYPPVTVLSR
AVFKETKLGNLTLPAGVQIGLPMILVHQDPELWGDDAVEFKPERFAEGISKAAKNQVSYFPFALGP
RICVGQNFALVEAKMATAMILQNYSFELSPSYVHAPTAVPTLHPELGTQLILRKLYNCKNN (SEQ ID
NO: 6)

>AaAO [Artemesia annua]
MKSILKAMALSLITSIALATILLFVYKFATRSKSTKKSLPEPWRLPIIGHMHHLIGTTPHRGVRDL
ARKYGSLMHLQLGEVPTIVVSSPKWAKEILTTYDITFANRPETLTGEIVLYHNTDVVLAPYGEYWR
QLRKICTLELLSVKKVKSFQSLREEECWNLVQEIKASGSGRPVNLSENVFKLIATILSRAAFGKGI
KDQKELTEIVKEILRQTGGFDVADIFPSKKFLHHLSGKRARLTSLRKKIDNLIDNLVAEHTVNTSS
KTNETLLDVLLRLKDSAEFPLTSDNIKAIILDMFGAGTDTSSSTIEWAISELIKCPKAMEKVQAEL
RKALNGKEKIHEEDIQELSYLNMVIKETLRLHPPLPLVLPRECRQPVNLAGYNIPNKTKLIVNVFA
INRDPEYWKDAEAFIPERFENSSATVMGAEYEYLPFGAGRRMCPGAALGLANVQLPLANILYHFNW
KLPNGVSYDQIDMTESSGATMQRKTELLLVPSF (SEQ ID NO: 7)

>AtKO [Arabidopsis thaliana]
MAFFSMISILLGFVISSFIFIFFFKKLLSFSRKNMSEVSTLPSVPVVPGFPVIGNLLQLKEKKPHK
TFIRWSEIYGPIYSIKMGSSSLIVLNSTETAKEAMVTRFSSISTRKLSNALTVLTCDKSMVATSDY
DDFHKLVKRCLLNGLLGANAQKRKRHYRDALIENVSSKLHAHARDHPQRPVNFRAIFEHELFGVAL
KQAFGKDVESIYVKELGVTLSKDEIFKVLVHDMMEGAIDVDWRDFFPYLKWIPNKSFEARIQQKHK
RRLAVMNALIQDRLKQNGSESDDDCYLNFLMSEAKTLTKEQIAILVWETIIETADTTLVTTEWAIY
ELAKHPSVQDRLCKEIQNVCGGEKFKEEQLSQVPYLNGVFHETLRKYSPAPLVPIRYAHEDTQIGG
YHVPAGSEIAINIYGCNMDKKRWERPEDWWPERFLDDGKYETSDLHKTMAFGAGKRVCAGALQASL
MAGIAIGRLVQEFEWKLRDGEEENVDTYGLTSQKLYPLMAIINPRRS (SEQ ID NO: 8)

>SrKO [Stevia rebaudiana]
MDAVTGLLTVPATAITIGGTAVALAVALIFWYLKSYTSARRSQSNHLPRVPEVPGVPLLGNLLQLK
EKKPYMTFTRWAATYGPIYSIKTGATSMVVVSSNEIAKEALVTRFQSISTRNLSKALKVLTADKTM
VAMSDYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNKKFEN
TIQQMYIRREAVMKSLIKEHHKKRIASGEKLNSYIDYLLSEAQTLTDQQLLMSLWEPIIESSDTTMV
TTEWAMYELAKNPKLQDRLYRDIKSVCGSEKITEEHLSQLPYITAIFHETLRRHSPVPIIPLRHVH
EDTVLGGYHVPAGTELAVNIYGCNMDKNVWENPEEWNPERFMKENETIDFQKTMAFGGGKRVCAGS
LQALLTASIGIGRMVQEFEWKLKDMTQEEVNTIGLTTQMLRPLRAIIKPRI (SEQ ID NO: 9)

>PpKO [Physcomitrella patens]
MAKHLATQLLQQWNEALKTMPPGFRTAGKILVWEELASNKVLITIALAWVLLFVARTCLRNKKRLP
PAIPGGLPVLGNLLQLTEKKPHRTFTAWSKEHGPIFTIKVGSVPQAVVNNSEIAKEVLVTKFASIS
KRQMPMALRVLTRDKTMVAMSDYGEEHRMLKKLVMTNLLGPTTQNKNRSLRDDALIGMIEGVLAEL KASPTSPKVVNVRDYVQRSLFPPALQQVFGYIPDQVEVLELGTCVSTWDMFDALVVAPLSAVINVD
WRDFFPALRWIPNRSVEDLVRTVDFKRNSIMKALIRAQRMRLANLKEPPRCYADIALTEATHLTEK
QLEMSLWEPIIESADTTLVTSEWAMYEIAKNPDCQDRLYREIVSVAGTERMVTEDDLPNMPYLGAI
IKETLRKYTPVPLIPSRFVEEDITLGGYDIPKGYQILVNLFAIANDPAVWSNPEKWDPERMLANKK
VDMGFRDFSLMPFGAGKRMCAGITQAMFIIPMNVAALVQHCEWRLSPQEISNINNKIEDVVYLTTH
KLSPLSCEATPRISHRLP (SEQ ID NO: 10)

>BmVO [*Bacillus megaterium*]
MTIKEMPQPKTFGELKNLPLLNTDKPVQALMKIADELGEIFKFEAPGRVTRYLSSQRLIKEACDES
RFDKNLSQALKFVRDFAGDGLATSWTHEKNWKKAHNILLPSFSQQAMKGYHAMMVDIAVQLVQKWE
RLNADEHIEVPEDMIRLTLDTIGLCGFNYRFNSFYRDQPHPFITSMVRALDEAMNKLQRANPDDPA
YDENKRQFQEDIKVMNDLVDKIIADRKASGEQSDDLLTHMLNGKDPETGEPLDDENIRYQIITFLI
AGHETTSGLLSFALYFLVKNPHVLQKAAEEAARVLVDPVPSYKQVKQLKYVGMVLNEALRLWPTIP
AFSLYAKEDTVLGGEYPLEKGDELMVLIPQLHRDKTIWGDDVEEFRPERFENPSAIPQHAFKPFGN
GQRACIGQQFALHEATLVLGMMLKHFDFEDHTNYELDIKETLTLKPEGFVVKAKSKKIPLGGIPSP
STEQSAKKVRKKAENAHNTPLLVLYGSNMGTAEGTARDLADIAMSKGFAPQVATLDSHAGNLPREG
AVLIVTASYNGHPPDNAKQFVDWLDQASADEVKGVRYSVFGCGDKNWATTYQKVPAFIDETLAAKG
AENIADRGEADASDDFEGTYEEWREHMWSDVAAYFNLDIENSEDNKSTLSLQFVDSAADMPLAKMH
GAFSTNVVASKELQQPGSARSTRHLEIELPKEASYQEGDHLGVIPRNYEGIVNRVTARFGLDASQQ
IRLEAEEEKLAHLPLAKTVSVEELLQYVELQDPVTRTQLRAMAAKTVCPPHKVELEALLEKQAYKE
QVLAKRLTMLELLEKYPACEMKFSEFIALLPSIRPRYYSISSSPRVDEKQASITVSVVSGEAWSGY
GEYKGIASNYLAELQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYVQHVMEQDGKKLIEL
LDQGAHFYICGDGSQMAPAVEATLMKSYADVHQVSEADARLWLQQLEEKGRYAKDVWAG (SEQ ID
NO: 11)

>PsVO [*Pleurotus sapidus*]
MRYGCAAVALFYLTAMGKLHPLAIIPDYKGSMAASVTIFNKRTNPLDISVNQANDWPWRYAKTCVL
SSDWALHEMIIHLNNTHLVEEAVIVAAQRKLSPSHIVFRLLEPHWVVTLSLNALARSVLIPEVIVP
IAGFSAPHIFQFIRESFTNFDWKSLYVPADLESRGFPVDQLNSPKFHNYAYARDINDMWTTLKKFV
SSVLQDAQYYPDDASVAGDTQIQAWCDEMRSGMGAGMTNFPESITTVDDLVNMVTMCIHIAAPQHT
AVNYLQQYYQTFVSNKPSALFSPLPTSIAQLQKYTESDLMAALPLNAKRQWLLMAQIPYLLSMQVQ
EDENIVTYAANASTDKDPIIASAGRQLAADLKKLAAVFLVNSAQLDDQNTPYDVLAPEQLANAIVI
(SEQ ID NO: 12)

>PoLO [*Pleurotus ostreatus*]
MAPTMSLSRSALKNVHLPYMVQHPEPTDCSTAMKHAAEGYDRARQMIAFLFDILDYESSVPQKFTP
EEKKEKYTWSHSDKFPPHLAIIPEDIDVPAYIIFSIVRLVQTLSIMSGIQCNERLAPGPEQNTMEK
LTKWNAERHKNQGWVKDMFNEPNIGLRNDWYTDAVFAQQFFTGPNPTTITLASDTWMKAFTEEAAS
QGKRDLISLFRSAPPNSFYVQDFSDFRARMGAKPDEELCATSDGGVTRYGCAAVALFYLPPTGELH
PLAIVPDYKGSMAASITLFNKRVDPSDASVDQANDWPWRYAKTCVLSADWVLHEMIIHLNNTHLVQ
EAVIVAVQRTLPDSHIVFRLLKPHWVVTLSLNAQARSVLIPEVIVPIAGFSELRIFQFVGHAFTNF
DWKALYVPTDLEFRGFPLDRLDDDKFHNYAYAKDIKDMWMALRKFVSSVLKDGKYYPDDSAVAADA
QIQDWCDEMRSEKGAGMKKFPESISTLDDLIDMVTMCIHIAAPQHTAVNYLQQYYQTFVPNKPSAL
FSPLPTLLSQLESYTESDLMAALPLGAKQEWLLMAQVPYLLSKEVEQDGNIVTYAGTASNNEDPII
AAAGKELSADLVILAGVFLKNSEKLDDQNTAYNVLAPDQLANAIVI (SEQ ID NO: 13)

>CiVO [*Cichorium intybus*]
MEISIPTTLGLAVIIFIIFKLLTRTTSKKNLLPEPWRLPIIGHMHHLIGTMPHRGVMELARKHGSL
MHLQLGEVSTIVVSSPRWAKEVLTTYDITFANRPETLTGEIVAYHNTDIVLAPYGEYWRQLRKLCT
LELLSNKKVKSFQSLREEECWNLVKDIRSTGQGSPINLSENIFKMIATILSRAAFGKGIKDQKFT
ELVKEILRLTGGFDVADIFPSKKLLHHLSGKRAKLTNIHNKLDNLINNIIAEHPGNRTSSSQETLL
DVLLRLKESAEFPLTADNVKAVILDMFGAGTDTSSATIEWAISELIRCPRAMEKVQTELRQALNGK
ERIQEEDLQELNYLKLVIKETLRLHPPLPLVMPRECREPCVLGGYDIPSKTKLIVNVFAINRDPEY
WKDAETFMPERFENSPITVMGSEYEYLPFGAGRRMCPGAALGLANVELPLAHILYFNWKLPNGKTF
EDLDMTESFGATVQRKTELLLVPTDFQTLTAST (SEQ ID NO: 14)

>HaGAO [*Helianthus annuus*]
MEVSLTTSIALATIVFFLYKLLTRPTSSKNRLPEPWRLPIIGHMHHLIGTMPHRGVMDLARKYGSL
MHLQLGEVSAIVVSSPKWAKEILTTYDIPFANRPETLTGEIIAYHNTDIVLAPYGEYWRQLRKLCT
LELLSVKKVKSFQSLREEECWNLVQEIKASGSGTPFNLSEGIFKVIATVLSRAAFGKGIKDQKQFT
EIVKEILRETGGFDVADIFPSKKFLHHLSGKRGRLTSIHNKLDSLINNLVAEHTVSKSSKVNETLL
DVLLRLKNSEEPPLTADNVKAIILDMFGAGTDISSATVEWAISELIRCPRAMEKVQAELRQALNGK
ERIKEEEIQDLPYLNLVIRETLRLHPPLPLVMPRECRQAMNLAGYDVANKTKLIVNVFAINRDPEY
WKDAESFNPERFENSNITIMGADYEYLPFGAGRRMCPGSALGLANVQLPLANILYYFKWKLPNGAS
HDQLDMTESFGATVQRKTELMLVPSF (SEQ ID NO: 15)

*E. coli* INNER MEMBRANE PROTEINS

>waaA [*Escherichia coli*]
MLELLYTALLYLIQPLIWIRLWVRGRKAPAYRKRWGERYGFYRHPLKPGGIMLHSVSVGETLAAIP
LVRALRHRYPDLPITVITMTPIGSERVQSAFGKDVQHVYLPYDLPDALNRFLNKVDPKLVLIMETE
LWPNLIAALHKRKIPLVIANARLSARSAAGYAKLGKFVRRLLRRITLIAAQNEEDGARFVALGAKN
NQVIVIGSLKFDISVIPQLAAKAVTLRRQWAPHRPVWIATSTHEGEESVVIAAHQALLQQFPNLLL
ILVPRHPERFPDAINLVRQAGLSYITRSSGEVPSTSTQVVVGDTMGELMLLYGIADLAFVGGSLVE
RGGHNPLEAAAHAIPVLMGPHTFNFKDICARLEQASGLITVIDATTLAKEVSSLLTDADYRSFYGR
HAVEVLYQNQGALQRLLQLLEPYL
PPKTH (SEQ ID NO: 16)

```
>ypfN [Escherichia coli]
MDWLAKYWWILVIVFLVGVLLNVIKDLKRVDHKKFLANKPELPPHRDFNDKWDDDDDWPKKDQPKK
(SEQ ID NO: 17)

>yhcB [Escherichia coli]
MTWEYALIGLVVGIIIGAVAMRFGNRKLRQQQALQYELEKNKAELDEYREELVSHFARSAELLDTM
AHDYRQLYQHMAKSSSSLLPELSAEANPFRNRLAESEASNDQAPVQMPRDYSEGASGLLRTGAKRD
(SEQ ID NO: 18)

>yhbM [Escherichia coli]
MKPFLRWCFVATALTLAGCSNTSWRKSEVLAVPLQPILQQEVILARMEQILASRALTDDERAQLLY
ERGVLYDSLGLRALARNDFSQALAIRPDMPEVFNYLGIYLTQAGNFDAAYEAFDSVLELDPTYNYA
HLNRGIALYYGGRDKLAQDDLLAFYQDDPNDPFRSLWLYLAEQKLDEKQAKEVLKQHFEKSDKEQW
GWNIVEFYLGNISEQTLMERLKADAIDNISLAEHLSETNFYLGKYYLSLGDLDSATALFKLAVANN
VHNFVEHRYALLELSLLGQDQDDLAESDQQ (SEQ ID NO: 19)

>yhhm [Escherichia coli]
MSKPPLFFIVIIGLIVVAASFRFMQQRREKADNDMAPLQQKLVVVSNKREKPINDRRSRQQEVIPA
GISIRYEASFKPQSGGMEQTFRLDAQQYHALTVGDKGILSYKGTRFVSFVGEQ (SEQ ID NO:
20)

>zipA [Escherichia coli]
MMQDLRLILIIVGAIAIIALLVHGFWTSRKERSSMFRDRPLKRMKSKRDDDSYDEDVEDDEGVGEV
RVHRVNHAPANAQEHEAARPSPQHQYQPPYASAQPRQPVQQPPEAQVPPQHAPHPAQPVQQPAYQP
QPEQPLQQPVSPQVAPAPQPVHSAPQPAQQAFQPAEPVAAPQPEPVAEPAPVMDKPKRKEAVIIMN
VAAHHGSELNGELLLNSIQQAGFIFGDMNIYHRHLSPDGSGPALFSLANMVKPGIFDPEMKDFTTP
GVTIFMQVPSYGDELQNFKLMLQSAQHIADEVGGVVLDDQRRMMTPQKLREYQDIIREVKDANA
(SEQ ID NO: 21)

>ycgG [Escherichia coli]
MRNTLIPILVAICLFITGVAILNIQLWYSAKAEYLAGARYAANNINHILEEASQATQTAVNIAGKE
CNLEEQYQLGTEAALKPHLRTIIILKQGIVWCTSLPGNRVLLSRIPVFPDSNLLLAPAIDTVNRLP
ILLYQNQFADTRILVTISDQHIRGALNVPLKGVRYVLRVADDIIGPTGDVMTLNGHYPYTEKVHST
KYHFIIIFNPPPLFSFYRLIDKGFGILIFILLIACAAAFLLDRYFNKSATPEEILRRAINNGEIVP
FYQPVVNGREGILRGVEVLARWKQPHGGYISPAAFIPLAEKSGLIVPLIQSLMNQVARQMNAIASK
LPEGFHIGINFSASHIISPIFVDECLNFRDSFIRRDLNLVLEVTEREPLNVDESLVQRLNILHENG
FVIALDDFGTGYSGLSYLHDLHIDYIKIDHSFVGRVNADPESTRILDCVLDLARKLSISIVAEGVE
TKEQLDYLNQNYITFQQGYYFYKPVTYIDLVKIILSKPKVKVVVE (SEQ ID NO: 22)

>djlA [Escherichia coli]
MQYWGKIIGVAVALLMGGGFWGVVLGLLIGHMFDKARSRKMAWFANQRERQALFFATTFEVMGHLT
KSKGRVTEADIHIASQLMDRMNLHGASRTAAQNAFRVGKSDNYPLREKMRQFRSVCFGRFDLIRMF
LEIQIQAAFADGSLHPNERAVLYVIAEELGISRAQFDQFLRMMQGGAQFGGGYQQQTGGGNWQQAQ
RGPTLEDACNVLGVKPIDDATTIKRAYRKLMSEHHPDKLVAKGLPPEMMEMAKQKAQEIQQAYELI
KQQKGFK
(SEQ ID NO: 23)

>sohB [Escherichia coli]
MELLSEYGLFLAKIVIVVLAIAAIAAIIVNVAQRNKRQRGELRVNNLSEQYKEMKEELAAALMDSH
QQKQWHKAQKKHKQEAKAAKAKAKLGEVAIDSKPRVWVLDFKGSMDAHEVNSLREEITAVLAAFK
PQDQVVLRLESPGGMVHGYGLAASQLQRLRDKNIPLIVIVDKVAASGGYMMACVADKIVSAPFAIV
GSIGVVAQMPNFNRFLKSKDIDIELHTAGQYKRTLILLGENTEEGREKFREELNETHQLFKDFVKR
MRPSLDIEQVATGEHWYGQQAVEKGLVDEINTSDEVILSLMEGREVVNVRYMQRKRLIDRFIGSAA
ESADRLLLRWWQRGQKPLM
(SEQ ID NO: 24)

>lpxK [Escherichia coli]
MIEKIWSGESPLWRLLLPLSWLYGLVSGAIRLCYKLKLKRAWRAPVPVVVVGNLTAGGNGKTPVVV
WLVEQLQQRGIRVGVVSRGYGGKAESYPLLLSADITTAQAGDEPVLIYQRTDAPVAVSPVRSDAVK
AILAQHPDVQIIVIDDGLQHYRLARDVEIVVIDGVRRFGNGWWLPAGPMRERAGRLKSVDAVIVNG
GVPRSGEIPMHLLPGQAVNLRIGIRCDVAQLEHVVAMAGIGHPPRFFAILKMCGVQPEKCVPLADH
QSLNHADVSALVSAGQILVMTEKDAVKCRAFAEENWWYLPVDAQLSGDEPAKLLTQLTLLASGN
(SEQ ID NO: 25)

>fliO [Escherichia coli]
MNNHATVQSSAPVSAAPLLQVSGALIAIIALILAAAWLVKRLGFAPKRTGVNGLKISASASLGARE
RVVVVDVEDARLVLGVTAGQINLLHKLPPSAPTEEIPQTDFQSVMKNLLKRSGRS (SEQ ID
NO: 26)

>motA [Escherichia coli]
MLILLGYLVVLGTVEGGYLMIGGSLGALYQPAELVIIAGAGIGSFIVGNNGKAIKGILKALPLLFR
RSKYTKAMYMDLLALLYRLMAKSRQMGMFSLERDIENPRESEIFASYPRILADSVMLDFIVDYLRL
IISGHMNIFEIEALMDEEIETHESEAEVPANSLALVGDSLPAFGIVAAVMGVVHALGSADRPAAEL
GALIAHAMVGTFLGILLAYGFISPLATVLRQKSAETSKMMQCVKVILLSNLNGYAPPIAVEFGRKT
LYSSERPSFIELEEHV
RAVKNPQQQTTTEEA (SEQ ID NO: 27)

>htpx [Escherichia coli]
MMRIALFLLINLAVMVVFGLVLSLIGIQSSSVQGLMIMALLFGFGGSFVSLLMSKWMALRSVGGEV
```

-continued

```
IEQPRNERERWLVNIVATQARQAGIAMPQVAIYHAPDINAFATGARRDASLVAVSTGLLQNMSPDE
AEAVIAHEISHIANGDMVIMILIQGVVNIFVIFISRILAQLAAGFMGGNRDEGEESNGNPLIYFAV
ATVLELVEGILASIITMWFSRHREFHADAGSAKLVGREKMIAALQRLKTSYEPQEATSMMALCING
KSKSLSELFMTHPPLDKRIEALRTGEYLK (SEQ ID NO: 28)

>pgaC [Escherichia coli]
MINRIVSFFILCLVLCIPLCVAYFHSGELMMRFVFFWPFFMSIMWIVGGVYFWVYRERHWPWGENA
PAPQLKDNPSISIIIPCFNEEKNVEETIHAALAQRYENIEVIAVNDGSTDKTRAILDRMAAQIPHL
RVIHLAQNQGKAIALKTGAAAAKSEYLVCIDGDALLDRDAAAYIVEPMLYNPRVGAVIGNPRIRTR
STLVGKIQVGEYSSIIGLIKRIQRIYGNVFIVSGVIAAFRRSALAEVGYWSDDMITEDIDISWKLQ
LNQWTIFYEPRALCWILMPETLKGLWKQRLRWAQGGAEVELKNMIRLWRKENFRMWPLFFEYCLIT
IWAFTCLVGFIIYAVQLAGVPLNIELTHIAATHTAGILLCILCLLQFIVSLMIENRYEHNLISSLF
WIIWFPVIFWMLSLATTLVSFTRVMLMPKKQRARWVSPDRGILRG (SEQ ID NO: 29)

>ygdD [Escherichia coli]
MTSRFMLIFAAISGFIFVALGAFGAHVLSKTMGAVEMGWIQTGLEYQAFHTLAILGLAVAMQRRIS
IWFYWSSVFLALGTVLFSGSLYCLALSHLRLWAFVTPVGGVSFLAGWALMLVGAIRLKRKGVSHE
(SEQ ID NO: 30)

>hemr [Escherichia coli]
MNVIKTAICTLITLPVGLQAATSHSSSMTKDTITVVATGNQNTVFETPSMVSVVTNDTPWSKNAVT
SAGMLRGVAGLSQTGAGRTNGQTFNLRGYDKSGVLVLVDGVRQLSDMAKSSGTYLDPALVKRIEVV
RGPNSSLYGSGGLGGVVDFRTADAADFLPPGETNGVSLWGNIASGDHSTGSGLTWFGKTEKTDALL
SVIMRKRGSIYQSDGERAPNKEKPAALFAKGSVSITDSNKAGASLRLYRNSTTEPGNPTLTHGDSG
LRDRKTAQNDMQFWYQYAPADNSLINVKSTLYLSDITVKTNGHNKTAEWRNNRTSGVNVVNRSHSL
IFPGAHQLSYGAEYYRQQQKPEGTATLYPEGHIDFTSLYFQDEMTMESYPVNIIVGSRYDRYNSFN
ARAGELNAERLSPRAAMSVSPTDWLMMYGSISSAFRAPTMAEMYRDDVHFYRKGKPNYWVPNLNLK
PENNTTREIGAGIQLDSLLTDNDRLQLKGGYFGTDARNYIATRVDMKRMRSYSYNVSRARIWGWDI
QGNYQSDYVDWMLSYNRTESMDASSREWLGSGNPDTLISDISIPVGHRGVYAGWRAELSAPATHVK
KGDPCQDGYAIHSFSLSYKPVSVKGFEASVTLDNAFNKLAMNGKGVPLSGRTVNLYTRYQW
(SEQ ID NO: 31)

>yciS [Escherichia coli]
MKYLLIFLLVLAIFVISVTLGAQNDQQVTFNYLLAQGEYRISTLLAVLFAAGFAIGWLICGLFWLR
VRVSLARAERKIKRLENQLSPATDVAVVPHSSAAKE (SEQ ID NO: 32)
```

CYTOCHROME P450 REDUCTASE PARTNERS

```
>SrCPR [Stevia rebaudiana]
MQSDSVKVSPFDLVSAAMNGKAMEKLNASESEDPITLPALKMLVENRELLTLFTTSFAVLIGCLVF
LMWRRSSSKKLVQDPVPQVIVVKKKEKESEVDDGKKKVSIFYGTQTGTAEGFAKALVEEAKVRYEK
TSFKVIDLDDYAADDDEYEEKLKKESLAFFFLATYGDGEPTDNAANFYKWFTEGDDKGEWLKKLQY
GVFGLGNRQYEHFNKIAIVVDDKLTEMGAKRLVPVGLGDDDQCIEDDFTAWKELVWPELDQLLRDE
DDTSVTTPYTAAVLEYRVVYHDKPADSYAEDQTHTNGHVVHDAQHPSRSNVAFKKELHTSQSDRSC
THLEFDISHTGLSYETGDHVGVYSENLSEVVDEALKLLGLSPDTYFSVHADKEDGTPIGGASLPPP
FPPCTLRDALTRYADVLSSPKKVALLALAAHASDPSEADRLKFLASPAGKDEYAQWIVANQRSLLE
VMQSFPSAKPPLGVFFAAVAPRLQPRYYSISSSPKMSPNRIHVICALVYETTPAGRIHRGLCSTWM
KNAVPLIESPDCSQASIFVRTSNFRLPVDPKVPVIMIGPGIGLAPFRGFLQERLALKESGTELGSS
IFFFGCRNRKVDFIYEDELNNFVETGALSELIVAFSREGTAKEYVQHKMSQKASDIWKLLSEGAYL
YVCGDAKGMAKDVHRTLHTIVQEQGSLDSSKAELYVKNLQMSGRYLRDVW (SEQ ID NO: 33)

>AtCPR [Arabidopsis thaliana]
MTSALYASDLFKQLKSIMGTDSLSDDVVLVIATTSLALVAGFVVLLWKKTTADRSGELKPLMIPKS
LMAKDEDDDLDLGSGKIRVSIFFGTQTGTAEGFAKALSEEIKARYEKAAVKVIDLDDYAADDDQYE
EKLKKETLAFFCVATYGDGEPTDNAARFSKWFTEENERDIKLQQLAYGVFALGNRQYEHFNKIGIV
LDEELCKKGAKRLIEVGLGDDDQSIEDDFNAWKESLWSELDKLLKDEDDKSVATPYTAVIPEYRVV
THDPRFTTQKSMESNVANGNTTIDIHHPCRVDVAVQKELTHESDRSCIHLEFDISRTGITYETGD
HVGVYAENHVEIVEEAGKLLGHSLDLVFSIHADKEDGSPLESAVPPPFPGPCTLGTGLARYADLLN
PPRKSALVALAAYATEPSEAEKLKHLTSPDGKDEYSQWIVASQRSLLEVMAAFPSAKPPLGVFFAA
IAPRLQPRYYSISSCQDWAPSRVHVTSALVYGPTPTGRIHKGVCSTWMKNAVPAEKSHECSGAPIF
IRASNFKLPSNPSTPIVMVGPGIGLAPFRGELQERMALKEDGEELGSSLLFPGCRNRQMDFIYEDE
LNNEVDQGVISELIMAFSREGAQKEYVQHKMMEKAAQVWDLIKEEGYLYVCGDAKGMARDVHRTLH
TIVQEQEGVSSSEAEAIVKKLQTEGRYLRDVW (SEQ ID NO: 34)

>TcCPR [Taxus cuspidata]
MQANSNTVEGASQGKSLLDISRLDHIFALLLNGKGGDLGAMTGSALILTENSQNLMILTTALAVLV
ACVEFFVWRRGGSDIQKPAVRPTPLVKEEDEEEEDDSAKKKVTIFFGTQTGTAEGFAKALAEEEAKA
RYEKAVFKVVDLDNYAADDEQYEEKLKKEKLAFFMLATYGDGEPTDNAARFYKWFLEGKEREPWLS
DLTYGVEGLGNRQYEHENKVAKAVDEVLIEQGAKRLVPVGLGDDDQCIEDDETAWREQVWPELDQL
LRDEDDEPTSATPYTAAIPEYRVEIYDSVVSVYEETHALKQNGQAVYDIHHPCRSNVAVRRELHTP
LSDRSCIHLEFDISDTGLIYETGDHVGVHTENSIETVEEAAKLLGYQLDTIFSVHGDKEDGTPLGG
SSLPPPFPGPCTLRTALARYADLLNPPRKAAFLALAAHASDPAEAERLKFLSSPAGKDEYSQWVTA
SQRSLLEIMAEFPSAKPPLGVFFAAIAPRLQPRYYSISSSPRFAPSRIHVTCALVYGPSPTGRIHK
GVCSNWMKNSLPSEETHDCSWAPVFVRQSNFKLPADSTTPIVMVGPGTGFAPFRGFLQERAKLQEA
GEKLGPAVLFFGCRNRQMDYIYEDELKGYVEKGILTNLIVAFSREGATKEYVQHKMLEKASDTWSL
IAQGGYLYVCGDAKGMARDVHRTLHTIVQEQESVDSSKAEFLVKKLQMDGRYLRDIW (SEQ ID
NO: 35)
```

>AaCPR [Artemisia annua]
MAQSTTSVKLSPFDLMTALLNGKVSFDTSNTSDTNIPLAVFMENRELLMILTTSVAVLIGCVVVLV
WRRSSSAAKKAAESPVIVVPKKVIEDEVDDGRKKVIVFFGTQTGTAEGFAKALVEEAKRYEKAVF
KVIDLDDYAAEDDEYEEKLKKESLAFFFLATYGDGEPTDNAARFYKWFTEGEEKGEWLDKLQYAVF
GLGNRQYEHFNKIAKVVDEKLVEQGAKRLVPVGMGDDDQCIEDDFTAWKELVWPELDQLLRDEDDT
SVATPYTAAVAEYRVVFHDKPETYDQDQLTNGHAVHDAQHPCRSNVAVKKELHSPLSDRSCTHLEF
DISNTGLSYETGDHVGVYVENLSEVVDEAEKLIGLPPHTYFSVHADNEDGTPLGGASLPPPFPPCT
LRKALASYADVLSSPKKSALLALAAHATDSTEADRLKFLASPAGKDEYAQWIVASHRSLLEVMEAF
PSAKPPLGVFFASVAPRLQPRYYSISSSPRFAPNRIHVTCALVYEQTPSGRVHKGVCSTWMKNAVP
MTESQDCSWAPIYVRTSNFRLPSDPKVPVIMIGPGTGLAPFRGFLQERLAQKEAGTELGTAILFFG
CRNRKVDFIYEDELNNFVETGALSELVTAFSREGATKEYVQHKMTQKASDIWNLLSEGAYLYVCGD
AKGMAKDVHRTLHTIVQEQGSLDSSKAELYVKNLQMAGRYLRDVW (SEQ ID NO: 36)

>AtCPR1 [Arabidopsis thaliana]
MATSALYASDLFKQLKSIMGTDSLSDDVVLVIATTSLALVAGFVVLLWKKTTADRSGELKPLMIPK
SLMAKDEDDDLDLGSGKIRVSIFFGTQTGTAEGFAKALSEEIKARYEKAAVKVIDLDDYAADDDQY
EEKLKKETLAFFCVATYGDGEPTDNAARFYKWFTEENERDIKLQQLAYGVFALGNRQYEHFNKIGI
VLDEELCKKGAKRLIEVGLGDDDQSIEDDFNAWKESLWSELDKLLKDEDDKSVATPYTAVIPEYRV
VTHDPRFTTQKSMESNVANGNTTIDIHHPCRVDVAVQKELHTHESDRSCIHLEFDISRTGITYETG
DHVGVYAENHVEIVEEAGKLLGHSLDLVFSIHADKEDGSPLESAVPPPFPGPCTLGTGLARYADLL
NPPRKSALVALAAYATEPSEAEKLKHLTSPDGKDEYSQWIVASPLLEVMAAFPSAKPPLGVFFA
AIAPRLQPRYYSISSSPRLAPSRVHVTSALVYGPTPTGRIHKGVCSTWMKNAVPAEKSHECSGAPI
FIRASNFKLPSNPSTPIVMVGPGIGLAPFRGELQERMALKEDGEELGSSLLFFGCRNRQMDFIYED
ELNNFVDQGVISELIMAFSREGAQKEYVQHKMMEKAAQVWDLIKEEGYLYVCGDAKGMARDVHRTL
HTIVQEQEGVSSSEAEAIVKKLQTEGRYLRDVW (SEQ ID NO: 37)

>AtCPR2 [Arabidopsis thaliana]
MASSSSSSTSMIDLMAAIIKGEPVIVSDPANASAYESVAAELSSMLIENRQFAMIVTTSIAVLIG
CIVMLVWRRSGSGNSKRVEPLKPLVIKPREEEIDDGRKKVTIFFGTQTGTAEGFAKALGEEAKARY
EKTRFKIVDLDDYAADDDEYEEKLKKEDVAFFFLATYGDGEPTDNAARFYKWFTEGNDRGEWLKNL
KYGVFGLGNRQYEHFNKVAKVVDDILVEQGAQRLVQVGLGDDDQCIEDDFTAWREALWPELDTILR
EEGDTAVATPYTAAVLEYRVSIHDSEDAKENDINMANGNGYTVFDAQHPYKANVAVKRELHTPESD
RSCIHLEFDIAGSGLTYETGDHVGVLCDNLSETVDEALRLLDMSPDTYFSLHAEKEDGTPISSSLP
PPFPPPCNLRTALTRYACLLSSPKKSALVALAAHASDPTEAERLKHLASPAGKDEYSKWVVESQRSL
LEVMAEFPSAKPPLGVFFAGVAPRLQPRFYSISSSPKIAETRIHVTCALVYEKMPTGRIHKGVCST
WMKNAVPYEKSENCSSAPIFVRQSNFKLPSDSKVPIIMIGPGTGLAPFRGFLQERLALVESGVELG
PSVLFFGCRNRRMDFIYEEELQRFVESGALAELSVAFSREGPTKEYVQHKMMDKASDIWNMISQGA
YLYVCGDAKGMARDVHRSLHTIAQEQGSMDSTKAEGFVKNLQTSGRYLRDVW (SEQ ID NO: 38)

>ATR2 [Arabidopsis thaliana]
MASSSSSSTSMIDLMAAIIKGEPVIVSDPANASAYESVAAELSSMLIENRQFAMIVTTSIAVLIG
CIVMLVWRRSGSGNSKRVEPLKPLVIKPREEEIDDGRKKVTIFFGTQTGTAEGFAKALGEEAKARY
EKTRFKIVDLDDYAADDDEYEEKLKKEDVAFFFLATYGDGEPTDNAARFYKWFTEGNDRGEWLKNL
KYGVFGLGNRQYEHFNKVAKVVDDILVEQGAQRLVQVGLGDDDQCIEDDFTAWREALWPELDTILR
EEGDTAVATPYTAAVLEYRVSIHDSEDAKENDITLANGNGYTVFDAQHPYKANVAVKRELHTPESD
RSCIHLEFDIAGSGLTMKLGDHVGVLCDNLSETVDEALRLLDMSPDTYFSLHAEKEDGTPISSSLP
PPFPPPCNLRTALTRYACLLSSPKKSALVALAAHASDPTEAERLKHLASPAGKDEYSKWVVESQRSL
LEVMAEFPSAKPPLGVFFAGVAPRLQPRFYSISSSPKIAETRIHVTCALVYEKMPTGRIHKGVCST
WMKNAVPYEKSEKLFLGRPIFVRQSNFKLPSDSKVPIIMIGPGTGLAPFRGFLQERLALVESGVEL
GPSVLFFGCRNRRMDFIYEEELQRFVESGALAELSVAFSREGPTKEYVQHKMMDKASDIWNMISQG
AYLYVCGDAKGMARDVHRSLHTIAQEQGSMDSTKAEGFVKNLQTSGRYLRDVW (SEQ ID NO: 39)

>SrCPR1 [Stevia rebaudiana]
MAQSDSVKVSPFDLVSAAMNGKAMEKLNASESEDPTTLPALKMLVENRELLTLFTTSFAVLIGCLV
FLMWRRSSSKKLVQDPVPQVIVVKKKEKESEVDDGKKKVSIFYGTQTGTAEGFAKALVEEAKVRYE
KTSFKVIDLDDYAADDDEYEEKLKKESLAFFFLATYGDGEPTDNAANFYKWFTEGDDKGELLKKLQ
YGVFGLGNRQYEHFNKIAIVVDDKLTEMGAKRLVPVGLGDDDQCIEDDFTAWKELVWPELDQLLRD
EDDTSVTTPYTAAVLEYRVVYHDKPADSYAEDQTHTNGHVVHDAQHPSRSNVAFKKELHTSQSDRS
CTHLEFDISHTGLSYETGDHVGVYSENLSEVVDEALKLLGLSPDTYFSVHADKEDGTPIGGASLPP
PFPPCTLRDALTRYADVLSSPKKVALLALAAHASDPSEADRLKFLASPAGKDEYAQWIVANQRSLL
EVMQSFPSAKPPLGVFFAAVAPRLQPRYYSISSSPKMSPNRIHVTCALVYETTPAGRIHRGLCSTW
MKNAVPLTESPDCSQASIFVRTSNFRLPVDPKVPVIMIGPGTGLAPFRGFLQERLALKESGTELGS
SIFFFGCRNRKVDFIYEDELNNFVETGALSELIVAFSREGTAKEYVQHKMSQKASDIWKLLSEGAY
LYVCGDAKGMAKDVHRTLHTIVQEQGSLDSSKAELYVKNLQMSGRYLRDVW (SEQ ID NO: 40)

>SrCPR [Stevia rebaudiana]
MAQSESVEASTIDLMTAVLKDIVIDTANASDNGDSKMPPALAMMFEIRDLLLILITSVAVLVGCFV
VLVWKRSSGKKSGKELEPPKIVVPKRRLEQEVDDGKKKVTIFFGTQTGTAEGFAKALFEEAKARYE
KAAFKVIDLDDYAADLDEYAEKLKKETYAFFFLATYGDGEPTDNAAKEYKWFTEGDEKGVWLQKLQ
YGVFGLGNRQYEHFNKIGIVVDDGLTEQGAKRIVPVGLGDDDQSIEDDFSAWKELVWPELDLLLRD
EDDKAAATPYTAAIPEYRVVFHDKPDAFSDDHTQTNGHAVHDAQHPCRSNVAVKKELHTPESDRSC
THLEFDISHTGLSYETGDHVGVYCENLIEVVEEAGKLLGLSTDTYFSLHIDNEDGSPLGGPSLQPP
FPPCTLRKALTNYADLLSSPKKSTLLALAAHASDPTEADRLRFLASREGKDEYAEWVVANQRSLLE
VMEAFPSARPPLGVFFAAVAPRLQPRYYSISSSPKMEPNRIHVTCALVYEKTPAGRIHKGICSTWM
KNAVPLTESQDCSWAPIFVRTSNFRLPIDPKVPVIMIGPGTGLAPFRGFLQERLALKESGTELGSS

```
ILFFGCRNRKVDYIYENELNNFVENGALSELDVAFSRDGPTKEYVQHKMTQKASEIWNMLSEGAYL
YVCGDAKGMAKDVHRTLHTIVQEQGSLDSSKAELYVKNLQMSGRYLRDVW (SEQ ID NO: 41)

>SrCPR3 [Stevia rebaudiana]
MAQSNSVKISPLDLVTALFSGKVLDTSNASESGESAMLPTIAMIMENRELLMILTTSVAVLIGCVV
VLVWRRSSTKKSALEPPVIVVPKRVQEEEVDDGKKKVTVFFGTQTGTAEGFAKALVEEAKARYEKA
VPKVIDLDDYAADDDEYEEKLKKESLAFFFLATYGDGEPTDNAARFYKWFTEGDAKGEWLNKLQYG
VFGLGNRQYEHFNKIAKVVDDGLVEQGAKRLVPVGLGDDDQCIEDDFTAWKELVWPELDQLLRDED
DTTVATPYTAAVAEYRVVFHEKPDALSEDYSYTNGHAVHDAQHPCRSNVAVKKELHSPESDRSCTH
LEFDISNTGLSYETGDHVGVYCENLSEVVNDAERLVGLPPDTYFSIHTDSEDGSPLGGASLPPPFP
PCTLRKALTCYADVLSSPKKSALLALAAHATDPSEADRLKFLASPAGKDEYSQWIVASQRSLLEVM
EAFPSAKPSLGVFFASVAPRLQPRYYSISSSPKMAPDRIHVTCALVYEKTPAGRIHKGVCSTWMKN
AVPMTESQDCSWAPIYVRTSNFRLPSDPKVPVIMIGPGTGLAPFRGFLQERLALKEAGTDLGLSIL
FFGCRNRKVDFIYENELNNFVETGALSELIVAFSREGPTKEYVQHKMSEKASDIWNLLSEGAYLYV
CGDAKGMAKDVHRTLHTIVQEQGSLDSSKAELYVKNLQMSGRYLRDVW (SEQ ID NO: 42)

>PgCPR [Pelargonium graveolens]
MAQSSSGSMSPFDFMTAIIKGKMEPSNASLGAAGEVTAMILDNRELVMILTTSIAVLIGCVVVFIW
RRSSSQTPTAVQPLKPLLAKETESEVDDGKQKVTIFFGTQTGTAEGFAKALADEAKARYDKVTFKV
VDLDDYAADDEEYEEKLKKETLAFFFLATYGDGEPTDNAARFYKWFLEGKERGEWLQNLKFGVFGL
GNRQYEHFNKIAIVVDEILAEQGGKRLISVGLGDDDQCIEDDFTAWRESLWPELDQLLRDEDDTTV
STPYTAAVLEYRVVFHDPADAPTLEKSYSNANGHSVVDAQHPLRANVAVRRELHTPASDRSCTHLE
FDISGTGIAYETGDHVGVYCENLAETVEEALELLGLSPDTYFSVHADKEDGTPLSGSSLPPPFPPC
TLRTALTLHADLLSSPKKSALLALAAHASDPTEADRLRHLASPAGKDEYAQWIVASQRSLLEVMAE
FPSAKPPLGVFFASVAPRLQPRYYSISSSPRIAPSRIHVTCALVYEKTPTGRVHKGVCSTWMKNSV
PSEKSDECSWAPIFVRQSNFKLPADAKVPIIMIGPGIGLAPFRGFLQERLALKEAGTELGPSILFF
GCRNSKMDYIYEDELDNEVQNGALSELVLAFSREGPTKEYVQHKMMEKASDIWNLISQGAYLYVCG
DAKGMARDVHRTLHTIAQEQGSLDSSKAESMVKNLQMSGRYLRDVW (SEQ ID NO: 43)
```

LINKER SEQUENCES

```
GSGGGGS (SEQ ID NO: 44)

GSGEAAAK (SEQ ID NO: 45)

GSGEAAAKEAAAK (SEQ ID NO: 46)

GSGMGSSSN (SEQ ID NO: 47).
```

P450 ENZYMES WITH TRANSMEMBRANE DOMAIN DELETED

```
>t22ZzHO [Zingiber zerumbet]
LLIKRSSRSSVHKQQVLLASLPPSPPRLPLIGNIHQLVGGNPHRILLQLARTHGPLICLRLGQVDQ
VVASSVEAVEEIIKRHDLKFADRPRDLIFSRIFFYDGNAVVMTPYGGEWKQMRKIYAMELLNSRRV
KSFAAIREDVARKLIGEIAHKAFAQTPVINLSEMVMSMINAIVIRVAFGDKCKQQAYFLHLVKEAM
SYVSSFSVADMYPSLKFLDTLIGLKSKLEGVHGKLDKVFDEIIAQRQAALAAEQAEEDLIIDVLLK
LKDEGNQEFPITYTSVKAIVMEIFLAGTETESSSVIDWVMSELIKNPKAMEKVQKEMREAMQGKIKL
EESDIPKFSYLNLVIKETLRLHPPGPLLFPRECRETCEVMGYRVPAGARLLINAFALSRDEKYWGS
DAESFKPERFEGISVDFKGSNFEFMPFGAGRRICPGMTFGISSVEVALAHLLFHFDWQLPQGMKIE
DLDMMEVSGMSATRRSPLLVLAKLIIPLP (SEQ ID NO: 48)

>t20BsGAO [Barnadesia spinosa]
LLIGSKSTKNSLPEAWRLPIIGHMHHLVGILPHRGVIDMARKYGSLMHLQLGEVSTIVVSSPRWAK
EVLITYDITFANRPETLIGEIVAYHNTDIVLSPYGEYWRQLRKLCTLELLSAKKVKSFQSLREEEC
WNLVKEVRSSGSGSPVDLSESIFKLIATILSRAAFGKGIKDQREFTEIVKEILRLIGGFDVADIFP
SKKILHHLSGKRAKLINIHNKLDSLINNIVSEHPGSRISSSQESLLDVLLRLKDSAELPLISDNVK
AVILDMFGAGTDISSATIEWAISELIRCPRAMEKVQTELRQALNGKERIQEEDIQELSYLKLVIKE
TLRLHPPLPLVMPRECREPCVLAGYEIPTKIKLIVNVFAINRDPEYWKDAETFMPERFENSPINIM
GSEYEYLPFGAGRRMCPGAALGLANVELPLAHILYYFNWKLPNGARLDELDMSECFGATVQRKSEL
LLVPTAYKTANNSA (SEQ ID NO: 49)

>t16HmPO [Hyoscyamus muticus]
FLLRKWKNSNSQSKKLPPGPWKLPLLGSMLHMVGGLPHHVLRDLAKKYGPLMHLQLGEVSAVVVIS
PDMAKEVLKTHDIAFASRPKLLAPEIVCYNRSDIAFCPYGDYWRQMRKICVLEVLSAKNVRSFSSI
RRDEVLRLVNFVRSSTSEPVNFTERLFLFTSSMICRSAFGKVFKEQETFIQLIKEVIGLAGGFDVA
DIFPSLKFLHVLIGMEGKIMKAHHKVDAIVEDVINEHKKNLAMGKINGALGGEDLIDVLLRLMNDG
GLQFPITNDNIKAIIEDMFAAGTETSSSILVWAMVQMMRNPTILAKAQAEVREAFKGKETEDENDV
EELKYLKLVIKETLRLHPPVPLLVPRECREETEINGYTIPVKIKVMVNVWALGRDPKYWDDADNFK
PERFEQCSVDFIGNNFEYLPFGGGRRICPGISFGLANVYLPLAQLLYHFDWKLPTGMEPKDLDLTE
LVGVTAARKSDLMLVATPYQPSRE (SEQ ID NO: 50)

>t19LsGAO [Lactuca sativa]
KLATRPKSIKKQLPEASRLPIIGHMHHLIGIMPHRGVMDLARKHGSLMHLQLGEVSTIVVSSPKWA
KEILITYDITFANRPETLIGEIIAYHNTDIVLAPYGEYWRQLRKLCTLELLSVKKVKSFQSIREEE
CWNLVKEVKESGSGKPINLSESIFTMIATILSRAAFGKGIKDQREFTEIVKEILRQTGGEDVADIF
PSKKFLHHLSGKRARLTSIHKKLDNLINNIVAEHHVSTSSKANEILLDVLLRLKDSAEFPLTADNV
KAIILDMFGAGTDISSATVEWAISELIRCPRAMEKVQAELRQALNGKEKIQEEDIQDLAYLNLVIR
ETLRLHPPLPLVMPRECREPVNLAGYEIANKTKLIVNVFAINRDPEYWKDAEAFIPERFENNPNNI
```

```
MGADYEYLPFGAGRRMCPGAALGLANVQLPLANILYHENWKLPNGASHDQLDMIESFGATVQRKTE
LLLVPSF (SEQ ID NO: 51)

>t16NtEAO [Nicotiani tabacum]
FLLRKWKNSNSQSKKLPPGPWKIPILGSMLHMIGGEPHHVLRDLAKKYGPLMHLQLGEISAVVVIS
RDMAKEVLKTHDVVFASRPKIVAMDIICYNQSDIAFSPYGDHWRQMRKICVMELLNAKNVRSFSSI
RRDEVVRLIDSIRSDSSSGELVNFTQRIIWFASSMICRSAFGQVLKGQDIFAKKIREVIGLAEGFD
VVDIFPTYKFLHVLSGMKRKLLNAHLKVDAIVEDVINEHKKNLAAGKSNGALGGEDLIDVLLRLMN
DISLQFPITNDNIKAVIVDMFAAGTETSSITTVWAMAEMMKNPSVETKAQAEVREAFRDKVSFDEN
DVEELKYLKLVIKETLRLHPPSPLLVPRECREDTDINGYTIPAKTKVMVNVWALGRDPKYWDDAES
FKPERFEQCSVDFFGNNFEFLPFGGGRRICPGMSFGLANLYLPLAQLLYHFDWKLPTGIMPRDLDL
TELSGITIARKGGLYLNATPYQPSRE (SEQ ID NO: 52)

>t26CpVO [Citrus x paradisi]
WVWLRPKKLEKFLRQQGLKGNSYRLLFGDLKENSIELKEAKARPLSLDDDIAIRVNPFLHKLVNDY
GKNSFMWFGPTPRVNIMNPDQIKAIFTKINDFQKVNSIPLARLLIVGLATLEGEKWAKHRKLINPA
FHQEKLKLMLPAFYLSCIEIITKWEKQMSVEGSSELDVWPYLANLISDVISRTAFGSSYEEGRRIF
QLQAELAELTMQVERSVHIPGWRFLPTKRNRRMKEIDKEIRASLMGIIKNREKAMRAGEAANNDLL
GILMETSFREIEEHGNNKNVGFSMNDVIEECKLFYFAGQETTSVLLNWTMVLLSKHQDWQERARQE
VLQVFGNNKPDYDGLNHLKIVQMILYEVLRLYPPVTVLSRAVFKETKLGNLTLPAGVQIGLPMILV
HQDPELWGDDAVEFKPERFAEGISKAAKNQVSYFPFALGPRICVGQNFALVEAKMATAMILQNYSF
ELSPSYVHAPTAVPTLHPELGTQLILRKLWCKNN (SEQ ID NO: 53)

>t23AaAO [Artemesia annua]
FVYKFAIRSKSIKKSLPEPWRLPIIGHMHHLIGTTPHRGVRDLARKYGSLMHLQLGEVPTIVVSSP
KWAKEILITYDITFANRPETLIGEIVLYHNTDVVLAPYGEYWRQLRKICTLELLSVKKVKSFQSLR
EEECWNLVQEIKASGSGRPVNLSENVFKLIATILSRAAFGKGIKDQKELTEIVKEILRQTGGEDVA
DIFPSKKFLHHLSGKRARLTSLRKKIDNLIDNLVAEHTVNTSSKTNETLLDVLLRLKDSAEFPLTS
DNIKAIILDMFGAGTDISSSTIEWAISELIKCPKAMEKVQAELRKALNGKEKIHEEDIQELSYLNM
VIKETLRLHPPLPLVLPRECRQPVNLAGYNIPNKTKLIVNVFAINRDPEYWKDAEAFIPERFENSS
ATVMGAEYEYLPFGAGRRMCPGAALGLANVQLPLANILYHFNWKLPNGVSYDQIDMIESSGATMQR
KTELLLVPSF (SEQ ID NO: 54)

>t21AtKO [Arabidopsis thaliana]
FFFKKLLSFSRKNMSEVSTLPSVPVVPGFPVIGNLLQLKEKKPHKIFTRWSEIYGPIYSIKMGSSS
LIVLNSTETAKEAMVIRFSSISTRKLSNALTVLICDKSMVATSDYDDFHKLVKRCLLNGLLGANAQ
KRKRHYRDALIENVSSKLHAHARDHPQEPVNFRAIFEHELFGVALKQAFGKDVESIYVKELGVILS
KDEIFKVLVHDMMEGAIDVDWRDFFPYLKWIPNKSFEARIQQKHKRRLAVMNALIQDRLKQNGSES
DDDCYLNFLMSEAKTLIKEQIAILVWETIIETADTTLVITEWAIYELAKHPSVQDRLCKEIQNVCG
GEKFKEEQLSQVPYLNGVFHETLRKYSPAPLVPIRYAHEDTQIGGYHVPAGSEIAINIYGCNMDKK
RWERPEDWWPERFLDDGKYETSDLHKTMAFGAGKRVCAGALQASLMAGIAIGRLVQEFEWKLRDGE
EENVDTYGLTSQKLYPLMAIINPRRS (SEQ ID NO: 55)

>t30SrKO [Stevia rebaudiana]
WYLKSYTSARRSQSNHLPRVPEVPGVPLLGNLLQLKEKKPYMTFTRWAATYGPIYSIKTGATSMVV
VSSNEIAKEALVIRFQSISTRNLSKALKVLTADKTMVAMSDYDDYHKTVKRHILTAVLGPNAQKKH
RIHRDIMMDNISTQLHEFVKNNPEQEEVDLRKIFQSELFGLAMRQALGDVEVLGIKITMNRD
EIFQVLVVDPMMGAIDVDWRDFFPYLKWVPNKKFENTIQQMYIRREAVMKSLIKEHHKKRIASGEKL
NSYIDYLLSEAQTLIDQQLLMSLWEPIIESSDITMVITEWAMYELAKNPKLQDRLYRDIKSVCGSE
KITEEEHLSQLPYITAIFHETLRRHSPVPIIPLRHVHEDTVLGGYHVPAGTELAVNIYGCNMDKNVW
ENPEEWNPERFMKENETIDFQKTMAFGGGKRVCAGSLQALLTASIGIGRMVQEFEWKLKDMIQEEV
NTIGLITQMLRPLRAIIKPRI (SEQ ID NO: 56)

>t52PpKO [Physcomitrella patens]
FVARTCLRNKKRLPPAIPGGLPVLGNLLQLTEKKPHRTFTAWSKEHGPIFTIKVGSVPQAVVNNSE
IAKEVLVIKFASISKRQMPMALRVLIRDKTMVAMSDYGEEHRMLKKLVMTNLLGPTIQNKNRSLRD
DALIGMIEGVLAELKASPTSPKVVNVRDYVQRSLFPFALQQVFGYIPDQVEVLELGICVSTWDMFD
ALVVAPLSAVINVDWRDFFPALRWIPNRSVEDLVRTVDFKRNSIMKALIRAQRMRLANLKEPPRCY
ADIALTEATHLTEKQLEMSLWEPIIESADTTLVISEWAMYEIAKNPDCQDRLYREIVSVAGTERMV
TEDDLPNMPYLGAIIKETLRKYTPVPLIPSRFVEEDITLGGYDIPKGYQILVNLFAIANDPAVWSN
PEKWDPERMLANKKVDMGFRDFSLMPFGAGKRMCAGITQAMFIIPMNVAALVQHCEWRLSPQEISN
INNKIEDVVYLTTHKLSPLSCEATPRISHRLP (SEQ ID NO: 57)

>t15PsVO [Pleurotus sapidus]
MGKLHPLAIIPDYKGSMAASVTIFNKRINPLDISVNQANDWPWRYAKTCVLSSDWALHEMIIHLNN
THLVEEAVIVAAQRKLSPSHIVERLLEPHWVVILSLNALARSVLIPEVIVPIAGFSAPHIFQFIRE
SPINFDWKSLYVPADLESRGFPVDQLNSPKFHNYAYARDINDMWTTLKKFVSSVLQDAQYYPDDAS
VAGDTQIQAWCDEMRSGMGAGMINFPESITTVDDLVNMVIMCIHIAAPQHTAVNYLQQYYQTFVSN
KPSALFSPLPTSIAQLQKYTESDLMAALPLNAKRQWLLMAQIPYLLSMQVQEDENIVIYAANASTD
KDPIIASAGRQLAADLKKLAAVFLVNSAQLDDQNTPYDVLAPEQLANAIVI (SEQ ID NO: 58)

>t20CiVO [Cichorium intybus]
LLTRTTSKKNLLPEPWRLPIIGHMHHLIGTMPHRGVMELARKHGSLMHLQLGEVSTIVVSSPRWAK
EVLTTYDITFANRPETLTGEIVAYHNTDIVLAPYGEYWRQLRKLCTLELLSNKKVKSFQSLREEEC
WNLVKDIRSTGQGSPINLSENIFKMIATILSRAAFGKGIKDQMKFTELVKEILRLIGGEDVADIFP
SKKLLHHLSGKRAKLTNIHNKLDNLINNIIAEHPGNRTSSSQETLLDVLLRLKESAEFPLTADNVK
AVILDMFGAGTDTSSATIEWAISELIRCPRAMEKVQTELRQALNGKERIQEEDLQELNYLKLVIKE
TLRLHPPLPLVMPRECREPCVLGGYDIPSKTKLIVNVFAINRDPEYWKDAETFMPERFENSPITVM
```

-continued

GSEYEYLPFGAGRRMCPGAALGLANVELPLAHILYFNWKLPNGKTFEDLDMTESFGATVQRKTELL
LVPTDFQTLTAST (SEQ ID NO: 59)

>t20HaGAO [Helianthus annuus]
LLTRPTSSKNRLPEPWRLPIIGHMHHLIGTMPHRGVMDLARKYGSLMHLQLGEVSAIVVSSPKWAK
EILTTYDIPFANRPETLTGEITAYHNTDIVLAPYGEYWRQLRKLCTLELLSVKKVKSFQSLREEEC
WNLVQEIKASGSGTPFNLSEGIFKVIATVLSRAAFGKGIKDQKQFTEIVKEILREIGGEDVADIFP
SKKFLHHLSGKRGRLTSIHNKLDSLINNLVAEHTVSKSSKVNETLLDVLLRLKNSEEFPLTADNVK
AIIILDMFGAGTDTSSATVEWAISELIRCPRAMEKVQAELRQALNGKERIKEEEIQDLPYLNLVIRE
TLRLHPPLPLVMPRECRQAMNLAGYDVANKTKLIVNVFAINRDPEYWKDAESFNPERFENSNTTIM
GADYEYLPFGAGRRMCPGSALGLANVQLPLANILYYFKWKLPNGASHDQLDMTESFGATVQRKTEL
MLVPSF (SEQ ID NO: 60)

The invention claimed is:

1. A method for biosynthesis of one or more chemical species in *Escherichia coli*, said method comprising:
expressing one or more recombinant biosynthetic pathways that produce one or more chemical species in *Escherichia coli*, the one or more biosynthetic pathways comprising at least one membrane-anchored P450 enzyme, wherein at least a portion of the transmembrane region of the P450 enzyme is substituted with a transmembrane domain derived from an *Escherichia coli* inner membrane cytoplasmic C-terminus protein, and
culturing the *Escherichia coli* to produce the one or more chemical species from the one or more biosynthetic pathways.

2. The method of claim 1, wherein the *Escherichia coli* overexpresses at least one gene in the MEP pathway.

3. The method of claim 1, wherein the *Escherichia coli* expresses at least two membrane-anchored P450 enzymes, wherein at least a portion of the transmembrane region of at least one of the P450 enzymes is substituted with a transmembrane domain derived from an *Escherichia coli* inner membrane cytoplasmic C-terminus protein, wherein the P450 enzymes are optionally derived from plant P450 enzymes.

4. The method of claim 1, wherein the at least one membrane-anchored P450 enzyme, is CiVO, HmPO, LsGAO, BsGAO, NtEAO, SrKO, SrKAH, AtKAH, ZzHO, CpVO, MsL60H, NtVO, StVO, AtKO, Ci2VO, AaAO, or Taxus 5-alpha hydroxylase.

5. The method of claim 1, wherein the chemical species is a terpenoid.

6. The method of claim 5, wherein the terpenoid is selected from the group consisting of a monoterpenoid, a sesquiterpenoid, diterpenoid, a sesterpenoid, and a triterpenoid.

7. The method of claim 6, wherein the biosynthetic pathway involves overexpression of a geranyl diphosphate synthase (GPS), a gernanylgeranyl diphosphate synthase (GGPS), a farnsesyl diphosphate synthase (FPS), or a farnesyl geranyl diphosphate synthase (FGPPS).

8. The method of claim 5, wherein the terpenoid is selected from the group consisting of alpha-sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Sabinene, Steviol, Steviol glycoside, Taxadiene, Thymol, and Valencene, or derivative thereof.

9. The method of claim 1, wherein IbpA is not overexpressed during the culturing.

10. The method of claim 1, wherein the *Escherichia coli* expresses one or more CPR enzymes as a translational fusion or operon with the P450 enzymes; or wherein the P450 and the CPR are expressed separately and the level of expression of the P450 enzyme and the CPR are approximately 2:1 to 1:2.

11. The method of claim 10, wherein the cell expresses a single CPR protein.

12. The method of claim 10, wherein at least one CPR partner comprises a membrane-anchor having a single pass transmembrane domain derived from an *Escherichia coli* protein.

13. The method of claim 1, wherein the transmembrane domain derived from an *Escherichia coli* inner membrane cytoplasmic C-terminus protein is a single pass transmembrane domain encoded by an *Escherichia coli* gene selected from the group consisting of waaA, ypfN, yhcB, yhbM, yhhm, zipA, ycgG, djlA, sohB, IpxK, F110, motA, htpx, pgaC, ygdD, hemr, and ycls, or derivative thereof.

14. The method of claim 13, wherein the single pass transmembrane domain is derived from yhcB or zipA gene, or a derivative thereof.

15. The method of claim 1, wherein the transmembrane domain derived from an *Escherichia coli* inner membrane cytoplasmic C-terminus protein is from 8 to 75 amino acids in length.

16. The method of claim 15, wherein at least one membrane anchor is selected from:
the N-terminal 20 to 22 amino acids of yhcB (SEQ ID NO: 18),
the N-terminal 19 to 21 amino acids of yhhM (SEQ ID NO: 20),
the N-terminal 24 to 26 amino acids of zipA (SEQ ID NO: 21),
the N-terminal 21 to 23 amino acids of ypfN (SEQ ID NO: 17),
the N-terminal 27 to 29 amino acids of SohB (SEQ ID NO: 24), and
the N-terminal 20-22 amino acids of waaA (SEQ ID NO: 16), or derivative thereof.

17. The method of claim 1, further comprising recovering the chemical species from the culture.

18. An *Escherichia coli* host cell expressing one or more recombinant biosynthetic pathways that produce one or more chemical species, where the biosynthetic pathways comprise at least one membrane-anchored P450 protein, wherein at least a portion of the transmembrane region of the P450 enzyme is substituted with a transmembrane domain derived from an *Escherichia coli* inner membrane cytoplasmic C-terminus protein.

19. A plant P450 enzyme comprising an N-terminal truncation and a single-pass transmembrane region derived from an *Escherichia coli* inner membrane cytoplasmic C-terminus protein.

20. A polynucleotide encoding the enzyme of claim 19.

* * * * *